United States Patent
Okazaki et al.

(10) Patent No.: US 6,482,918 B2
(45) Date of Patent: Nov. 19, 2002

(54) SELENIUM-CONTAINING TRANSPARENT OPTICAL MATERIAL

(75) Inventors: Koju Okazaki, Fukuoka (JP); Mamoru Tanaka, Fukuoka (JP); Shiro Honma, Fukuoka (JP); Hiroyuki Morijiri, Fukuoka (JP); Yoshinobu Kanemura, Fukuoka (JP); Masahiko Kusumoto, Kanagawa (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 09/934,858

(22) Filed: Aug. 23, 2001

(65) Prior Publication Data

US 2002/0120097 A1 Aug. 29, 2002

Related U.S. Application Data

(62) Division of application No. 09/570,613, filed on May 12, 2000, now Pat. No. 6,303,747, which is a division of application No. 09/171,468, filed as application No. PCT/JP98/00714 on Feb. 23, 1998, now Pat. No. 6,124,424.

(30) Foreign Application Priority Data

| Feb. 21, 1997 | (JP) | 9-037846 |
| Oct. 22, 1997 | (JP) | 9-289648 |
| Oct. 31, 1997 | (JP) | 9-300344 |
| Nov. 6, 1997 | (JP) | 9-304688 |

(51) Int. Cl.$^7$ .............................................. C08G 65/00
(52) U.S. Cl. .................. 528/405; 528/403; 528/374; 351/49; 351/166; 351/232
(58) Field of Search .......................... 528/405, 403, 528/374; 351/49, 166, 232

(56) References Cited

U.S. PATENT DOCUMENTS

| 4,320,939 A | 3/1982 | Mueller |
| 4,320,940 A | 3/1982 | Mueller et al. |
| 5,604,280 A | 2/1997 | Pozzo et al. |

FOREIGN PATENT DOCUMENTS

| JP | 3-166203 | 7/1991 |
| JP | 9-20770 A | 1/1997 |

OTHER PUBLICATIONS

Chem. Abstract, 129:246327 "Selenium-containing transparent optical materials and plastic lenses with high refractive index and their manufacture", Okazaki et al, 1998.

*Primary Examiner*—Duc Truong
(74) *Attorney, Agent, or Firm*—Burns, Doane, Swecker & Mathis LLP

(57) ABSTRACT

There are herein disclosed a transparent optical material containing at least one selenium atom, a plastic lens comprising the transparent optical material, and methods for preparing them. In addition, there are also disclosed novel selenium-containing compounds represented by the following formulae (1), (2) and (4) which are useful for the transparent optical material and the plastic lens:

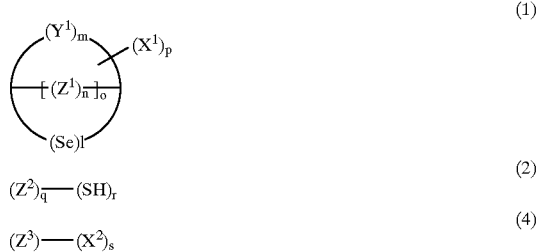

wherein symbols are as defined in the specification.

6 Claims, No Drawings

SELENIUM-CONTAINING TRANSPARENT OPTICAL MATERIAL

This application is a divisional of application Ser. No. 09/570,613, filed on May 12, 2000, now U.S. Pat. No. 6,303,747 issued Oct. 16, 2001, which is a divisional of originally filed application Ser. No. 09/171,468, filed Oct. 19, 1998, now U.S. Pat. No. 6,124,424 issued Sep. 26, 2000, which was a national stage filing under 35 U.S.C. §371 of International Application No. PCT/JP98/00714 filed on Feb. 23, 1998.

TECHNICAL FIELD

The present invention relates to a novel transparent optical material which has high refractive index, low dispersion and excellent optical property, and is used for a glasses lens, camera lens, prism, substrate for an information recording medium, pickup lens, optical fiber, optical filter and the like, to a plastic lens using this material, and to a method for producing the same. Further, the present invention also relates to a novel selenium-containing compound useful as a raw material for the above-described transparent optical material.

BACKGROUND ART

A transparent optical material and a plastic lens are molded articles required to have high transparency and optical uniformity as is apparent from the uses thereof. As a material conventionally used widely in these uses, there is listed a plastic material obtained by radical polymerization of diethylene glycol bis(allyl carbonate) (hereinafter, abbreviated as DAC).

However, this DAC plastic material has low refractive index (Nd) as low as 1.50, and when used for a plastic lens, there is a problem that the resulting lens has large edge thickness and is deficient in fashionable appearance.

For improving this problem, various investigations have been made for increasing refractive index. For example, there are listed a method in which tetrabromo bisphenol-A is reacted with an isocyanate compound (Japanese Patent Application Laid-Open (JP-A) No. 58-164,615), a method in which xylylenedithiol dimethacryalte is polymerized (JP-A No. 64-31,759), a method in which 1,4-dithiane-2,5-dimercaptomethyl is used (Japanese Patent Application Publication (JP-B) No. 6-5,323), and the like.

Also the present inventors have previously suggested methods in which a polythiol having in the molecule a sulfur atom other than a mercapto group is used (JP-A Nos. 2-270,859 and 7-252,207), and the like.

Any of these methods is a method in which refractive index is improved by introducing a benzene ring, a halogen atom such as bromine, or a sulfur atom into the molecule. However, when refractive index is desired to be further improved, these methods have been often insufficient. That is, these methods have not been recognized as methods fully satisfying eager requirement to further decrease the edge thick of a lens.

DISCLOSURE OF THE INVENTION

Accordingly, an object of the present invention is to provide a transparent optical material and a plastic lens which can have further improved refractive index and further decreased edge thickness of the lens.

Further object of the present invention is to provide a novel compound useful for the novel transparent optical material, and a composition containing this compound.

The present inventors have intensively investigated to satisfy the above-described strong requirement, and as a result, found that refractive index can be further improved by introducing a selenium atom into the molecule of an optical material, completing the present invention.

Namely, the present invention provides a transparent optical material and a plastic lens containing in the molecule at least one selenium atom, and a method for producing a transparent optical material and a plastic lens in which a composition containing at least one reactive monomer or oligomer having at least one selenium atom in its molecule is subjected to casting polymerization.

This technique for introducing a selenium atom into the molecule of an optical material has not been known until now.

The present invention contains the following subjects.
1. A transparent optical material which contains at least one selenium atom.
2. A plastic lens which comprises the transparent optical material according to subject 1.
3. A method for producing the transparent optical material in subject 1 which comprises the step of cast-polymerizing a composition including at least one reactive monomer or oligomer having at least one selenium atom in its molecule.
4. A method for producing the plastic lens in subject 2 in which comprises the step of cast-polymerizing a composition including at least one reactive monomer or oligomer having at least one selenium atom in its molecule.
5. The production method according to subjects 3 or 4, wherein the reactive monomer or oligomer having at least one selenium atom in its molecule is selected from selenium atom-including active hydrogen compounds having at least one functional group of a hydroxyl group, mercapto group, seleno group and amino group, selenium atom-including self-polymerizable compounds having at least one functional group of a (meth)acrylic group, allyl carbonate group, allyl thiocarbonate group, allyl selenocarbonate group, allyl group, vinyl group, isopropenyl group, epoxy group, thioepoxy group and selenoepoxy group, and selenium atom-including isocyanates having at least one functional group of an isocyanate group, isothiocyanate group and isoselenocyanate group.
6. A selenium-containing alicyclic compound represented by formula (1):

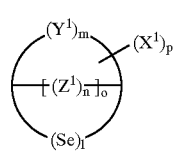

(1)

wherein, $Y^1$ and $Z^1$ each represent —$CH_2$—, =CH—, C atom, Se atom, S atom, $SO_2$, SO or O atom, and the hydrogen atom of methylene or methine may also be substituted by a $C_1$ to $C_3$ lower alkyl group, $C_1$ to $C_3$ lower alkoxy group, $C_1$ to $C_3$ lower alkylthio group, F atom, Cl atom or Br atom; $X^1$ represents a functional group selected from an SH group, NCO group, NCS group, acryloyl group, methacryloyl group, vinyloxy group, vinylthio group, vinylseleno group, vinyl carbonate group, vinyl thiocarbonate group, vinyl selenocarbonate group, allyloxy group, allylthio group, allylseleno group, allyl carbonate group, allyl thiocarbonate group, allyl selenocarbonate group, isopropenyloxy group, isopropenylthio group, isopropenylseleno group, isopropenyl carbonate group, isopropenyl thiocarbonate group, isopropenyl selenocarbonate group, epoxy group and thioepoxy group, or an alkyl residue composed of such functional group and an alkylene group having 10 or less carbon atoms, l, m, n, o and p represent an integer of 1 to 5, 2 to 10, 0 to 5, 0 to 3 and 2 to 6, respectively.

7. The selenium-containing alicyclic compound of subject 6, wherein the alicyclic structure is 4 to 10-membered ring.
8. The selenium-containing alicyclic compound of subject 6, wherein the alicyclic structure is 5 to 9-membered ring and the alkylene group is composed of 0 to 4 carbon atoms.
9. A composition including at least one selenium-containing alicyclic compound of any one of subjects 6 to 8.
10. A selenium-containing polythiol having 3 or more functional groups which is represented by formula (2):

$$(Z^2)_q\text{—}(SH)_r \quad (2)$$

wherein, $Z^2$ represents an alkylene group having at least one Se atom, q represents an integer from 1 to 20 and r represents an integer from 3 to 6.

11. The selenium-containing polythiol having 3 or more functional groups according to subject 10, which is represented by formula (3):

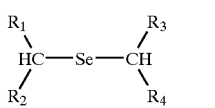

wherein $R_1$, $R_2$, $R_3$ and $R_4$ each independently represents a hydrogen atom, mercapto group,

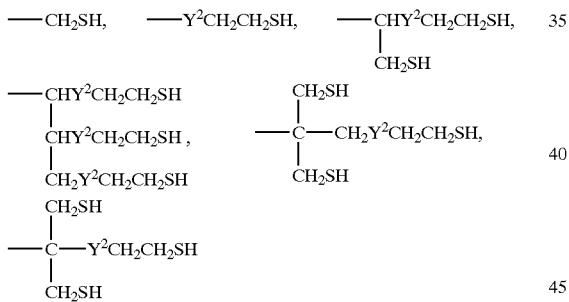

and $Y^2$ represents a sulfur atom or an Se atom.

12. A composition which contains at least one selenium-containing polythiol having 3 or more functional groups described in claim 10.
13. A selenium-containing aliphatic compound having 2 or more functional groups which is represented by formula (4):

$$(Z^3)\text{—}(X^2)_s \quad (4)$$

wherein $Z^3$ represents an Se atom or an alkylene group including at least one Se atom; $X^2$ represents a functional group selected from an acryloyl group, methacryloyl group and thioepoxy group, or an alkyl residue having this functional group; and s represents an integer from 2 to 6.

14. The selenium-containing aliphatic compound according to subject 13 which is represented by formula (5):

$$X_1\text{—}Se\text{—}X_2 \quad (5)$$

wherein, $X_2$ and $X_2$ are the same or different, and they are each

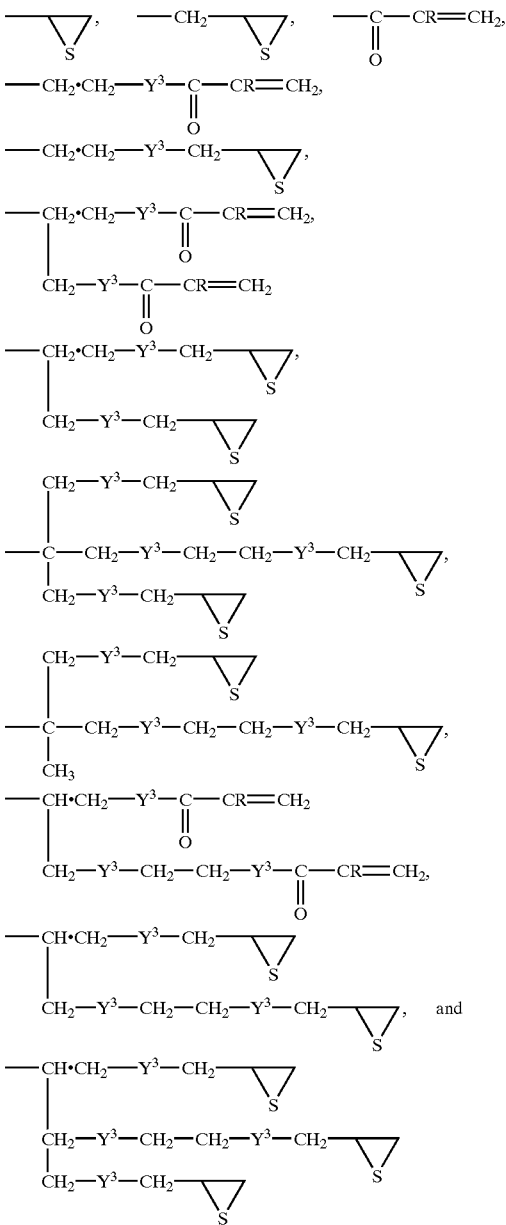

in which $Y^3$ represents a sulfur atom, oxygen atom or Se atom, and R represents a hydrogen atom or a methyl group.

15. A composition which contains at least one selenium-containing aliphatic compound of subject 13.

BEST MODE FOR CARRYING OUT THE INVENTION

The present invention will be described in detail below.

The transparent optical material and plastic lens are obtained by casting polymerization of a composition containing at least one reactive monomer or oligomer having at least one selenium atom in its molecule.

This reactive monomer or oligomer having at least one selenium atom in its molecule is a monomer or oligomer having at least one selenium atom in the molecule which carries out polymerization reaction when one or more kinds thereof are mixed and reacted.

Examples thereof include selenium atom-containing active hydrogen compounds having in the molecule at least one functional group selected from a hydroxyl group, mercapto group, seleno group and amino group, selenium atom-containing self-polymerizable compounds having in the molecule at least one functional group selected from a (meth)acrylic group, allyl carbonate group, allyl thiocarbonate group, allyl selenocarbonate group, allyl group, vinyl group, isopropenyl group, epoxy group, thioepoxy group and selenoepoxy group, and selenium atom-containing isocyanates having at least one functional group selected from an isocyanate group, isothiocyanate group and isoselenocyanate group, and further, oligomers thereof. Among them, a further preferable compound is a selenium-containing di-functional monomer or an oligomer in which any two or more functional groups selected from a mercapto group, isocyanate group, isothiocyanate group, acrylic group, methacrylic group, vinyloxy group, vinylthio group, vinylseleno group, vinyl carbonate group, vinyl thiocarbonate group, vinyl selenocarbonate group, allyoxy group, allylthio group, allylseleno group, allyl carbonate group, allyl thiocarbonate group, allyl selenocarbonate group, isopropenyloxy group,. isopropenylthio group, isopropenylseleno group, isopropenyl carbonate group, isopropenyl thiocarbonate group, isopropenyl selenocarbonate group, epoxy group, thioepoxy group and selenoepoxy group are connected in the molecule.

The selenium atom-containing active hydrogen compounds are compounds containing a selenium atom, having at least any one functional group selected from a hydroxy group, mercapto group, selenyl group, telluronyl group and amino group.

Examples thereof include 2-selenoethanol, bis(2-mercaptoethyl)selenide, 2,3-bis(2-mercaptoethylseleno)-1-propanethiol, bis(mercaptomethyl)-3,9-dithia-6-seleno-1,11-undecanedithiol, xylylenediselenol, bis(4-hydroxy-2-selenabutyl)benzene, 1,4-dithiane-2,5-diselenol, 1,4-dithiane-2,5-bis(selenomethyl), bis(4-mercapto-2-selenabutyl)-1,4-dithiane, bis(4-mercapto-2-selenabutyl)benzene, 4-thia-1-selenane-2,6-dithiol, 4-thia-1-selenane-3,5-dithiol, 4-thia-1-selenane-2,6-dimercaptomethyl, 4-thia-1-selenane-3,5-dimercaptomethyl, 1,4-diselenane-2,6-dithiol, 1,4-diselenane-2,6-dimercaptomethyl, 3,4-diaminoselenophane, 3,4-dihydroxyselenophane, 3,4-dimercaptoselenophane, 2,5-dimercaptomethylselenophane, 2,5-diselenomethylselenophane, 1,3-diselenocyclopentane-4,5-dithiol, 1,3-diselenocyclopentane-4,5-dimercaptomethyl, tricycloselenaoctane-3,6-dithio, tricycloselenaoctane-3,6-dimercaptomethyl, and tricycloselenaoctane-3,6-diselenol.

Further, halogen-substituted compounds such as a chlorine-substituted compound, bromine-substituted compound and the like, alkyl-substituted compounds, alkoxy-substituted compounds, nitro-substituted compounds of these compounds can also be used. These may be used alone or in combination of two or more.

The selenium atom-containing self-polymerizable compounds are compounds containing a selenium atom, having in the molecule at least any one self-polymerizable group selected from a (meth)acrylic group, allyl carbonate group, allyl thiocarbonate group, allyl selenocarbonate group, allyl group, vinyl group, isopropenyl group, epoxy group, and thioepoxy group, selenoepoxy group. Examples thereof include ethylene glycol diselenoglycidyl ether, 1,2-bis(3,4-episeleno-4-selanabutyl)ethane, xylylenedithiol diselenoglycidyl thioether, and 1,4-dithiane-2,5-dimercaptomethyl diselenoglycidyl thioether, and in addition, self-polymerizable compounds synthesized using the above-described active hydrogen compounds.

Further, halogen-substituted compounds such as a chlorine-substituted compound and bromine-substituted compound, alkyl-substituted compounds, alkoxy-substituted compounds, and nitro-substituted compounds of these compounds can also be used. These may be used alone or in combination of two or more.

The selenium atom-containing isocyanates are compounds containing a selenium atom, having in the molecule at least any one group selected from an isocyanate group, isothiocyanate group and isoselenocyanate group.

Examples thereof include 2,4-diselenapentane-1,5-di-iso(thio, seleno)cyanate, selenophane-2,5-di-iso(thio, seleno)cyanate, selenophane-2,5-di-iso(thio, seleno)cyanatomethyl, 1-thia-4-selenane-2,6-di-iso(thio, seleno)cyanate, 1-thia-4-selenane-2,6-di-iso(thio, seleno)cyanatomethyl, 1,4-diselenane-2,6-di-iso(thio, seleno)cyanate, 1,4-diselenane-2,6-di-iso(thio, seleno)cyanatomethyl, 1,3-diselenocyclopentane-4,5-di-iso(thio, seleno)cyanate, 1,3-diselenocyclopentane-4,5-di-iso(thio, seleno)cyanatomethyl, tricycloselenaoctane-3,6-di-iso(thio, seleno)cyanate, and tricycloselenaoctane-3,6-di-iso(thio, seleno)cyanatomethyl.

Further, halogen-substituted compounds such as a chlorine-substituted compound, bromine-substituted compound and the like, alkyl-substituted compounds, alkoxy-substituted compounds, nitro-substituted compounds, modified compounds in the form of a prepolymer with an active hydrogen compound, carbodiimide-modified compounds, urea-modified compounds, biuret modified compounds, and dimerized or trimerized reaction products of these compounds can also be used. These may be used alone or in combination of two or more.

The transparent optical material and plastic lens of the present invention can be usually obtained by casting polymerization.

Specifically, the above-described composition containing at least one reactive monomer or oligomer having at least one selenium atom is optionally defoamed by a suitable method such as reduction in pressure.

As other component than the reactive monomer or oligomer having a selenium atom, reactive monomers having the same properties are preferably used for the purpose of improving handling mainly in polymerizing a composition, improving polymerization property, modifying the resulting transparent optical material and plastic lens or the like, and other organic compounds and inorganic compounds can be added freely irrespective of the kind thereof in the range which is not problematical. For example, the other compound include also various substances such as an internal releasing agent, catalyst, chain extender, cross-linking agent, photo stabilizer, ultraviolet ray absorber, antioxidant, oil-soluble dye and filler according to the object, like known molding methods.

Then, this composition is subjected to casting polymerization. Namely, a composition is cast in a mold composed of a metal or a glass and a resin, and the composition is polymerized by heat and/or a radiation such as a light.

As reaction embodiments in the case of heat polymerization, there are listed for example a polymerization of only self-polymerizable compounds, polymerization of self-polymerizable compounds with active hydrogen compounds, polymerization of active hydrogen compounds with isocyanates, and polymerization in which they are combined.

Regarding polymerization conditions in the case of heat polymerization, for example, polymerization is conducted at a temperature of about −50° C. to 200° C. for 1 to 100 hours. Under these conditions, if polymerization is conducted with increasing the temperature gradually from lower temperature to higher temperature in the range from 10° C. to 150° C. for about 4 to 70 hours, preferable result is often obtained.

As reaction embodiments in the case of radiation polymerization, there are listed for example a polymerization of only self-polymerizable compounds, and polymerization of self-polymerizable compounds with active hydrogen compounds.

In the case of radiation polymerization, an ultraviolet ray or an visual light is preferably used as the radiation. Among them, there is preferably used a ultraviolet ray having a wavelength of 400 nm or less with which a sensitizer having high coloring ability represented by camphorquinone and the like is often dispensable.

The amount of a ultraviolet ray is not restricted since it differs significantly depending on the kind of a monomer and oligomer, and the ultraviolet ray is often irradiated at a strength of about 1 to 1000 mJ/sec for 1 to 7200 seconds, and in some cases, irradiated in several times or irradiated after cooling for the purposed of gradual heating.

Regarding the polymerization, heat polymerization may be combined with radiation polymerization without any problem.

However, the present invention is not limited to these polymerization embodiments and polymerization conditions.

Further, the polymerized molded article may optionally be subjected to annealing-treatment.

The resulting transparent optical material and plastic lens of the present invention can be subjected, if necessary, to physical or chemical treatments such as surface abrasion, antistatic treatment, hard coating treatment, anti-reflection coating treatment, dyeing treatment, and light control treatment, for effecting improvements such as prevention of reflection, imparting of high hardness, improvement of abrasion resistance, improvement in chemical resistance, imparting of antifogging property, or imparting of fashionable appearance.

The present inventors have found that refractive index can be further improved if a polymerizable compound having in the molecule a selenium atom is used, completing the present invention.

Namely, the present invention provides a selenium-containing alicyclic compound represented by formula (1):

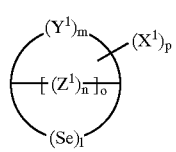

(1)

wherein $Y^1$ and $Z^1$ represent —$CH_2$—, =CH—, C atom, Se atom, S atom, $SO_2$, SO or O atom, and the hydrogen atom of methylene or methyne may also be substituted by a $C_1$ to $C_3$ lower alkyl group, $C_1$ to $C_3$ lower alkoxy group, $C_1$ to $C_3$ lower alkylthio group, F atom, Cl atom or Br atom; $X^1$ represents a functional group selected from a SH group, NCO group, NCS group, acryloyl group, methacryloyl group, vinyloxy group, vinylthio group, vinylseleno group, vinyl carbonate group, vinyl thiocarbonate group, vinyl selenocarbonate group, allyoxy group, allylthio group, allylseleno group, allyl carbonate group, allyl thiocarbonate group, allyl selenocarbonate group, isopropenyloxy group, isopropenylthio group, isopropenylseleno group, isopropenyl carbonate group, isopropenyl thiocarbonate group, isopropenyl selenocarbonate group, epoxy group and thioepoxy group, or an alkyl residue composed of such functional group and an alkylene group having 10 or less carbon atoms; l, m, n, o and p represent an integer of 1 to 5, 2 to 10, 0 to 5, 0 to 3 and 2 to 6, respectively, and a composition containing this selenium-containing alicyclic compound.

That is, the present invention provides a poly-functional compound containing at least a selenium atom in the aliphatic cyclic structure and having two or more of a mercapto group, iso(thio)cyanato group, (meth)acryloyl group, vinyl (allyl, isopropenyl) group and (thio)epoxy group, and a composition containing the same.

Such poly-functional compound and composition have not been known until now.

In the selenium-containing alicyclic compound of the present invention represented by the general formula (1), carbon atoms in the aliphatic cyclic structure are situated around the selenium-containing alicyclic structure substituted by one or more selenium atoms as a center structure.

This selenium-containing alicyclic structure is a aliphatic cyclic structure solely composed of single bonds, and may be composed of any number of atoms providing it is basically 3- or more-membered aliphatic cyclic structure, and 4 to 10-membered structure is relatively preferable and 5 to 9-membered structure is further preferable.

A part of the carbon atoms constituting the selenium-containing alicyclic structure may be substituted by a sulfur atom, sulfone, sulfoxy or oxygen atom other than selenium atom.

Further, a part or all of hydrogen atoms bonding to carbon atoms constituting the selenium-containing alicyclic structure may be substituted by one or more moieties selected from methyl, ethyl, propyl, methoxy, ethoxy, propoxy, methylthio, ethylthio, propylthio, methylseleno, ethylseleno, propylseleno, fluorine, chlorine and bromine.

Two or more polymerizable functional groups which are optionally connected to carbon atoms or alkyl residue constituting the selenium-containing alicyclic structure may be independently selected from one or more moieties selected from a SH group, NCO group and NCS group which effect addition polymerization, and an acryloyl group, methacryloyl group, vinyl group, allyl group, isopropenyl group, epoxy group and thioepoxy group which effect both addition polymerization and self polymerization.

The alkyl residue connected to a carbon atom constituting the selenium-containing alicyclic structure can have one or more of one or more kinds of the above-described functional groups.

The connected polymerizable functional groups or the alkyl residues having polymerizable functional groups may be composed of solely the same kinds of moiety or separately the different kinds of moieties without any problem.

Regarding connecting form to carbon atoms, one may be connected to one carbon atom, or two may be connected to the same carbon atom.

The alkyl residue explained in the present invention composed of the above-described polymerizable functional group and an alkylene group, and in this condition, the alkylene group may be a known alkylene group composed of only carbon atoms and hydrogen atoms, or may be an alkylene group of which part is substituted by one or more hetero atoms such as a selenium atom, sulfur atom, oxygen atom or the like.

The alkylene group is constituted of usually 10 or less carbon atoms, and preferably 0 to 6 carbon atoms and further preferably 0 to 4 carbon atoms.

The selenium-containing alicyclic poly-functional polymerizable compound (1) of the present invention is obtained, for example, by synthesizing a compound having selenium-containing alicyclic structure as a center skeleton using a selenium compound such as a selenium halide, alkaline metal selenide, alkaline metal selenol, alkyl(di)selenide, alkyl selenol, hydrogen selenide or the like, as described in literatures such as "The chemistry of selenium and tellurium compounds volume 1" (1986, Saul Patai and Zvi Roppoprt, John Wiley & Sons), "Selenium reagents and intermediates in organic synthesis" (1986, J. E. Baldwin, Pergamon Press), then, by. introducing a polymerizable reactive group such as a SH group, NCO group, NCS group, acryloyl group, methacryloyl group, vinyl group, allyl group, isopropenyl group, epoxy group and thioepoxy group by a known organic reaction as described in literatures such as "Synthetic organic chemistry" (1953, Romeo B. Wagner and Harry D. Zook, John Wiley & Sons).

Steps for producing a product are described by way of a specific example.

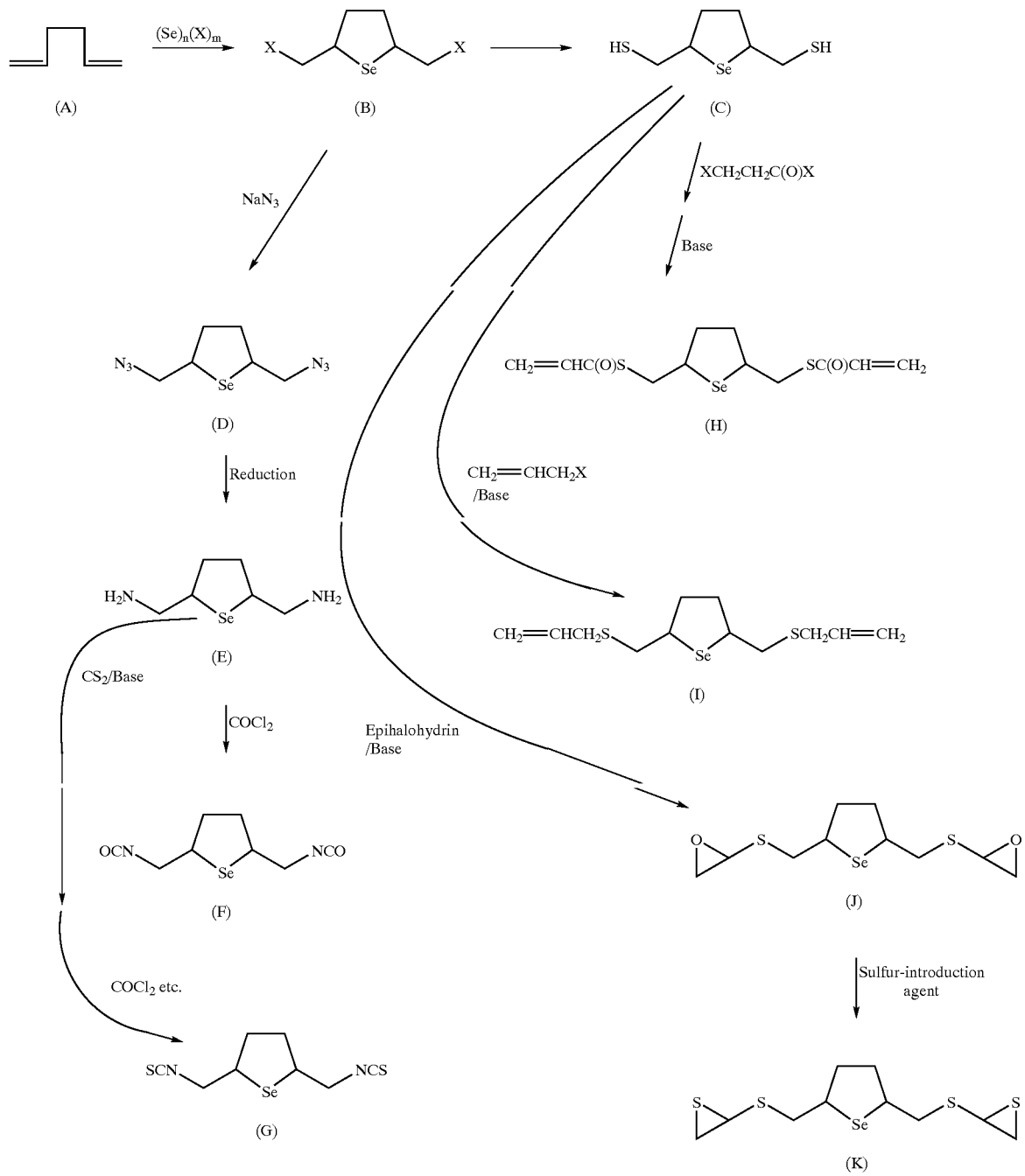

Hexadiene represented by formula (A) which is one of dienes is reacted with a selenium halide to synthesize a dihalogenomethylselenophane represented by formula (B). The selenium halide and the like used herein can be synthesized, for example, by a method described in a literature, "Handbook of preparative inorganic chemistry"

(volume 1, second edition, 1963, Georg Brauer, Academic Press), as well as other methods. Examples thereof include dichlorodiselenide, dibromodiselenide, tetrachloroselenium, tetrabromoselenium and seleniumoxychloride, and these can be suitably used in a ring-closing reaction and the like of a straight-chain diene.

They can also be used for an intermolecular polycyclization reaction with cyclohexadiene, cyclopentadiene, dicyclopentadiene, cyclooctadiene, thiophene and norbornanediene.

This ring-closing reaction and polycyclization reaction usually exhibits improved selectivity when conducted at a lower temperature of −70 to 0° C. At a temperature in the range from −50 to −20° C., more preferable results are often obtained. For further increasing selectivity, a method is effective in which either one of dienes or selenium halides are dropped into the reaction system, and if both of them are dropped simultaneously, the selectivity is further improved.

When a weak base such as sodium carbonate, sodium hydrogen carbonate, sodium acetate, potassium carbonate, calcium carbonate and the like is added in an amount in the range from 0.01 to 3 wt % based on the reaction solution for the purpose of increasing the reaction speed and completing the reaction, there are often obtained preferable results.

As other ring-closing reactions, there are listed, for example, a reaction of halogen compounds with an alkaline metal salt such as sodium selenol, sodium selenide and potassium selenide, a reactions of compounds having an electrophilic functional group such as ketone, acetaldehyde and acetal with diselenol, mercaptoselenol, and hydroxyselenol, as well as other reactions.

These ring-closing reaction are conducted at relatively high temperature range from 0 to 120° C. Though the reaction is possible at lower than 0° C., such temperature range is not practical since the reaction often progresses slowly.

On the other hand, when the reaction temperature is 120° C. or higher, the selectivity often decreases.

In a reaction using halogenated compounds are used, if a polar solvent such as water, methanol, isopropanol, acetone and N,N-dimethylformamide is used, preferable results are often obtained as compared with the case in which no solvent is used.

In a reaction using a ketone or aldehyde, further preferable results are often obtained if the reaction is conducted while conducting azeotropic dehydration using an azeotropic solvent such as dichloromethane, chloroform, dichloroethane, hexane, benzene and toluene, in the presence of a mineral acid such as hydrochloric acid, sulfuric acid and the like, Lewis acid such as dimethyltin oxide, dibutyltin oxide and metal tin, or an organic acid such as methanesulfonic acid and p-toluenesulfonic acid.

Dithiol compound (C) belonging to the polythiol compound of the present invention is obtained by substituting the halogen atom in formula (B) by a mercapto group. This substitution reaction can utilize various known reactions such as a method using thiourea, a method using alkaline metal hydrogen sulfides and alkaline metal sulfides such as sodium hydrogen sulfide, sodium sulfide and potassium hydrogen sulfide, a method using alkaline metal polysulfides such as sodium polysulfide and potassium polysulfide, a method using alkaline metal trithiocarbonates such as sodium trithiocarbonate and potassium trithiocarbonate, a method using potassium xanthate, a method using Bunte's salt, and the like.

For example, in the case of thiourea, thiourea and a known solvent such as water and alcohol are added to a dihalogenoselenophane (B) and the mixture is heated and stirred at a temperature in the range from 40 to 150° C., preferably from 60 to 120° C. for about 1 to 24 hours, preferably 1 to 8 hours to form a thiuronium salt. Then, to this is added a base such as sodium hydroxide and ammonia, and hydrolysis is conducted at a temperature in the range from 20 to 100° C., preferably from 40 to 60° C. for 1 to 10 hours, to obtain an intended dithiol compound (C).

As the base used in the hydrolysis, ammonia water is relatively preferable, and the amount of the base is from 1 to 5 equivalents, preferably from 1.1 to 2.0 equivalents based on halogen atom in the raw material.

The chain of the mercaptometyl group of formula (C) corresponding to the alkyl residue of formula (1) is extended as described below.

A dihalogenoselenophane (B) is reacted with hydroxyethylselenol formed from bromoethanol and sodiumselenol in the presence of a base such as sodium hydroxide and potassium hydroxide to synthesize bis(4-hydroxy-2-selenabutyl)selenophane.

The amount of the base is preferably from 1 to 2 equivalents, more preferably from 1 to 1.3 equivalents based on the hydroseleno group of the produced hydroxyethylselenol.

The reaction temperature is preferably from 0 to 50° C., further preferably from 10 to 40° C. Then, a mineral acid such as hydrochloric acid or hydrobromic acid is added in an amount in the range from 1 to 10 equivalents, preferably from 1.1 to 2 equivalents based on the hydroxy group of bis(4-hydroxy-2-selenabutyl)selenophane, and thiourea is reacted in the same manner as for the above-described thiuronium salt formation, then, hydrolysis is conducted, to obtain bis(4-mercapto-2-selenabutyl)selenophane in which the methylene group in formula (C) is extended to a selenabutylene group.

When a mineral acid is not used, the above-described bis(4-hydroxy-2-selenabutyl)selenophane is reacted with a halogenating agent such as phosphorus tribromide or thionyl chloride to synthesize a halogenated compound, then, bis (4-mercapto-2-selenabutyl)selenophane is synthesized in the same manner as for the dithiol compound of formula (C).

The amount of the halogenating agent is in the range from 1 to 3 equivalents, preferably from 1 to 2 equivalents based on the hydroxy group in the same way as above.

The reaction temperature is not particularly restricted since it differs significantly depending on the halogenating agent and the structure of a hydroxy compound to be halogenated, and is about from 0 to 200° C., and particularly from 10 to 120° C.

In the case of extension of an alkylene group composed only carbon atoms and hydrogen atoms, it may be advantageous that, for example, 3,6-dihalogenooctane-1,8-diol is reacted with sodium selenide to synthesize bis(2-hydroxyethyl)selenophane, then, the same manner as described above is conducted to form a dithiol.

When an alkylene group is removed and a reactive group is connected directly to a selenium-containing aliphatic ring, for example, butadiene is bubbled through a mixed solution of selenium dioxide with a hydrohalic acid such as hydrochloric acid and hydrobromic acid, to synthesize a 3,4-dihalogeno-selenophane, then, thiol-substitution reaction is conducted.

This ring-closing reaction is conducted at a temperature in the range from 0 to 100° C. which is higher than in the case of using selenium halides. The preferable range is from 50 to 80° C.

Though the reaction can be extremely satisfactorily conducted around 0 to 10° C., an intermediate compound in which further two halogen atoms are connected to a selenium atom in the selenophane skeleton remains in addition to the intended compound.

This intermediate compound can be easily converted to the intended compound by washing with a base such as sodium thiosulfate and aqueous ammonia, or by adding olefins such as butadiene at about 50° C. or higher and further reacting them, however, the operation becomes complicated. If the following reaction is a reaction under basic condition, the reacted mixture can be often used without removing the intermediate. However, usually the intended compound containing no intermediate compound is used.

When lower than 0° C., the reaction speed tends to become slow, and when not lower than 80° C., the selectivity tends to lower.

Thiol-substitution reaction often gives excellent result when alkaline metal trithiocarbonates are used, unlike usual case.

For example, the following procedure is conducted.

Butadiene is bubbled through a mixed solution of selenium dioxide with 35% hydrochloric acid at an internal temperature of 70° C., then, filtered to obtain a crystal of 3,4-dichloroselenophane. Then, sodium hydrogen sulfide, sodium trithiocarbonate synthesized from sodium hydroxide and carbon disulfide, and 2,4-dichloroselenophane are reacted at a temperature from about 0 to 200° C., preferably from 20 to 120° C. in a polar solvent such as water, methanol, isopropanol and dimethylformamide, then, the product is decomposed by adding a mineral acid such as hydrochloric acid and sulfuric acid at a temperature usually from 0 to 200° C., preferably from 5 to 100° C., and further, Béchamp reduction treatment is conducted if necessary, and distilled to obtain 3,4-dimercaptoselenophane.

Di-isocyanatomethylselenophane of formula (F) belonging to the polyisocyanate compound of the present invention can also be synthesized directly from a halogen compound of formula (B) using a metal isocyanate such as silver isocyanate, sodium isocyanate and potassium isocyanate, in many cases, this method is not a preferable method since it is disadvantageous in cost and the yield is extremely low.

As another method, there is a method in which the product is synthesized from corresponding carboxylic acid and carboxylate by utilizing a rearrangement reaction such as Curtius rearrangement though it is not described in the above-described reaction route. This method may not sometimes be recognized as safe since the reaction sometimes occurs sharply with generating a nitrogen gas steeply even at a temperature around room temperature which is relatively low temperature.

However, this method is often used when scale is small since an intended isocyanate is obtained relatively easily.

When the above-described rearrangement reaction is not utilized, a halogenated compound of formula (B) is first reacted with an alkaline metal azide compound such as sodium azide and potassium azide to synthesize an azide compound of formula (D).

The amount used of an alkaline metal azide compound is acid, a method using a phosphine and hydrochloric acid, a method using lithium aluminum hydride or sodium boron hydride and iodine, a method using hydrogen under an Adams catalyst, and the like.

For example, in the case of the Béchamp reduction method, a solvent may be used or not used, and when taking out of the product is conducted by extraction, it is more efficient to use previously a solvent such as benzene, toluene, xylene, chlorobenzene, chloroform, dichloroethane, hexane and cyclohexane, which separates from water.

Likewise, when a solvent which separates from water is used, preferable results are often obtained when the above-described surfactants are added as phase transfer catalysts.

The amount added of these surfactants is preferably from 0.001 to 20 wt %, further preferably from 0.01 to 10 wt % based on the total weight of the reaction mass.

The amount used of the metal such as iron, tin or zinc is preferably from 1 to 5 equivalents, further preferably from 1 to 3 equivalents based on an azide group.

The amount used of the hydrohalic acid is preferably from 1 to 10 equivalents, further preferably from 1 to 4 equivalents based on an azide group.

The reaction temperature is preferably from 0 to 200° C., further preferably from 20 to 120° C.

As other method for synthesizing an amine compound of formula (E), there is also a method in which the amine compound is directly synthesized from a halogen compound of formula (B) preferably from 1. to 5 equivalents, further preferably from 1 to 3 equivalents based on the halogen atom in formula (B).

The reaction system may be a single solvent system composed solely of a polar solvent such as water, methanol, ethanol, isopropanol, ethylene glycol, dimethylformamide and the like, or may be a mixed system composed of water and a solvent which separates from water, as exemplified by toluene and water.

When recovering the product is taken into consideration, the mixed solvent system is relatively more efficient.

In the case of the mixed solvent system, preferable results are often obtained when surfactants such as alcohols, quaternary alkylammonium salts, metal alkyl- or arylcarboxylates, metal alkyl or arylsulfonates, acidic alkyl- or arylphosphate and metal salts thereof are added as phase transfer catalysts. The amount added of these surfactants is preferably from 0.001 to 20 wt %, further preferably from 0.01 to 10 wt % based on the total amount of the reaction mass.

The reaction temperature when an azide compound is synthesized is preferably in the range from about −10 to 200° C., further preferably from 20 to 150° C.

Then, this azide compound is reduced to obtain an amine compound of formula (E).

For reduction of an azide compound to synthesize the amine compound of formula (E), there are often used, for example, a Béchamp reduction method using a metal such as iron, tin or zinc and a hydrohalic acid such as hydrochloric acid or hydrobromic For example, there are listed an ammonolysis method using ammonia and sodiumamide, a Gabriel method using potassium phthalic imide, a Délepine method using hexamethylenediamine, and the like, however, none of them is so preferable since the yield is often low.

2,6-di-isocyanatomethylselenophane of formula (F) belonging to the polyisocyanate compound of the present invention is usually obtained by reacting an amine compound of formula (E) with a phosgene.

As the phosgenating reaction of the amine compound of formula (E), any of a cool and heat two-stage method in which the amine compound is reacted with a phosgene at low temperature, then, phosgenation is further conducted at high temperature, and a hydrochloride method in which a hydrochloride is once synthesized using the amine compound and a hydrochloric acid gas, then, it is reacted with a phosgene, can be suitably used.

When these methods are strictly compared, although the hydrochloride method is somewhat complicated, no impurity is formed and the yield tends to be improved.

For example, the hydrochloride method is conducted as follows.

The amine compound of formula (E) is added to a solvent such as toluene, chlorobenzene, dichlorobenzene, trichlorobenzene and amyl acetate dropwise with vigorous stirring, and a hydrochloric acid gas is bubbled through the solvent simultaneously, to conduct hydrochloride formation.

The amount used of the hydrochloric acid gas for the bubbling is preferably from 1 to 5 equivalents, further preferably from 1 to 2 equivalents based on the amino group of the amine compound of formula (E).

The amount used of the solvent is preferably from 5 to 20-fold volume, further preferably from 7 to 15-fold volume based on the amine compound of formula (E).

The reaction temperature of the hydrochloride formation significantly differs depending on the solvent used, and preferably from about 0 to 200° C., further preferably from 10 to 180° C.

Subsequently, a phosgene is blown in the liquid of this reaction mass to conduct phosgenation, to obtain a polyisocyanate of formula (F).

The amount used of the phosgene is preferably from about 1 to 10 equivalents, further preferably from 2 to 4 equivalents based on the amino group of the amine compound of formula (E).

The reaction temperature is preferably from 120 to 200° C., further preferably from 130 to 180° C.

Di-isocyanatomethylselenophane of formula (G) belonging to the polyisothiocyanate of the present invention is also synthesized from the amine compound of formula (E).

For example, there are listed a method in which the amine compound of formula (E) is reacted with carbon disulfide, and a base such as sodium hydroxide, potassium hydroxide and ammonia, then, the product is decomposed by using a chlorinating agent such as phosgene, alkylchloroformate and sodium hypochlorite, a method in which a thiophosgene is reacted, and the like, and any of them can be suitably used.

The above-described method using carbon disulfide will be explained further in detail as follows.

The amine compound of formula (E) is added to a mixture of an aqueous sodium hydroxide solution and carbon disulfide dropwise to produce sodium dithiocarbamate.

The amount used of sodium hydroxide is preferably from 2 to 5 equivalents, further preferably from 2 to 3 equivalents based on the amino group in the amine compound of formula (E). The amount used of carbon disulfide is preferably from 1 to 4 equivalents, further preferably from 1 to 2 equivalents based on the same basis.

The reaction temperature is preferably in the range from −20 to 200°c, further preferably from 0 to 120° C.

Subsequently, water and a solvent which separates from water such as benzene, toluene, xyene, chlorobenzene, dichlorobenzene, hexane and cyclohexane are added to this reaction solution, and to this is added methylchloroformate dropwise, and condensation-decomposition reaction is conducted to obtain an intended poyisothiocyanate compound of formula (G).

The solvent herein used is not essential for the reaction since it is added for the purpose of improving stirring property of the reaction solution and realizing simultaneous extraction of the product.

The amount used of an alkylchloroformate represented by methylchloroformate is preferably from 1 to 4 equivalents, further preferably from 1 to 3 equivalents based on the amino group in the amine compound of formula (E).

The reaction temperature is preferably from 0 to 200° C., further preferably from 20 to 150° C.

The operation may be conducted in a two-stage method in which the dropping is conducted at relatively lower temperature range from 20 to 50° C., and the aging is conducted at higher temperature range from 50 to 2 00° C., or at higher temperature range from 50 to 150° C. from the initial dropping to the aging.

Diacryloylthiomethylselenophane of formula (H) belonging to the poly(meth)acrylate compound of the present invention is obtained from the polythiol of formula (C).

For example, there are listed a two-stage method in which a polythiol of formula (c) is reacted with halogenated acid halides such as. chloropropionic acid chloride to synthesize halogenated esters, then, dehydrohalogenation is conducted using a base such as triethylamine, pyridine, sodium hydroxide, potassium hydroxide and sodium methylate, a method in which acid chlorides such as (meth)acrylic acid chloride are reacted, and the like.

The former two-stage method is often excellent from the viewpoints of purity and yield.

In the two-stage method, the amount used of halogenated acid halide for synthesizing halogenated esters, is preferably from 1 to 2 equivalents, further preferably from 1 to 1.2 equivalents based on the mercapto group in the polythiol of formula (C).

The reaction temperature is preferably from 20 to 100° C., further preferably from 30 to 70° C. The reaction solvent may be used or not be used, and reaction speed is faster when it is not used.

A base such as triethylamine, pyridine, sodium hydroxide, potassium hydroxide and sodium methylate may be used or not be used as a hydrogen halide catching agent.

When an inert gas such as nitrogen is bubbled through the reaction system for the purpose of removing hydrogen halide, preferable results are often obtained.

The amount used of the base when dehydrohalogenation reaction is conducted using the same base as described above to obtain diacryloylthiomethylselenophane of formula (H) is preferably from 1 to 10 equivalents, further preferably from 1 to 3 equivalents based on the halogen atom in the halogenated esters synthesized above.

The reaction temperature is preferably from −10 to 100° C., further preferably from 0 to 50° C.

The reaction solvent may be used or not be used, and when used, it is efficient to use a solvent which separates from water such as benzene, toluene, xylene, chlorobenzene, hexane and cyclohexane when the product is taken out by extraction.

When polymethacryl compound is synthesized, 3-halogeno-2-methylpropionic acid halide or methacrylic acid halide may be advantageously used.

Diallylthiomethylselenophane of formula (I) belonging to the polyallyl compound of the present invention is obtained from the polythiol of formula (C) likewise.

Namely, allylhalides such as allyl chloride are reacted with the polythiol of formula (C) by dehydrohalogenation reaction using the same base as described above.

When a compound belonging to the polyvinyl compound of the present invention, for example, divinylthiomethylselenophane is synthesized, vinyl halides such as vinyl bromide may be advantageously used instead of allyl halides. Alternatively, acetylene may also be reacted.

In a like manner, when a compound belonging to the polyisopropenyl compound of the present invention, for example, di-isopropenylthiomethylselenophane is synthesized, isopropenyl halides such as isopropenyl chloride may be advantageously used instead of allyl halides.

Bis(glycidylthiomethyl)selenophane of formula (J) belonging to the polyepoxy compound of the present invention can be synthesized from the polythiol of formula (C) or the above-described polyallyl compounds.

As the method for using the polythiol of formula (C), for example, there are listed a two-stage method in which epihalohydrins such as epichlorohydrin and epibromohydrin are reacted to synthesize halogenated alcohol, then, dehydrohalogenation reaction is conducted using a base such as triethylamine, pyridine, sodium hydroxide, potassium hydroxide and sodium methylate, a method in the above-described halohydrins are reacted in one stage using the above-described base, and the like.

The former two-stage method is often excellent from the viewpoints of purity and yield.

In the two-stage method, the amount used of an epihalohydrin when epihalohydrins are reacted, is preferably from 1 to 5 equivalents, further preferably from 1 to 2 equivalents based on the mercapto group in the polythiol of formula (C).

The reaction temperature is preferably from 0 to 100° C., further preferably from 5 to 60° C.

When a base such as triethylamine, pyridine, sodium hydroxide, potassium hydroxide, sodium methylate and the like is added in an amount from 0.01 to 10%, preferably from 0.1 to 3% based on the total weight of the reaction mass for the purpose of improving the reaction speed, preferable results are often obtained.

The reaction solvent may be used or not be used, and when used, a solvent which separates from water such as benzene, toluene, xylene, chlorobenzene, hexane and cyclohexane is used, and further, surfactants such as alcohols, quaternary alkylammonium salts, metal alkyl- or arylcarboxylates, metal alkyl- or arylsulfonates, acidic alkyl- or arylphosphate and metal salts thereof may be added as phase transfer catalysts. Under such conditions, reaction results are excellent and recovery is also efficient in many cases.

The amount added of these surfactants is preferably from 0.001 to 20 wt %, further preferably from 0.01 to 10 wt % based on the total amount of the reaction mass.

Then, dehydrohalogenation reaction is conducted by adding a base such as triethylamine, pyridine, sodium hydroxide,. potassium hydroxide and sodium methylate, to the above-described reaction mass or taken out halogenated alcohols, to synthesize bis(glycidylthiomethyl)selenophane of formula (J).

The amount used of the base in this case is preferably from 1 to 5 equivalents, further preferably from 1 to 3 equivalents based on the halogen atom in the halogenated alcohols.

The reaction temperature is preferably from 0 to 100° C., further preferably from 5 to 50° C.

The reaction solvent may be used or not be used, and when used, it is efficient to use a solvent which separates from water such as benzene, toluene, xylene, chlorobenzene, hexane and cyclohexane since taking out by extraction is possible.

Like the above-described case, addition of a surfactant often gives preferable results.

As other method using the polyallyl compound, there are listed, like the method used for synthesis of propylene oxide, a method in which an allyl group is reacted with water and a halogen such as chlorine or bromine to synthesize halogenated alcohol, then, dehydrohalogenation reaction is conducted, a method in which an allyl group is reacted with a peroxide such as peroxybenzoic acid and the like to conduct direct oxidation and synthesis, and the like.

The direct oxidation method using a peroxide is not so preferable method since it is accompanied by crisis such as explosion and the like.

Bis (4,5-epithio-2-thiapentyl)selenophane of formula (K) belonging to the polythioepoxy compound of the present invention can be synthesized from the epoxy compound of formula (J), the same polyallyl compound as described above or the like.

The method using the epoxy compound of formula (J) is a method in which this epoxy compound is reacted with a sulfur-introducing agent represented by thiourea, or metal thiocyanates such as sodium thiocyanate and potassium thiocyanate.

The amount used of these thiation agents is preferably from 1 to 10 equivalents, further preferably from 1 to 4 equivalents based on the epoxy group in formula (J).

The reaction temperature is preferably from 0 to 120° C., further preferably from 10 to 70° C.

When thiourea is used as the thiation agent, addition of an acid such as acetic anhydride is effective for stabilization, and imparts preferable results in many cases.

The reaction solvent may be used or not be used, and when used, alcohols such as methanol, ethanol, isopropanol and glycerin, hydrocarbons such as benzene, toluene and xylene, halogenated hydrocarbons such as chloroform, dichloroethane and chlorobenzene, water, as well as other compound are preferably used. These solvents may be used alone or in combination of two or more to form a mixed solvent.

Like the above-described case, addition of a surfactant often gives preferable results.

The other method using a polyallyl compound include a method in which the polyallyl compound is reacted with a sulfur halide such as sulfur chloride and sulfur bromide, then, a reducing dehydrohalogenation reaction is conducted using sodium sulfide, sodium thiosulfate and the like, as well as other methods.

Even if the reducing dehydrohalogenation agent such as sodium sulfide and the like is not used, an intended thioepoxy compound may sometimes be obtained only by reacting a sulfur halide.

When acids such as sulfuric acid, phosphoric acid, hydrochloric acid, acetic anhydride, phthalic anhydride and the like are added for the purpose of improving stability in synthesis and storage of the thus obtained thioepoxy compound of formula (K), preferable results are often obtained.

The reaction solvent may be used or not be used, in synthesizing the compound (1) of the present invention also containing compounds represented by formulae (C), (F), (G), (H), (I), (J) and (K).

When the solvent is used, any solvent can be used selected from general solvents described in "Solvent Handbook" (Shozo Asahara et al., published by Kodansha Ltd.) providing it does not exert influence on the reaction, recovery, product, and the like.

Preferable solvents can not be particularly restricted since the reactions and conditions differ significantly. If restricting them, alcohols such as methanol, ethanol, isopropanol, ethylene glycol and ethylcellosolve; hydrocarbons such as benzene, toluene, xylene, hexane and cyclohexane; halogenated hydrocarbons such as dichloromethane, chloroform, dichloroethane, chlorobenzene, dichlorobenzene and trichlorobenzene; polar solvents such as acetonitrile, N,N-dimethylformamide, N,N-dimethylimidazolidinone, acetone and methyl isobutyl ketone; esters such as ethyl acetate, butyl acetate and amyl acetate; water, and the like are listed.

As the compounds of present invention having selenophane as the center skeleton of which synthesis methods are exemplified above, including compounds represented by formulae (C), (F), (G), (H), (I), (J) and (K), the following compounds are for example listed.

Examples of only typical compounds include 1,4-diselenane-(2,3 or 2,5 or 2,6)-dithiol, 1,4-diselenane-2,3,5, 6-tetrathiol, 1,4-diselenane-(2,3 or 2,5 or 2,6)-dimercaptomethyl, 1,4-diselenane-(2,3 or 2,5 or 2,6)-dimercaptoethyl, 1,4-diselenane-(2,3 or 2,5 or 2,6)-bis(4-mercapto-2-thiabutyl), 1,4-diselenane-(2,3 or 2,5 or 2,6)-bis (4-mercapto-2-selenabutyl), 1,4-diselenane-(2,3 or 2,5 or 2,6)-di-iso(thio)cyanate, 1,4-diselenane-(2,3 or 2,5 or 2,6)-di-iso(thio)cyanatomethyl, (2,3 or 2,5 or 2,6)-bis[(meth) acryloylthio]-1,4-diselenane, (2,3 or 2,5 or 2,6)-bis[(meth) acryloylseleno]-1,4-diselenane, (2,3 or 2,5 or 2,6)-bis [(meth)acryloyloxy]-1,4-diselenane, (2,3 or 2,5 or 2,6)-bis [(meth)acryloylthiomethyl]-1,4-diselenane, (2,3 or 2,5 or 2,6)-bis[(meth)acryloylselenomethyl]-1,4-diselenane, (2,3 or 2,5 or 2,6)-bis[(meth)acryloyloxymethyl]-1,4-diselenane, (2,3 or 2,5 or 2,6)-divinyl(or diallyl or di-isopropenyl)-1,4-diselenane, (2,3 or 2,5 or 2,6)-divinylthio(or diallylthio or di-isopropenylthio)-1,4-diselenane, (2,3 or 2,5 or 2,6)-divinylseleno(or diallylseleno or di-isopropenylseleno)-1,4-diselenane, (2,3 or 2,5 or 2,6)-divinylthiomethyl(or diallylthiomethyl or di-isopropenylthiomethyl)-1,4-diselenane, (2,3 or 2,5 or 2,6)-divinylselenomethyl(or diallylselenomethyl or di-isopropenylselenomethyl)-1,4-diselenane, (2,3 or 2,5 or 2,6)-bis[1,2-epoxyethyl(or 1,2-epithioethyl)]-1,4-diselenane, (2,3 or 2,5 or 2,6)-bis[1,2-epoxyethylthio(or 1,2-epoxyethylseleno)]-1,4-diselenane, (2,3 or 2,5 or 2,6)-bis[1,2-epithioethylthio(or 1,2-epithioethylseleno)]-1,4-diselenane, (2,3 or 2,5 or 2,6)-bis[1,2-epoxyethylthiomethyl (or 1,2-epithioethylthiomethyl)]-1,4-diselenane, (2,3 or 2,5 or 2,6)-bis[1,2-epoxyethylselenomethyl(or 1,2-epithioethylselenomethyl)]-1,4-diselenane, (2,3 or 2,5 or 2,6)-bis[2,3-epoxypropyl(or 2,3-epithiopropyl)]-1,4-diselenane, (2,3 or 2,5 or 2,6)-bis[3,4-epoxy-1-oxabutyl(or 3,4-epithio-1-oxa-butyl)]-1,4-diselenane, (2,3 or 2,5 or 2,6)-bis[3,4-epoxy-1-thiabutyl(or 3,4-epithio-1-thiabutyl)]-1,4-diselenane, (2,3 or 2,5 or 2,6)-bis[3,4-epoxy-1-selenabutyl (or 3,4-epithio-1-selenabutyl)]-1,4-diselenane, (2,3 or 2,5 or 2,6)-bis-[4,5-epoxy-2-oxapentyl(or 4,5-epithio-2-oxapentyl)]-1,4-diselenane, (2,3 or 2,5 or 2,6)-bis[4,5-epoxy-2-thiapentyl(or 4,5-epithio-2-thiapentyl)]-1,4-diselenane, (2,3 or 2,5 or 2,6)-bis[4,5-epoxy-2-selenapentyl (or 4,5-epithio-2-selenapentyl)]-1,4-diselenane, 1,3-diselenane-(2,4 or 2,5 or 5,6)-dithiol, 1,3-diselenane-2,4,5,6-tetrathiol, 1,3-diselenane-(2,4 or 2,5 or 5,6)-dimercaptomethyl 1,3-diselenane-(2,4 or 2,5 or 5,6)-dimercaptoethyl, 1,3-diselenane-(2,4 or 2,5 or 5,6)-bis-(4-mercapto-2-thiabutyl), 1 3-diselenane-(2,4 or 2,5 or 5,6)-bis-(4-mercapto-2-selenabutyl), 1,3-diselenane-(2,4 or 2,5 or 5,6)-di-iso(thio)cyanate, 1,3-diselenane-(2,4 or 2,5 or 5,6)-di-iso(thio)cyanatomethyl, (2,4 or 2,5 or 5,6)-bis [(meth)acryloylthio]-1,3-diselenane, (2,4 or 2,5 or 5,6)-bis [(meth)acryloylseleno]-1,3-diselenane, (2,4 or 2,5 or 5,6)-bis[(meth)acryloyloxy]-1,3-diselenane, (2,4 or 2,5 or 5,6)-bis[(meth)acryloylthiomethyl]-1,3-diselenane, (2,4 or 2,5 or 5,6)-bis[(meth)acryloylselenomethyl]-1,3-diselenane, (2,4 or 2,5 or 5,6)-bis[(meth)acryloyloxymethyl]-1,3-diselenane, (2,4 or 2,5 or 5,6)-divinyl(or diallyl or di-isopropenyl)-1,3-diselenane, (2,4 or 2,5 or 5,6)-divinylthio (or diallylthio or di-isopropenylthio)-1,3-diselenane, (2,4 or 2,5 or 5,6)-divinylseleno(or diallylseleno or di-isopropenylseleno)-1,3-diselenane, (2,4 or 2,5 or 5,6)-divinylthiomethyl(or diallylthiomethyl or di-isopropenylthiomethyl)-1,3-diselenane, (2,4 or 2,5 or 5,6)-divinylselenomethyl(or diallylselenomethyl or di-isopropenylselenomethyl)-1,3-diselenane, (2,4 or 2,5 or 5,6)-bis[2-epoxyethyl(or 1,2-epithioethyl)-3-diselenane, (2,4 or 2,5 or 5,6)-bis[1,2-epoxyethylthio(or 1,2-epoxyethylseleno)]-1,3-diselenane, (2,4 or 2,5 or 5,6)-bis[1,2-epithioethylthio(or 1,2-epithioethylseleno)]-1,3-diselenane, (2,4 or 2,5 or 5,6)-bis[1,2-epoxyethylthiomethyl (or 1,2-epithioethylthiomethyl)]-1,3-diselenane, (2,4 or 2,5 or 5,6)-bis[1,2-epoxyethylselenomethyl(or 1,2-epithioethylselenomethyl)]-1,3-diselenane, (2,4 or 2,5 or 5,6)-bis[2,4-epoxypropyl(or 2,4-epithiopropyl)]-1,3-diselenane, (2,4 or 2,5 or 5,6)-bis[3,4-epoxy-1-oxabutyl(or 3,4-epithio-1-oxabutyl)]-1,3-diselenane, (2,4 or 2,5 or 5,6)-bis[3,4-epoxy-1-thiabutyl(or 3,4-epithio-1-thiabutyl)]-1,3-diselenane, (2,4 or 2,5 or 5,6)-bis[3,4-epoxy-1-selenabutyl (or 3,4-epithio-1-selenabutyl)]-1,3-diselenane, (2,4 or 2,5 or 5,6)-bis[4,5-epoxy-2-oxapentyl(or 4,5-epithio-2-oxapentyl)]-1,3-diselenane, (2,4 or 2,5 or 5,6)-bis[4,5-epoxy-2-thiapentyl(or 4,5-epithio-2-thiapentyl)]-1,3-diselenane, (2,4 or 2,5 or 5,6)-bis[4,5-epoxy-2-selenapentyl (or 4,5-epithio-2-selenapentyl)]-1,3-diselenane, 1-thia-4-selenane-(2,3 or 2,5 or 2,6 or 3,5)-dithiol, 1-thia-4-selenane-2,3,5,6-tetrathiol, 1-thia-4-selenane-(2,3 or 2,5 or 2,6 or 3,5)-dimercaptomethyl, 1-thia-4-selenane-(2,3 or 2,5 or 2,6 or 3,5)-dimercaptoethyl, 1-thia-4-selenane-(2,3 or 2,5 or 2,6 or 3,5)-bis(4-mercapto-2-thiabutyl), 1-thia-4-selenane-(2,3 or 2,5 or 2,6 or 3,5)-bis(4-mercapto-2-selenabutyl), 1-thia-4-selenane-(2,3 or 2,5 or 2,6 or 3,5)-di-iso(thio)cyanate, 1-thia-4-selenane-(2,3 or 2,5 or 2,6 or 3,5)-di-iso(thio) cyanatomethyl, (2,3 or 2,5 or 2,6 or 3,5)-bis[(meth) acryloylthio]-1-thia-4-selenane, (2,3 or 2,5 or 2,6 or 3,5)-bis[(meth)acryloylseleno]-1-thia-4-selenane, (2,3 or 2,5 or 2,6 or 3,5)-bis[(meth)acryloyloxy]-1-thia-4-selenane, (2,3 or 2,5 or 2,6 or 3,5)-bis[(meth)acryloylthiomethyl]-1-thia-4-selenane, (2,3 or 2,5 or 2,6 or 3,5)-bis[(meth) acryloylselenomethyl]-1-thia-4-selenane, (2,3 or 2,5 or 2,6 or 3,5)-bis[(meth)acryloyloxymethyl]-1-thia-4-selenane, (2,3 or 2,5 or 2,6 or 3,5)-divinyl(or diallyl or di-isopropenyl)-1-thia-4-selenane, (2,3 or 2,5 or 2,6 or 3,5)-divinylthio(or diallylthio or di-isopropenylthio)-1-thia-4-selenane, (2,3 or 2,5 or 2,6 or 3,5)-divinylseleno(or diallylseleno or di-isopropenylseleno)-1-thia-4-selenane, (2,3 or 2,5 or 2,6 or 3,5)-divinylthiomethyl(or diallylthiomethyl or di-isopropenylthiomethyl)-1-thia-4-selenane, (2,3 or 2,5 or 2,6 or 3,5)-divinylselenomethyl(or diallylselenomethyl or di-isopropenylselenomethyl)-1-thia-4-selenane, (2,3 or 2,5 or 2,6 or 3,5)-bis[1,2-epoxyethyl(or 1,2-epithioethyl)]-1-thia-4-selenane, (2,3 or 2,5 or 2,6 or 3,5)-bis[1,2-epoxyethylthio(or 1,2-epithioethylseleno)]-1-thia-4-selenane, (2,3 or 2,5 or 2,6 or 3,5)-bis[1,2-epithioethylthio (or 1,2-epithioethylseleno)]-1-thia-4-selenane, (2,3 or 2,5 or 2,6 or 3,5)-bis[1,2-epoxyethylthiomethyl(or 1,2-epithioethylthiomethyl)]-1-thia-4-selenane, (2,3 or 2,5 or 2,6 or 3,5)-bis[1,2-epoxyethylselenomethyl(or 1,2-epithioethylselenomethyl)]-1-thia-4-selenane, (2,3 or 2,5 or 2,6 or 3,5)-bis[2,3-epoxypropyl(or 2,3-epithiopropyl)]-1-thia-4-selenane, (2,3 or 2,5 or 2,6 or 3,5)-bis[3,4-epoxy-1-oxabutyl(or 3,4-epithio-1-oxabutyl)]-1-thia-4-selenane, (2,3 or 2,5 or 2,6 or 3,5)-bis[3,4-epoxy-1-thiabutyl(or 3,4-epithio-1-thiabutyl)]-1-thia-4-selenane, (2,3 or 2,5 or 2,6 or 3,5)-bis[3,4-epoxy-1-selenabutyl(or 3,4-epithio-1-selenabutyl)]-1-thia-4-selenane, (2,3 or 2,5 or 2,6 or 3,5)-bis[4,5-epoxy-1-oxapentyl(or 4,5-epithio-1-oxapentyl)]-1-thia-4-selenane, (2,3 or 2,5 or 2,6 or 3,5)-bis[4,5-epoxy-2-thiapentyl(or 4,5-epithio-2-thiapentyl)]-1-thia-4-selenane, (2,3 or 2,5 or 2,6 or 3,5)-bis[4,5-epoxy-2-selenapentyl(or 4,5-epithio-2-selenapentyl)]-1-thia-4-selenane, dimercaptomethyl-1-thia-3-selenane, 1,3-diselenolane-(2,4 or 4,5)-dithiol, 1,3-diselenolane-214,5-trithiol, 2,4,5-trimercaptomethyl-1,3-diselenolane, 1,3-diselenolane-(2,4 or 4,5)-dimercaptomethyl, 1,3-diselenolane-(2,4 or 4,5)-dimercaptoethyl, 1,3-diselenolane-(2,4 or 4,5)-bis(4-mercapto-2-thiabutyl), 1,3-diselenolane-(2,4 or 4,5)- bis(4-mercapto-2-selenabutyl), 1,3-diselenolane-(2,4 or 4,5)-di-iso(thio)cyanate, 1,3-diselenolane-(2,4 or 4,5)-di-iso(thio)cyanatomethyl, (2,4 or 4,5)-bis[(meth)acryloylthio]-1,3-diselenolane, (2,4 or 4,5)-bis[(meth)acryloylseleno]-1,3-diselenolane, (2,4 or 4,5)-bis[(meth)acryloyloxy]-1,3-diselenolane, (2,4 or 4,5)-bis[(meth)acryloylthiomethyl]-1,3-diselenolane, (2,4 or 4,5)-bis[(meth)acryloylselenomethyl]-1,3-diselenolane, (2,4 or 4,5)-bis[(meth)acryloyloxymethyl]-1,3-diselenolane, (2,4 or 4,5)-divinyl(or diallyl or diidopropenyl)-1,3-diselenolane, (2,4 or 4,5)-divinylthio(or diallylthio or di-isopropenylthio)-1,3-diselenolane, (2,4 or 4,5)-divinylseleno(or diallylseleno or di-isopropenylseleno)-1,3-diselenolane, (2,4 or 4,5)-divinylthiomethyl(or diallylthiomethyl or di-isopropenylthiomethyl)-1,3-diselenolane, (2,4 or 4,5)-divinylselenomethyl(or diallylselenomethyl or di-isopropenylselenomethyl)-1,3-diselenolane, (2,4 or 4,5)-bis[1,2-epoxyethyl(or 1,2-epithioethyl)]-1,3-diselenolane, (2,4 or 4,5)-bis[1,2-epoxyethylthio(or 1,2-epoxyethylseleno)]-1,3-diselenolane, (2,4 or 4,5)-bis[1,2-epithioethylthio(or 1,2-epithioethylseleno)]-1,3-diselenolane, (2,4 or 4,5)-bis[1,2-epoxyethylthiorethyl(or 1,2-epithioethylthiomethyl)]-1,3-diselenolane, (2,4 or 4,5)-bis[1,2-epoxyethylselenomethyl(or 1,2-epithioethylselenomethyl)-1,3-diselenolane, (2,4 or 4,5)-bis[2,4-epoxypropyl(or 2,4-epithiopropyl)]-1,3-diselenolane, (2,4 or 4,5)-bis[3,4-epoxy-1-oxabutyl(or 3, 4-epithio-1-oxabutyl)]-1,3-diselenolane, (2,4 or 4,5)-bis[3,4-epoxy-1-thiabutyl(or 3,4-epithio-1-thiabutyl)]-1,3-diselenolane, (2,4 or 4,5)-bis-3,4-epoxy-1-selenabutyl (or 3,4-epithio-1-selenabutyl)]-1,3-diselenolane, (2,4 or 4,5)-bis[4,5-epoxy-2-oxapentyl(or 4,5-epithio-1-oxapentyl)]-1,3-diselenolane, (2,4 or 4,5)-bis[4,5-epoxy-2-thiapentyl(or 4,5-epithio-2-thiapentyl)]-1,3-diselenolane, (2,4 or 4,5)-bis[4,5-epoxy-2-selenapentyl(or 4,5-epithio-2-selenapentyl)]-1,3-diselenolane, 3,4-dimercaptomethyl-1,2-diselenolane, 1-thia-3-selanolane-(2,4 or 2,5 or 4,5)-dithiol, 1-thia-3-selenolane-2,4,5-trithiol, 2,4,5-trimercaptomethyl-1-thia-3-selanolane, 1-thia-3-selenolane-(2,4 or 2,5 or 4,5)-dimercaptomethyl, 1-thia-3-selenolane-(2,4 or 2,5 or 4,5)-dimercaptoethyl, 1-thia-3-selenolane-(2,4 or 2,5 or 4,5)-bis(4-mercapto-2-thiabutyl), 1-thia-3)selenolane-(2,4 or 2,5 or 4,5)-bis(4-mercapto-2-selenabutyl), 1-thia-3-selenolane-(2,4 or 2,5 or 4,5)-di-iso(thio)cyanate, 1-thia-3-selenolane-(2,4 or 2,5 or 4,5)-di-iso(thio)cyanatomethyl, (2,4 or 4,5)-bis[(meth)acryloylthio]-1-thia-3-selenolane, (2,4 or 2,5 or 4,5)-bis[(meth)acryloylseleno]-1-thia-3-selenolane, (2,4 or 2,5 or 4,5)-bis[(meth)acryloyloxy]-1-thia-3-selenolane, (2,4 or 2,5 or 4,5)-bis[(meth)acryloylthiomethyl]-1-thia-3-selenolane, (2,4 or 2,5 or 4,5)-bis[(meth)acryloylselenomethyl]-1-thia-3-selenolane, (2,4 or 2,5 or 4,5)-bis[(meth)acryloyloxymethyl]-1-thia-3-selenolane, (2,4 or 2,5 or 4,5)-divinyl(or diallyl or di-isopropenyl)-1-thia-3-selenolane, (2,4 or 2,5 or 4,5)-divinylthio(or diallylthio or di-isopropenylthio)-1-thia-3-selenolane, (2,4 or 2,5 or 4,5)-divinylseleno(or diallylseleno or di-isopropenylseleno)-1-thia-3-selenolane, (2,4 or 2,5 or 4,5)-divinylthiomethyl(or diallylthiomethyl or di-isopropenylthiomethyl)-1-thia-3-selenolane, (2,4 or 2,5 or 4,5)-divinylselenomethyl(or diallylselenomethyl or di-isopropenylselenomethyl)-1-thia-3-selenolane, (2,4 or 2,5 or 4,5)-bis[1,2-epoxyethyl(or 1,2-epithioethyl]-1-thia-3-selanolane, (2,4 or 2,5 or 4,5)-bis[1,2-epoxyethylthio(or 1,2-epoxyethylseleno)]-1-thia-3-selenolane, (2,4 or 2,5 or 4,5)-bis[1,2-epithioethylthio(or 1,2-epithioethylseleno)]-1-thia-3-selenolane, (2,4 or 2,5 or 4,5)-bis[1,2-epoxyethylthiomethyl(or 1,2-epithioethylmethyl)]-1-thia-3-selenolane, (2,4 or 2,5 or 4,5)-bis[1,2-epoxyethylselenomethyl(or 1,2-epithioethylselenomethyl)]-1-thia-3-selenolane, (2,4 or 2,5 or 4,5)-bis[2,4-epoxypropyl(or 2,4-epithiopropyl)]-1-thia-3-selenolane, (2,4 or 2,5 or 4,5)-bis[3,4-epoxy-1-oxabutyl(or 3,4-epithio-1-oxabutyl)]-1-thia-3-selenolane, (2,4 or 2,5 or 4,5)-bis[3,4-epoxy-1-thiabutyl(or 3,4-epithio-1-thiabutyl)]-1-thia-3-selenolane, (2,4 or 2,5 or 4,5)-bis[3,4-epoxy-1-selenabutyl(or 3,4-epithio-1-selenabutyl)]-1-thia-3-selenolane, (2,4 or 2,5 or 4,5)-bis[4,5-epoxy-2-oxapentyl(or 4,5-epithio-2-oxapentyl)]-1-thia-3-selenolane, (2,4 or 2,5 or 4,5bis[4,5-epoxy-2-thiapentyl (or 4,5-epithio-2-thiapentyl)]-1-thia-3-selenolane, (2,4 or 2,5 or 4,5)-bis[4,5-epoxy-2-selenapentyl(or 4,5-epithio-2-selenapentyl)]-1-thia-3-selenolane, 3,5-dimercaptomethyl-1-thia-2-selenolane, 2,4,6-trimercaptomethyl-1,3,5-triselenane, 2,6-dimercaptomethyl-1,3,5-triselenane, 2,6-di-iso(thio)cyanatomethyl-1,3,5-triselenane, 2,6-di(meth)acryloylthiomethyl-1,3,5-triselenane, 2,6-bis[4,5-epithio-2-thiapentyl(or 4,5-epoxy-2-thiapentyl)]-1,3,5-triselenane, 2,6-diallylthiomethyl-1,3,5-triselenane, tricycloselenaoctane diiso(thio)cyanate, tricycloselenaoctane dithiol, bis (meth)acryloylthio tricycloselenaoctane, bis[(meth)acryloyloxy] tricycloselenaoctane, bis[3,4-epithio-1-thiabutyl(or 3,4-epoxy-1-thiabutyl)]-tricycloselenaoctane, bis[3,4-epthio-1-oxabutyl(or 3,4-epoxy-1-oxabutyl)] tricycloselenaoctane, tricyclodiselenaoctane diiso(thio)cyanate, tricyclodiselenaoctane dithiol, tricyclotriselenaoctane di-iso(thio)cyanate, tricyclotriselenaoctane dithiol, tricyclothiaselenaoctane diiso(thio)cyanate, tricyclothiaselenaoctane dithiol, tricyclodithiaselenaoctane diiso(thio)cyanate, tricyclodithiaselenaoctane dithiol, dicyclodiselenahexane diiso (thio)cyanate, dicyclodiselenahexane dithiol, dicyclothiaselenahexane di-iso(thio)cyanate, dicyclothiaselenahexane dithiol, cyclo-1-thia-3-selenabutane-2,4-di-iso(thio)cyanatomethyl, cyclo-1-thia-3-selenabutane-2,4-dimercaptomethyl, cyclo-1-sulfo-3-selenabutane-2,4-di-iso(thio)cyanatomethyl, cyclo-1-sulfo-3-selenabutane-2,4-dimercaptomethyl, cyclo-1,3-diselenabutane-2,4-di-iso(thio) cyanatomethyl, cyclo-1,3-diselenabutane-2,4-dimercaptomethyl, cyclo-1,2-diselenabutane-2,4-di-iso(thio)cyanatomethyl, cyclo-1,2-diselenabutane-2,4-dimercaptomethyl, dicycloselenanonane diiso(thio)cyanate, dicycloselenanonane dithiol, dicycloselenanonane trithiol, dicycloselenanonane tetrathiol, dicycloselenanonane pentathiol, dicycloselenanonane hexathiol, bis[(meth)acryloylthio]-dicycloselenanonane, bis[(meth)acryloyloxy]-dicycloselenanonane, bis[3,4-epithio-1-thiabutyl(or 3,4-epoxy-1-thiabutyl)] dicycloselenanonane, bis[3,4-epithio-1-oxabutyl(or 3,4-epoxy-1-oxabutyl)]dicycloselenanonane, bis (allylthio)dicycloselenanonane, selenophane-(2,3 or 2,4 or 2,5 or 3,4)-dithiol, selenophane-2,3,4,5-tetrathiol, selenophane-(2,3 or 2,4 or 2,5 or 3,4)-dimercaptomethyl, selenophane-(2,3 or 2,4 or 2,5 or 3,4)-dimercaptoethyl, selenophane-(2,3 or 2,4 or 2,5 or 3,4)-bis(3-mercapto-1-thiapropyl), selenophane-(2,3 or 2,4 or 2,5 or 3,4)-bis(4-mercapto-2-thiabutyl), selenophane-(2,3 or 2,4 or 2,5 or 3,4)-bis(4-mercapto-2-thiapentyl), selenophane-(2,3 or 2,4 or 2,5 or 3,4)-bis(4-mercapto-2-selenabutyl), selenophane-(2,3 or 2,4 or 2,5 or 3,4)-di-iso(thio)cyanate, selenophane-(2,3 or 2,4 or 2,5 or 3,4)-di-iso(thio)cyanatomethyl, (2,3 or 2,4 or 2,5 or 3,4)-bis[(meth)acryloylthio]-selenophane, (2,3 or 2,4 or 2,5 or 3,4)-bis[(meth)acryloylseleno]-selenophane, (2,3 or 2,4 or 2,5 or 3,4)-bis[(meth)acryloyloxy]-selenophane, (2,3 or 2,4 or 2,5 or 3,4)-bis[(meth)acryloylthiomethyl]-selenophane, (2,3 or 2,4 or 2,5 or 3,4)-bis[4-(meth)acryloylthio-2-thiabutyl]-selenophane, (2,3 or 2,4 or 2,5 or 3,4)-bis[5-(meth)acryloylthio-2-thiapentyl]-selenophane, (2,3 or 2,4 or 2,5 or 3,4)-bis[4-(meth)acryloylthio-2-selenabutyl]-selenophane, (2,3 or 2,4 or 2,5 or 3,4)-bis[7-(meth)acryloylthio-2,5-dithiaheptyl]-selenophane, (2,3 or 2,4 or 2,5 or 3,4)-bis[13-(meth)acryloylthio-2,6,10-trithiatridecyl]-selenophane, (2,3 or 2,4 or 2,5 or 3,4)-bis[(meth)acryloylselenomethyl]-selenophane, (2,3 or 2,4 or 2,5 or 3,4)-bis[4-(meth)acryloylselena-2-selenabutyl]selenophane, (2,3 or 2,4 or 2,5 or 3,4)-bis[(meth)acryloyloxymethyl]-selenophane, (2,3 or 2,4 or 2,5 or 3,4)-bis(vinyl carbonate or allyl carbonate or isopropenyl carbonate)selenophane, (2,3 or 2,4 or 2,5 or 3,4)-bis(vinyl thiocarbonate or allyl thiocarbonate or isopropenyl thiocarbonate)selenophane, (2,3 or 2,4 or 2,5 or 3,4)-bis(vinyl selenocarbonate or allyl selenocarbonate or isopropenyl selenocarbonate)selenophane, (2,3 or 2,4 or 2,5 or 3,4)-divinylthio(diallylthio or di-isopropenylthio)selenophane, (2,3 or 2,4 or 2,5 or 3,4)-divinylseleno(diallylseleno or di-isopropenylseleno)selenophane, (2,3 or 2,4 or 2,5 or 3,4)-divinylthiomethyl(diallylthiomethyl or di-isopropenylthiomethyl)selenophane, (2,3 or 2,4 or 2,5 or 3,4)-divinylselenomethyl(diallylselenomethyl or di-isoprbpenylselenomethyl)selenophane, (2,3 or 2,4 or 2,5 or 3,4)-bis[1,2-epoxyethyl(or 1,2-epithioethyl)]selenophane, (2,3 or 2,4 or 2,5 or 3,4)-bis[1,2-epoxyethylthio(or 1,2-epithioethylseleno)]selenophane, (2,3 or 2,4 or 2,5 or 3,4 )-bis[1,2-epithioethylthio(or 1,2-epithioethylseleno)]selenophane, (2,3 or 2,4 or 2,5 or 3,4)-bis[1,2-epithioethylthiomethyl(or 1,2-epoxyethylthiomethyl)]selenophane, (2,3 or 2,4 or 2,5 or 3,4)-bis[1,2-epithioethylselenomethyl(or 1,2-epoxyethylselenomethyl)]selenophane, (2,3 or 2,4 or 2,5 or 3,4)-bis[2,3-epithiopropyl(or 2,3-epoxypropyl)]selenophane, (2,3 or 2,4 or 2,5 or 3,4)-bis[3,4-epithio-1-oxabutyl(or 3,4-epoxy-1-oxabutyl)]selenophane, (2,3 or 2,4 or 2,5 or 3,4)-bis[3,4-epithio-1-thiabutyl(or 3,4-epoxy-1-thiabutyl)]selenophane, (2,3 or 2,4 or 2,5 or 3,4)-bis[3,4-epithio-1-selenabutyl(or 3,4-epoxy-1-selenabutyl)]selenophane, (2,3 or 2,4 or 2,5 or 3,4)-bis[4,5-epithio-2-oxapentyl(or 4,5-epoxy-2-oxapentyl)]selenophane, (2,3 or 2,4 or 2,5 or 3,4)-bis[4,5-epithio-2-thiapentyl(or 4,5-epoxy-2-thiapentyl)]selenophane, (2,3 or 2,4 or 2,5 or 3,4)-bis[4,5-epithio-2-selenapentyl(or 4,5-epoxy-2-selenapentyl)]selenophane, 2-mercaptomethyl-5-mercapto-1-selenacyclohexane, 2-(4-mercapto-2-thiabutyl)-5-(3-mercapto-1-thiapropyl)-1-selenacyclohexane, 2-(4-mercapto-2-selenabutyl)-5-(3-mercapto-1-selenapropyl)-1-selenacyclohexane, 2-iso(thio)cyanatomethyl-5-iso(thio)cyanato-1-selenacyclohexane, 2-(meth)acryloylthiomethyl-5-(meth)acryloylthio-1-selenacyclohexane, 2-14-(meth)acryloylthio-2-thiabutyl]-5-[3-(meth)acryloylthio-1-thiapropyl]-1-selenacyclohexane, 2-[5-(meth)acryloylthio-2-thiapentyl]-5-[3-(meth)acryloylthio-1-thiabutyl]-1-selenacyclohexane, 2-(4,5-thioepoxy-2-thiapentyl)-5-(3,4-thioepoxy-1-thiabutyl)-1-selenacyclohexane, 2-(4,5-epoxy-2-thiapentyl)-5-(3,4-epoxy-1-thiabutyl)-1-thiacyclohexane, 1-selenacyclohexane-(2,3 or 2,4-or 2,5 or 2,6 or 3,4 or 3,5 or 4,5)-dithiol, trimercapto-1-selenacyclohexane, trimercaptomethyl-1-selenacyclohexane, (2,3 or 2,4 or 2,5 or 2,6 or 3,4 or 3,5 or 4,5)-dimercaptomethyl-1-selenacycohexane, 1-selenacyclohexane-(2,3 or 2,4 or 2,5 or 2,6 or 3,4 or 3,5 or 4,5)-di-iso(thio)cyanate, (2,3 or 2,4 or 2,5 or 2,6 or 3,4 or 3,5 or 4,5)-di-iso(thio)cyanatomethyl-1-selenacyclohexane, (2,3 or 2,4 or 2,5 or 2,6 or 3,4 or 3,5 or 4,5)-bis[(meth)acryloylthio]-1-selenacycyclohexane, (2,3 or 2,4 or 2,5 or 2,6 or 3,4 or 3,5 or 4,5)-bis[(meth)acryloylthiomethyl]-1-selenacyclohexane, (2,3 or 2,4 or 2,5 or 2,6 or 3,4 or 3,5 or 4,5)-bis[3-(meth)acryloylthio-1-thiapropyl]-1-selenacyclohexane, (2,3 or 2,4 or 2,5 or 2,6 or 3,4 or 3,5 or 4,5)-bis[3,4-thioepoxy-1-thiabutyl]-1-selenacyclohexane, (2,3 or 2,4 or 2,5 or 2,6 or 3,4 or 3,5 or 4,5)-bis[3,4-epoxy-1-thiabutyl]-1-selenacyclohexane, (2,3 or 2,4 or 2,5 or 2,6 or 3,4 or 3,5 or 4,5)-bis[4, 5-thioepoxy-2-thiapentyl]-1-selenacyclohexane, (2,3 or 2,4 or 2,5 or 2,6 or 3,4 or 3,5 or 4,5)-bis[4,5-epoxy-2-thiapentyl]-1-selenacyclohexane, and the like. These may be used alone or in combination of two or more.

Naturally, the present invention is not limited to these listed compounds.

The composition of the present invention essentially contains at least a di- or more-functional polymerizable compound represented by formula (1).

In addition to the di- or more-functional polymerizable compound represented by formula (1) of the present invention, other organic compounds and inorganic compounds such as oligomers such as a dimer, trimer and tetramer thereof and a prepolymer thereof, mono-functional compounds represented by formula (1) wherein p=1, polymerization inhibitor, resin modifier, additives, solvent used for synthesis, raw materials, and, by-products and impurities may also be contained.

The above-described resin modifier is used for the purpose of improving physical properties of the resin obtained by polymerization, and for example, mercapto compounds other than those represented by formula (1), iso(thio)cyanate compounds other than those represented by formula (1), (meth)acrylate compounds other than those represented by formula (1), allyl. (vinyl, isopropenyl) compounds other than those represented by formula (1), (thio)epoxy compounds other than those represented by formula (1), carboxylic acids and carboxylic anhydrides, mercaptocarboxylic acids, hydroxy compounds, amino acids and mercaptoamines, amines and the like are listed, and they can be added in the range which is not problematical until necessary physical properties are obtained.

Specific examples of the resin modifier include, are not limited to, mercapto compounds such as ethanedithiol, bis (2-mercaptoethyl)sulfide, 2,3-dimercapto-1-propanol, 1,2,3-trimercaptopropane, pentaerythritoltetrakis(2-mercaptothioglycolate), pentaerythritoltetrakis(3- mercaptopropionate), trimethylolpropanetris(2-mercaptothioglycolate), trimethylolpropanetris(3-mercaptopropionate), 2,5-bis(mercaptomethyl)thiophane, 1,4-dithiane-2,5-dimercaptomethyl, 2,3-bis(2-mercaptoethylthio)-1-propanethiol and bis (mercaptomethyl)-3,6,9-trithia-1,11-undecanedithiol; iso (thio)cyanates such as cyclohexylisocyanate, cyclohexylisothiocyanate, xylylene di-isocyanate, α,α',α'',α'''-tetramethylxylylene di-isocyanate, 3-isopropenyl-α,α'-dimethylbenzylisocyanate, hexamethylene di-isocyanate, trimethylhexamethylene di-isocyanate, isophorone di-isocyanate, dicyclohexylmethane di-isocyanate, 1,3-bis(isocyanatomethyl)cyclohexane and bis(isocyanatomethyl)norbornane; (meth)acrylates such as methyl methacrylate, ethylene glycol dimethacrylate, neopentyl glycol diacrylate, bis(methacryloylmethyl)norbornene, bis(acryloylethoxyethyl)bisphenol F, bis(methacryloyloethoxyethyl)bisphenol F, bis(acryloylethoxyethyl)bisphenol A, bis(methacryloylethoxyethyl)bisphenol A, glycerine dimethacrylate, trimethylolpropanetris(acrylate), trimethylolpropanetris(methacrylate), pentaerythritoltris(acrylate), pentaerythritoltetrakis(acrylate) and 2,5-bis(methacryloylthiomethyl)-1,4-dithiane; allyl(vinyl, isopropenyl) compounds such as acrylonitrile, butadiene, styrene, divinylbenzene, di-isopropenylbenzene and diethylene glycol bis(allyl carbonate); (thio)epoxy compounds such as bis(3-epithiopropyl)sulfide, 1,2-bis(3-epithiopropylthio)ethane, 1,2-bis(3-epithiopropylthioethylthio)-3-(3-epithiopropylthio)propane, vinylcyclohexane diepoxide, bisphenol A diglycidyl ether, 3,4-epoxycyclohexylmethyl-3',4'-epoxycyclohexane carboxylate and 1,2-hexahydrophthalic acid diglycidyl ester; carboxylic acids and carboxylic anhydrides such as phthalic acid, phthalic anhydride, hexahydrophthalic anhydride, methylhexahydrophthalic anhydride, maleic anhydride, trimellitic anhydride and pyromellitic anhydride; mercaptocarboxylic acids such as thioglycolic acid, 3-mercaptopropionic acid, thiobutyric acid, thiomalic acid and thiosalicylic acid; mercaptocarboxylic acids such as thiodiglycolic acid, thiodipropionic acid and dithiodipropionic acid; hydroxy compounds such a glycerine, polyethylene glycol, polypropylene glycol, butane diol, butyric acid and polybutyric acid; amino acids and mercaptoamines such as aspartic acid, alanine, b-alanine, glycine, taurine, cysteine, cysteamine and aminobenzoic acid; and amines such as hexamethylenediamine, isophoronediamine, bis(4-aminocyclohexyl)methane, 1,3-bis(aminomethyl)cyclohexane, bis(aminomethyl)norbornane, m-xylylenediamine and m-phenylenediamine.

These resin modifiers may be previously added in the reaction system or added in taking out process providing there is no problem.

Further, these resin modifiers may be added after the di- or more-functional polymerizable compound or the composition containing the same of the present invention is taken out as a product, as represented by compounding and the like in polymerization work. These resin modifiers may be used alone or in combination of two or more.

The resin and plastic lens obtained by the present invention are usually obtained by a casting polymerization method in which the di- or more-functional polymerizable compound represented by formula (1) and the composition containing the same are optionally defoamed by a suitable method such as stirring under reduced pressure and the like, then, the defoamed solution is poured into a mold composed of a metal or a glass and resins, then, polymerization is conducted by heat and/or a radiation such as a light and the like.

The molding can be possible by a reactive injection molding method used for molding of a known epoxy resin and large scale urethane resin, however, this method is not so often used as a method for producing a plastic lens which is required to have strict optical uniformity since the resulting molded article tends to have optical strain.

In conducting casting polymerization, a curing catalyst is preferably used for the purpose of shortening polymerization time, and the like.

Though the kind of the curing catalyst is not restricted since the nature thereof significantly differs depending of the kind of a reaction group to be polymerized, if mentioned, amines, phosphines, Lewis acids, radical polymerization catalysts, cationic polymerization catalysts and the like are listed.

Examples thereof include, but are not limited to, amines such as ethylamine, 2-aminoethanol, 4,4'-diaminodiphenylmethane, dibutylamine, triethylamine, tributylamine, 2-triethylenediamine, N,N-diethylaminoethanol, N,N-dimethylcyclohexylamine, N-methylmorpholine, piperidine, pyridine, β-picoline, 2-methylimidazole, dicyandiamide, hydrazide succinate, diaminomaleonitrile, diallylmelanine, aniline.phenylphosphonic acid salt, ethylenediamine.phenylphosphoric acid salt, boron tetrafluoride.monoethylamine salt, boron trifluoride.monoethylamine complex, phosphorus pentafluoride.isopropylamine complex, arsenic pentafluoride.laurylamine complex and antimony pentafluoride.benzylamine complex; phosphines such as trimethylphosphine, triethylphosphine, tripropylphosphine, tributylphosphine, tricyclohexylphosphine, tribenzylphosphine, triphenylphosphine, 1,2-bis(dimethylphosphino)ethane and 1,2-bis(diphenyl phosphino)ethane; Lewis acids such as dimethyltin dichloride, dimethyltin oxide, tetrachlorotin, monobutyltin trichloride, dibutyltin dichloride, tributyltin monochloride, tetrabutyltin, dibutyltin oxide, dibutyltin dilaurate, dibutyltin octanoate, tin stearate, zinc chloride, zinc acetylacetonate, aluminum fluoride, aluminum chloride, triphenylaluminum, tetraisopropoxytitanium, tetrabutoxytitanium, tetrachlorotitanium and calcium acetate; radical polymerization catalysts such as di-isopropyl peroxydicarbonate, di-sec-butyl peroxydicarbonate, acetylacetone peroxide, cumene hydroperoxide, t-butyl hydroperoxide, isobutyl peroxide, t-butylcumyl peroxide, 1,1-di-t-butyl peroxycyclohexane, 1,1,3,3-tetramethylbutyl peroxyneodecanoate, t-butyl peroxybenzoate, 2,2'-azobis(4-methoxy-2,4-dimethylvaleronitrile), 2,2'-azobis(2-cyclopropylpropionitrile), 2,2'-azobis(2,4-dimethylvaleronitrile), t-butyl peroxy-2-ethyl hexanoate, n-butyl-4,4'-bis(t-butyl peroxy)valerate and t-butyl peroxybenzoate; cationic polymerization catalysts such as diphenyliodonium hexafluorophorphoric acid, diphenyliodonium hexafluoroarsenic acid, diphenyliodonium hexafluoroantimony, triphenylsulfonium tetrafluoroboric acid, triphenylsulfonium hexafluorophosphoric acid and triphenylsulfonium hexafluoroarsenic acid; as well as other compounds.

These may be used alone or in combination of two or more.

When the curing catalyst is used, the amount used thereof is in the range from 0.001 to 10 wt %, preferably from 0.01 to 5 wt % based on the total amount of the di- or more-functional polymerizable compound or the composition containing the same of the present invention. When the amount used is less than 0.01 wt %, the effect is low, and when over 10 wt %, the use of the catalyst is not impossible, however, disadvantages may sometimes occur such as shortening of pot life, reduction in transparency, optical properties, weatherability or the like.

In addition to the curing catalyst, known various additives such as an internal releasing agent, optical stabilizer, ultraviolet ray absorber, antioxidant, oil-soluble dye, filler and the like may be added according to the object in the range which is not problematical.

The polymerization conditions in the case of heat polymerization are not restricted since they differ depending on the kinds of the di- or more-functional polymerizable compound and the composition thereof of the present invention, resin modifier and curing catalyst, the form of a mold, and the like, and the heat polymerization is conducted at a temperature of about −50 to 200° C. in the period of from 1 to 100 hours.

Depending on the occasion, preferable results may be imparted when polymerization is conducted for 4 to 70 hours while gradually increasing the temperature in the range from 10° C. to 150° C.

The polymerization conditions in the case of radiation polymerization are as described below.

As the radiation, a ultraviolet ray or a visual light is preferably used, among. them, there is preferably used a ultraviolet ray having a wavelength of 400 nm or less with which sensitizer having high coloring ability represented by camphorquinone is often dispensable.

The quantity of the ultraviolet ray is not restricted like the case of heat polymerization since it differs depending on the kinds of the di- or more-functional polymerizable compound and the composition thereof of the present invention, resin modifier and curing catalyst, the form of a mold, and the like, and the ultraviolet ray is often irradiated at a strength of about 1 to 1000 mJ/sec for 1 to 7200 seconds, and in some cases, irradiated in several times or irradiated after cooling for the purposed of gradual heating.

Regarding the polymerization, heat polymerization may be combined with radiation polymerization without any problem.

However, the present invention is not limited to. these polymerization embodiments and polymerization conditions.

Further, the polymerized molded article and plastic lens may optionally be subjected to annealing treatment.

The resulted molded article and plastic lens of the present invention can be subjected, if necessary, to physical or chemical treatments such as surface abrasion, antistatic treatment, hard coating treatment, anti-reflection coating treatment, dyeing treatment and light control treatment, for effecting prevention of reflection, imparting of high hardness, improvement in chemical resistance, imparting of antifogging property, imparting of fashionable appearance or the like.

An object of the present invention is to provide a material and a method which can fully satisfy requirements that the refractive index of a lens is further increased and the edge thickness of the lens is decreased.

The present inventors have intensively studied, and as. a result, found that refractive index can be improved if a tri- or more-functional polythiol having in the molecule a selenium atom is used, completing the present invention.

Namely, the present invention provide a tri- or more-functional selenium-containing polythiol represented by formula (2):

$$(Z^2)_q-(SH)_r \qquad (2)$$

wherein, $Z^2$ represents an alkylene group having at least one Se atom, q represents an integer from 1 to 20 and r represents an integer from 3 to 6.

Further, the tri- or more-functional selenium-containing polythiol as described above, is represented by formula (3):

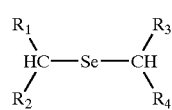

(3)

wherein, $R_1$, $R_2$, $R_3$ and $R_4$ each independently represents a hydrogen atom, mercapto group,

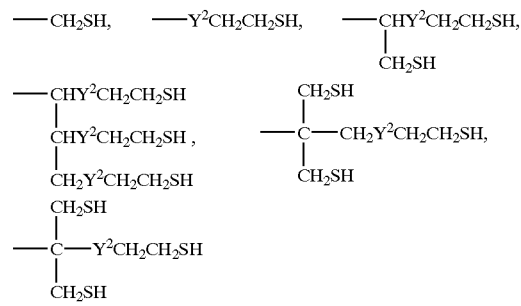

and $Y^2$ represents a sulfur atom or an Se atom.

And, a composition containing at least one tri- or more-functional selenium-containing polythiol as described above is provided.

A tri- or more-functional polythiol having-a selenium atom in an aliphatic chain structure has not been known until now.

The selenium-containing polythiol compound of the present invention. represented by the general formula (2) is a compound in which three or more mercapto groups are connected to a selenium-containing aliphatic chain structure as a center skeleton of which one or more carbon atoms are substituted by a selenium atom. This selenium-containing aliphatic chain structure is an aliphatic chain structure solely composed of single bond, and may have a straight-chain alkylene or branched alkylene without any problem.

A part of the carbon atoms constituting the selenium-containing alkylene skeleton may be substituted by other atoms such as a sulfur atom and oxygen atom other than a selenium atom.

Regarding bonding form of a mercapto group, one group may be connected to one atom, or two or more groups may be connected to the same atom.

The selenium-containing polythiol represented by formula (2) of the present invention is obtained, for example, by synthesizing a compound having selenium-containing alicyclic chain structure as a center skeleton using a selenium compound such as a selenium halide, alkaline metal selenide, alkaline metal selenol, alkyl(di)selenide, alkylselenol and hydrogen selenide, as described in literatures such as "The chemistry of selenium and tellurium compounds volume 1" (1986, Saul Patai and Zvi Roppoprt, John Wiley & Sons), and "Selenium reagents and intermediates in organic synthesis" (1986, J. E. Baldwin, Pergamon Press), then, by introducing a mercapto group by a known organic reaction and the like as described in literatures such as "Synthetic organic chemistry" (1953, Romeo B. Wagner and Harry D. Zook, John Wiley & Sons).

The selenium-containing polythiol represented by formula (2) can also be obtained by substituting a selenium compound for a part of the raw materials of the synthesizing methods described in JP-A Nos. 2-270,859 and 7-252,207. For example, 2-hydroxyethylselenol is used instead of 2-mercaptoethanol, or sodium selenide is used instead of sodium sulfide.

The production method thereof will be described according to a specific example of production process.

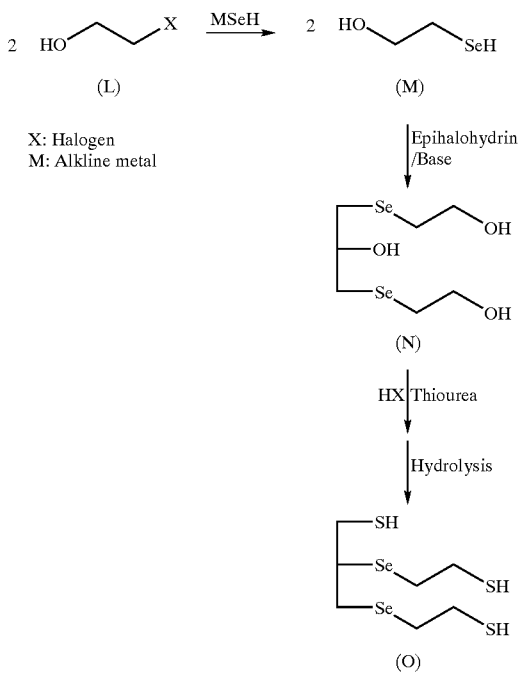

X: Halogen
M: Alkline metal

A halohydrin of formula (L) is reacted with an alkaline metal selenol such as sodium selenol and potassium selenol to synthesize a hydroxyselenol compound of formula (M).

The alkaline metal selenol herein used can be synthesized, for example, by a method described in a literature, "Handbook of preparative inorganic chemistry" (volume 1, second edition, 1963, Georg Brauer, Academic Press), as well as other methods.

The amount used of the alkaline metal selenol is preferably from 1 to 5 equivalents, particularly preferably from 1 to 3 equivalents based on the halogen atom in the raw material halohydrin.

The reaction is in the range from about −10 to 150° C., preferably from 0 to 120° C.

Regarding reaction solvent, it is efficient to use the solvent used for the synthesis of the alkaline metal selenol. Examples thereof include water, methanol, ethanol, isopropanol, ethylene glycol and the like.

A dihyroxyselenol of formula (M) is reacted with an epihalohydrin such as epichlorohydrin and epibromohydrin to obtain a polyol of formula (N). The amount used of the epihalohydrin is in the range from 0.4 to 0.6-fold mol, particularly preferably from 0.5 to 0.55-fold mol based on the hydroselenol group in the hydroxyselenol (M).

In this case, preferable results are often obtained when organic bases and inorganic bases such as triethylamine, pyridine, sodium hydroxide and potassium hydroxide are used.

The amount used of these bases is in the range from 0.5 to 2 equivalents, particularly preferably from 0.5 to 1 equivalent based on the hydroseleno group in the hydroxyselenol of formula (M).

The reaction temperature is in the range from 0 to 100° C., preferably from 5 to 50° C.

The reaction solvent may be used or not be used, it is efficient to use a solvent used in synthesizing an alkaline metal selenol as described above.

To the resulted polyol of formula (N), a hydrohalic acid such as hydrochloric acid and hydrobromic acid, and thiourea, further, if necessary, a known solvent such as water or alcohol are added, the resulting mixture is heated and stirred to produce a thiuronium salt. The amount used of the hydrohalic acid is from 1 to 20 equivalents, preferably from 1 to 5 equivalents based on the hydroxy group in the polyol of formula (N).

The reaction temperature is in the range from 0 to 150° C., preferably from 60 to 120° C.

Then, hydrolysis is conducted using a base such as sodium hydroxide, ammonia water and the like, to obtain an intended polythiol of formula (O). The amount used of these bases is preferably from 1 to 3 equivalents, particularly preferably from 1.1 to 2 equivalents based on the hydrohalogenic acid previously used.

The reaction temperature is in the range from 0 to 120° C., preferably from 20 to 80° C.

As methods for obtaining a selenium-containing polythiol compound other than the above-described methods, there are for example a method in which corresponding selenium-containing halogen compounds are synthesized, the halogen atom of the halogen compounds is substituted for a mercapto group, a method in which a corresponding disulfide compound is reduced to a mercapto group.

The selenium-containing halogen compounds are compounds having an electron attractive group such as corresponding chloro compound, bromo compound, methanesulfonate compound, benzenesulfonate compound and toluenesulfonate compound.

As methods for synthesizing this selenium-containing halogen compounds, there are listed, for example, a method in which a corresponding hydroxy compound is reacted with hydrochloric acid, hydrobromic acid, thionyl chloride, phosphorus tribromide, methanesulfonic acid, benzenesulfonic acid, tolurnesulfonic acid and the like, a method in which an olefin such as ethylene and propylene is reacted with a halogenated selenide such as dichloro diselenide, dibromo diselenide, tetrachloroselenium and tetrabromoselenium, a method in which compounds having an electrophilic functional group such as a ketone, aldehyde and acetal are reacted with halogenated selenol, as well as other methods.

As the method in which the electron attractive group in selenium-containing halogen compounds is substituted for a mercapto group to obtain a selenium-containing polythiol, various known methods can be used such as, for example, a method using thiourea, a method using sodium hydrogen sulfide, a method using alkaline metal polysulfides such as potassium polysulfide and sodium polysulfide, a method using potassium xanthate, a method using Bunte's salt, a method using alkaline metal trithiocarbonates such as sodium trithiocarbonate and potassium trithiocarbonate, as well as other methods.

As the reduction method for synthesizing a polythiol of formula (O) by reducing a corresponding disulfide compound, there are often used, for example, a reduction method using a metal such as iron and zinc, and hydrochloric acid and the like, a method using lithium aluminum hydride or sodium boron hydride; as well as other methods.

When the length of an alkylene chain which is the center skeleton of the polythiol of formula (O) is wished to be changed, the following methods are used.

The are a method in which a halogenated propanol is used instead of the halogenated ethanol of formula (L), a method in which the halogenated ethanol of formula (L) is reacted again with the polythiol of formula (O), a method in which sodium selenide, sodium selenol and the like are used instead of a hydroxyselenol compound of formula (M), as well as other methods.

The reaction solvent may be used or not be used for the synthesis of the polythiol of formula (O) and the composition thereof.

When the reaction solvent is used, any solvent can be used selected from conventional solvents described in "Solvent Handbook" (Shozo Asahara and others, published by Kodansha Ltd.) providing it does not exert influence on the reaction, taking out, product, and the like, and preferable examples thereof include hexane, benzene, toluene, xylene, chlorobenzene, di-chlorobenzene, chloroform, dichloroethane, methanol, ethanol, ispronanol and water.

Examples of the tri- or more-functional polythiol of the present invention other than those of formula (O) for which synthesis methods are exemplified above, include 2-mercaptoethylseleno-1,3-propanedithiol, bis(1,3-dimercapto-2-propyl)selenide, bis[1,3-bis(mercaptoethylthio)-2-propyl]selenide, bis[1,3-bis(mercaptoethylseleno)-2-propyl]selenide, bis(mercaptomethyl)-3,9-dithia-6-selenaundecane-1,11-dithiol, bis(mercaptomethyl)-3,9-diselena-6-thiaundecane-1,11-dithiol, bis(mercaptomethyl)-3,6,9-triselenaundecane-1,11-dithiol, 2,3-bis(mercaptoethylseleno)butane-1,4-dithiol, 1,2,3,4-tetrakis(mercaptoethylseleno)-butane, 5,5-bis(mercaptomethyl)-3,7-diselenanonane-1,9-dithiol and tris(mercaptomethyl)-3-selena-6-thiaoctane-1,8-dithiol.

The composition of the present invention essentially contains at least a tri- or more-functional selenium-containing polythiol represented by formula (2).

In addition to the tri- or more-functional polythiol represented by formula (2) of the present invention, other organic compounds and inorganic compounds including oligomers such as a dimer, trimer and tetramer thereof and a prepolymer thereof, mercapto compounds represented by formula (2) wherein n is 2 or less, polymerization inhibitor, resin-forming agents and resin modifier, additives, solvent used for synthesis, raw materials, and by-products and impurities may also be contained in the range which is not problematical.

The above-described resin-forming agent is a compound which reacts with a mercapto group to form a resin, and the resin modifying agent is a compound used for improving physical properties of the resin obtained by polymerization.

Examples of the resin-forming agent and resin modifier include mercapto compounds other than those represented by formula (2), iso(thio)cyanate compounds other than those represented by formula (2), (meth)acrylate compounds other than those represented by formula (2), allyl (vinyl, isopropenyl) compounds other than those represented by formula (2), (thio)epoxy compounds other than those represented by formula (2), carboxylic acids and carboxylic anhydrides, mercaptocarboxylic acids, hydroxy compounds, amino acids and mercaptoamines, amines and the like, and they can be added in the range which is not problematical until necessary physical properties of a resin are obtained.

Specific examples thereof include, but not limited to, mercapto compounds such as ethanedithiol, bis(2-mercaptoethyl)sulifide, 2,3-dimercapto-1-propanol, 1,2,3-trimercaptopropane, pentaerythritoltetrakis(2-mercaptothioglycolate), pentaerythritoltetrakis(3-mercaptopropionate), trimethylolpropanetris(2-mercaptothioglycolate), trimethylolpropanetris(3-mercaptopropionate), 2,5-bis(mercaptomethyl)thiophane, 2,5-dimercapto-1,4-dithiane, 2,5-dimercaptomethyl-1,4-dithiane, 2,3-bis(2-mercaptoethylthio)-1-propanethiol and bis(mercaptomethyl)-3,6,9-trithia-1,11-undecanedithiol; iso(thio)cyanates such as cyclohexylisocyanate, cyclohexylisothiocyanate, xylylene di-isocyanate, $\alpha,\alpha',\alpha''$, $\alpha'''$-tetramethylxylylene diisocyanate, 3-isopropenyl-$\alpha,\alpha'$-dimethylbenzylisocyanate, hexamethylene diisocyanate, trimethylhexamethylene diisocyanate, isophorone diisocyanate, dicyclohexylmethane diisocyanate, 1,3-bis(isocyanatomethyl)cyclohexane and bis(isocyanatomethyl)norbornane; (meth)acrylates such as methyl methacrylate, ethyleneglycol dimethacrylate, neopentylglycol diacrylate, bis(methacryloylmethyl)norbornene, bis(acryloylethoxyethyl)bisphenol F, bis(methacryloyloethoxyethyl)bisphenol F, bis(acryloylethoxyethyl)bisphenol A, bis(methacryloylethoxyethyl)bisphenol A, glycerine dimethacrylate, trimethylolpropane tris(acrylate), trimethylolpropane tris(methacrylate), pentaerythritoltris(acrylate), pentaerythritoltetrakis(acrylate) and 2,5-bis(methacryloylthiomethyl)-1,4-dithiane; allyl(vinyl, isopropenyl) compounds such as acrylonitrile, butadiene, styrene, divinylbenzene, di-isopropenylbenzene and diethylene glycol bis(allyl carbonate); (thio)epoxy compounds such as bis(3-epithiopropyl)sulfide, 1,2-bis(3-epithiopropylthio)ethane, 1,2-bis(3-epithiopropylthioethylthio)-3-(3-epithiopropylthio)propane, vinylcyclohexane diepoxide, bisphenol A diglycidyl ether, 3,4-epoxycyclohexylmethyl-3',4'-epoxycyclohexane carboxylate and 1,2-hexahydrophthalic acid diglycidyl ester; carboxylic acids and carboxylic anhydrides such as phthalic acid, phthalic anhydride, hexahydrophthalic anhydride, methylhexahydrophthalic anhydride, maleic anhydride, trimellitic anhydride and pyromellitic anhydride; mercaptocarboxylic acids such as thioglycolic acid, 3-mercaptopropionic acid, thiobutyric acid, thiomalic acid and thiosalicylic acid; hydroxy compounds such a glycerine, polyethylene glycol, polypropylene glycol, butane diol, butyric acid and polybutyric acid; amino acids and mercaptoamines such asaspartic acid, alanine, $\beta$-alanine, glycine, taurine, cysteine, cysteamine and aminobenzoic acid; amines such as hexamethylenediamine, isophoronediamine, bis(4-aminocyclohexyl)methane, 1,3-bis(aminomethyl)cyclohexane, bis(aminomethyl)norbornane, m-xylylenediamine and m-phenylenediamine.

These resin-forming agents and resin modifiers may be previously added in the reaction system or added in the recovery process providing there is no problem.

Further, these resin modifiers may be added after the tri- or more-functional polythiol or the composition containing the same of the present invention is recovered as a product, as represented by compounding and the like in polymerization work. These resin-forming agents and resin m odifiers may be used a lone or in combination of two or more.

The resin and plastic lens obtained by polymerizing the selenium-containing polythiol or the composition thereof of the present invention are usually obtained by a casting polymerization method in which a composition composed of the tri- or more-functional polythiol represented by formula (2) and the above-described resin-forming agent and the resin modifier is optionally- defoamed by a suitable method such as stirring under reduced pressure, then, the defoamed solution is poured into a mold composed of a metal or glass and resin, then, polymerization is conducted by heat and/or a radiation such as light.

The molding can be possible by a reaction injection molding method used for molding of a known epoxy resin and large scale urethane resin, however, this method is not so often used as a method for producing a plastic lens which is required to have strict optical uniformity since the resulting molded article tends to have optical strain.

In conducting casting polymerization, a curing catalyst is preferably used for the purpose of shortening polymerization time, and the like.

Though the kind of the curing catalyst is not restricted since the nature thereof significantly differs depending on the kind of a resin-forming agent and a resin modifier to be polymerized, if mentioned, amines, phosphines, Lewis acids, radical polymerization catalysts, cationic polymerization catalysts and the like are listed.

Examples thereof include, but are not limited to, amines such as ethylamine, 2-aminoethanol, 4,4'-diaminodiphenylmethane, dibutylamine, triethylamine, tributylamine, triethyldiamine, N,N-diethylaminoethanol, N,N-dimethylcyclohexylamine, N-methylmorpholine, piperidinem pyridine, β-picoline, 2-methylimidazole, dicyandiamide, hydrazide succinate, diaminomaleonitrile, diallylmelanine, aniline.phenylphophonic acid salt, ethylenediamine.phenylphosphoric acid salt, boron tetrafluoride-.monoethylamine salt, boron trifluoride.monoethylamine salt, phosphorus pentafluoride.isopropylamine complex, arsenic pentafluoride.and the like, phosphines such as trimethylphosphine, triethylphosphine, tripropylphosphine, tributylphosphine, tricyclohexylphosphine, tribenzylphosphine, triphenylphosphine, 1,2-bis(dimethylphosphino)ethane, 1,2-bis(diephnylphosphinno)ethane and the like, Lewis acids such as dimethyltin dichloride, dimethyltin oxide, tetrachlorotin, monobutyltin trichloride, dibutyltin dichloride, tributyltin monochloride, tetrabutyltin, dibutyltin oxide, dibutyltin dilaurate, dibutyltin octanoate, tin stearate, zinc chloride, acetylacetone zinc, aluminum fluoride, aluminum chloride, triphenylaluminum, tetraisopropoxytitanium, tetrabutoxytitanium, tetrachlorotitanium, calcium acetate and the like, radical polymerization catalysts such as di-isopropyl peroxydicarbonate, di-sec-butyl peroxydicarbonate, acetylacetone peroxide, cumene peroxide, t-butyl hydroperoxide, isobutyl peroxide, t-butylcumyl peroxide, 1,1-di-t-butyl peroxycyclohexane, 1,1,3,3-tetramethylbutyl peroxyneodecanoate, t-butyl peroxybenzoate, 2,2'-azobis(4-methoxy-2,4-dimethylvaleronitrile), 2,2'-azobis(2-cyclopropylpropionitrile), 2,2'-azobis(2,4-dimethylvaleronitrile), t-butyl peroxy-2-ethyl hexanoate, n-butyl-4,4'-bis(t-butyl peroxy)valerate, t-butyl peroxybenzoate and the like, cation polymerization catalysts such as diphenyliodonium hexafluorophorphoric acid, diphenyliodonium hexafluoroarsenic acid, diphenyliodonium hexafluoroantimony, triphenylsulfonium tetrafluoroboric acid, triphenylsulfonium hexafluorophosphoric acid, triphenylsulfonium hexafluoroarsenic acid and the like, as well as other compounds. These may be used alone or in combination of two or more.

When the curing catalyst is used, the amount used thereof is in the range from 0.001 to 10 wt %, preferably from 0.01 to 5 wt % based on the total amount of the composition containing the tri- or more-functional selenium-containing polythiol of the present invention. When the amount used is less than 0.01 wt %, the effect is low, and when over 10 wt %, the use of the catalyst is not impossible, however, disadvantages may sometimes occur such as shortening of pot life, or reduction in transparency, optical properties and weatherability.

In addition to the curing catalyst, known various additives such as an internal releasing agent, optical stabilizer, ultraviolet ray absorber, antioxidant, oil-soluble dyer and filler may be added according to the object in the range which is not problematical.

The polymerization conditions in the case of heat polymerization are not restricted since they differ depending on the kinds of the composition containing the tri- or more-functional selenium-containing polythiol of the present invention and curing catalyst, the form of a mold, and the like, and the heat polymerization is conducted at a temperature of about −50 to 200° C. for 1 to 100 hours. Depending on the occasion, preferable results may be imparted when polymerization is conducted for 4 to 70 hours while gradually increasing the temperature in the range from 10° C. to 150° C.

The polymerization conditions in the case of radiation polymerization are as described below.

As the radiation, an ultraviolet ray or a visual light is preferably used, among them, there is preferably used an ultraviolet ray having a wavelength of 400 nm or less with which a sensitizer having high coloring ability represented by camphorquinone and the like is often dispensable.

The quantity of the ultraviolet ray is not restricted like the case of heat polymerization since it differs depending on the kinds of the composition containing the di- or more-functional polymerizable compound of the present invention and curing catalyst, the form of a mold, and the like, and the ultraviolet ray is often irradiated at a strength of about 1 to 1000 mJ/sec for 1 to 7200 seconds, and in some cases, irradiated in several times or irradiated after cooling for the purpose of gradual heating.

Regarding the polymerization, heat polymerization may be combined with radiation polymerization without any problem. Further, the polymerized molded article and plastic lens may optionally be subjected to annealing treatment.

The resulted molded article and plastic lens of the present invention can be subjected, if necessary, to physical or chemical treatments such as surface abrasion, antistatic treatment, hard coating treatment, anti-reflection coating treatment, dyeing treatment and light control treatment, for effecting improvements such as prevention of reflection, imparting of high hardness, improvement of abrasion resistance, improvement in chemical resistance, imparting of antifogging property and imparting of fashionable appearance.

The present inventors have intensively studied and found that refractive index can be further improved if an aliphatic selenium-containing compound having in the molecule a selenium atom is used, completing the present invention.

Namely, the present invention provides a di- or more-functional aliphatic selenium-containing compound by formula (4):

$$(Z^3)-(X^2) \tag{4}$$

wherein, $Z^3$ represents a Se atom or an alkylene group containing at least one Se atom; $X^2$ represents a functional group selected from an acryloyl group, methacryloyl group and thioepoxy group, or an alkyl residue having this functional group; and s represents an integer from 2 to 6.

Further, the aliphatic selenium-containing compound of formula (4) is represented by formula (5):

$$X_1-Se-X_2 \tag{5}$$

wherein, $X_1$ and $X_2$ are the same or each independently represent

, , 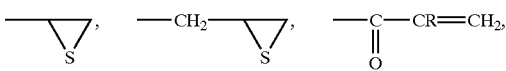

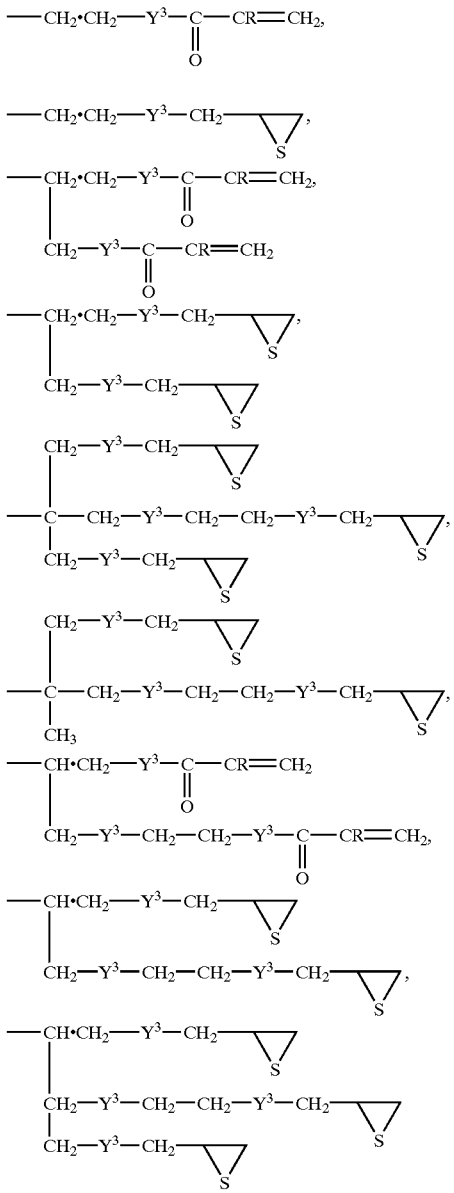

in which $Y^3$ represents a sulfur atom, oxygen atom or Se atom, and R represents a hydrogen atom or a methyl group, and a composition containing at least one aliphatic selenium-containing compound described above, are provided.

The di- or more-functional (meth)acryloyl compound or thioepoxy compound having in aliphatic chain structure a selenium atom has not been known until now at all.

The aliphatic selenium-containing compound according to the present invention represented by formula (4) has a center structure in which carbon atoms forming the aliphatic chain compound are situated around the selenium-containing chain structure substituted by one or more selenium atoms. This selenium-containing chain structure is a aliphatic chain structure solely composed of single bonds, and may be composed of only selenium atoms, a straight chain alkylene or a branched alkylene composed of selenium atoms and carbon atoms without any problem providing chain structure is formed.

A part of carbon atoms constituting the selenium-containing alkylene skeleton may be substituted by any atoms such as sulfur atom and oxygen atom other than selenium atom.

Two or more functional groups which are optionally connected to the center skeleton may be independently selected from one or more moieties selected from an acryloyl group, methacryloyl group and thioepoxy group.

The connected functional groups may be composed of solely the same kind of moiety or separately the different kinds of moieties without any problem.

Regarding connecting form of the functional group, one may be connected to one carbon atom, or two may be connected to the same carbon atom.

The aliphatic selenium-containing compound of formula (4) according to the present invention is obtained, for example, by synthesizing a compound having selenium-containing chain structure as a center skeleton using a selenium compound such as a selenium halide, alkaline metal selenide, alkaline metal selenol, alkyl(di)selenide, alkyl selenol and hydrogen selenide, as described in literatures such as "The chemistry of selenium and tellurium compounds volume 1" (Saul Patai and Zvi Roppoprt, 1986, John Wiley & Sons) and "Selenium reagents and intermediates in organic synthesis" (J. E. Baldwin, 1986, Pergamon Press), then, by introducing a functional group such as an acryloyl group, methacryloyl group and thioepoxy group by a known organic reaction as described in literatures such as "Synthetic organic chemistry" (Romeo B. Wagner and Harry D. Zook, 1953, John Wiley & Sons).

Steps for producing a product are described by way of a specific example.

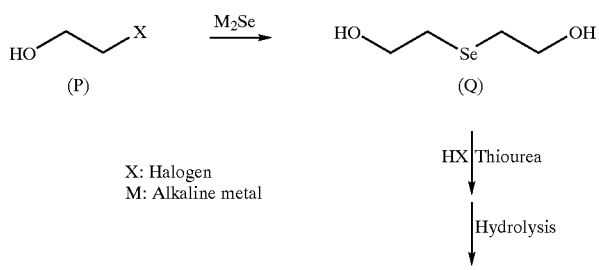

X: Halogen
M: Alkaline metal

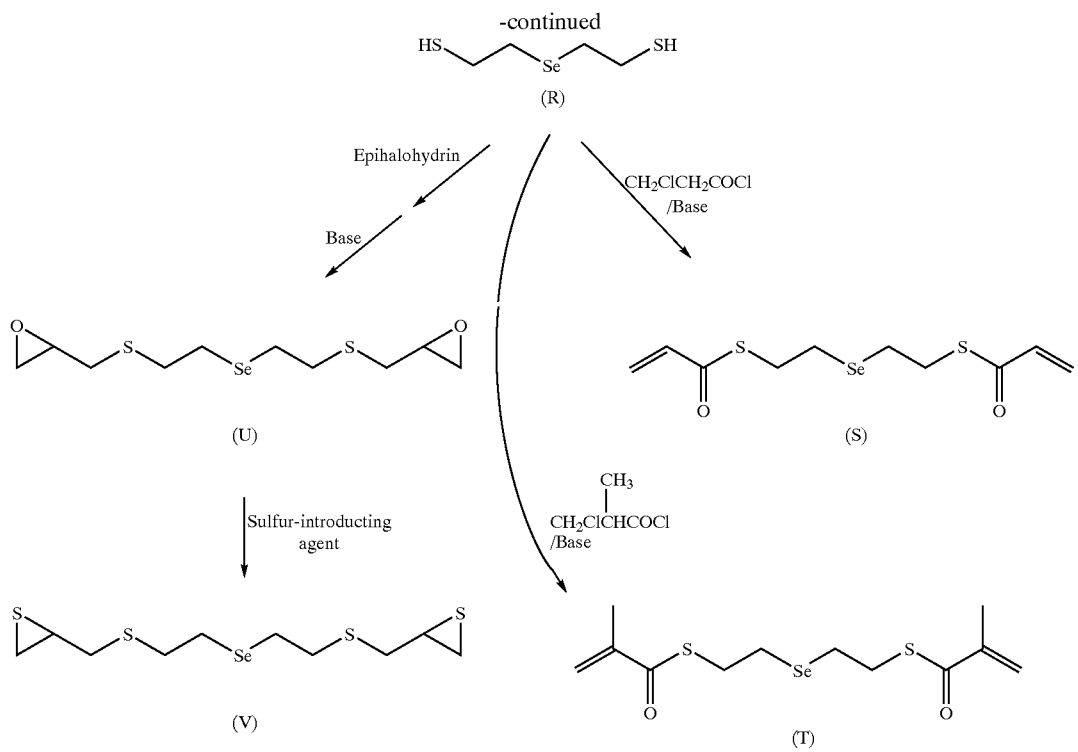

A halohydrin of formula (P) is reacted with an alkaline metal selenide such as sodium selenide and potassium selenide to synthesize a diol of formula (Q).

The alkaline metal selenide herein used can be synthesized, by a method described in a literature, "Handbook of preparative inorganic chemistry" (volume 1, second edition, 1963, Georg Brauer, Academic Press), as well as other methods.

A dithiol of formula (R) is obtained from the diol of formula (Q). First, to the diol of formula (Q), a mineral acid such as hydrochloric acid and hydrobromic acid, and thiourea, further, if necessary, a known solvent such as water and alcohol are added, the resulted mixture is heated and stirred at a temperature in the range from 40 to 150° C., preferably from 60 to 120° C. for about 1 to 24 hours, preferably from 1 to 8 hours, to produce a thiuronium salt. The amount used of the mineral acid is from 1 to 10 equivalents, preferably from 1.1 to 3 equivalents based on the hydroxy group in the diol of formula (Q). The amount used of thiourea is from 1 to 5 equivalents, preferably from 1 to 2 equivalents based on the hydroxy group in the dial (Q) likewise. Then, a base such as sodium hydroxide and aqueous ammonia is added, and-hydrolysis is conducted at a temperature in the range from 20 to 100° C., preferably from 40 to 60° C. for 1 to 10 hours, to obtain an intended dithiol of formula (R). Aqueous ammonia is relatively preferably as a base used in the hydrolysis, and the amount used of the base is usually from 1 to 3 equivalents, preferably from 1.1 to 2 equivalents based on the mineral acid previously used.

As a method for obtaining a selenium-containing thiol compound other than the above-described methods, for example, it is obtained by using corresponding compound containing selenium atom and electron attractive groups, and substituting this electron attractive group by a mercapto group.

The compound containing selenium atom and electron attractive groups are compounds having an electron attractive group such as corresponding chloro body, bromo body, methanesulfonate body, benzenesulfonate body and toluenesulfonate body.

As methods for synthesizing the compound containing selenium atom and electron attractive groups, there are listed, for example, a method in which a corresponding hydroxy compound is reacted with an agent having an electron attractive group such as hydrochloric acid, hydrobromic acid, thionyl chloride, phosphorus tribromide, methanesulfonic acid, benzenesulfonic acid and toluenesulfonic acid, a method in which an olefin such as ethylene and propylene is reacted with a halogenated selenide such as dichloro diselenide, dibromo diselenide, tetrachloroselenium and tetrabromoselenium, a method in which compounds having an electrophilic functional group such as a ketone, aldehyde and acetal are reacted with a halogenated selenol and the like, as well as other methods.

The amount used of the compound containing selenium atom and electron attractive groups is from 1 to 3 equivalents, preferably from 1 to 2 equivalents based on the hydroxy group.

The reaction temperature can not be particularly restricted since it varies significantly depending on the structure of the compound containing selenium atom and electron attractive groups and hydroxy compounds, and the like, and is from about 0 to 200° C., if further restricted, from 10 to 120° C.

As the method in which the electron attractive group in the compound containing selenium atom and electron attractive groups is substituted by a mercapto group to obtain a selenium-containing thiol, various known methods can be used, for example, such as a method using thiourea, a method using sodium hydrogen sulfide, a method using sodium polysulfide, a method using potassium xanthate, a method using Bunte's salt, and a method using alkaline metal trithiocarbonates such as sodium trithiocarbonate and potassium trithiocarbonate, as well as other methods.

The amount used of this mercapto group substituting agent is usually from 1 to 10 equivalents, preferably from 1 to 3 equivalents based on the electron attractive group. The reaction temperature can not be restricted since it varies significantly depending on the kind of the mercapto group substituting agent, the kind of the electron attractive group, and the structure of the selenium-containing electron attractive groups, and is in the range from about −10 to 200° C., particularly from 0 to 120° C.

When a solvent is optionally used, preferable results are often obtained when a polar solvent such as water, alcohol and amides is used.

When the alkylene group in formulae (S), (T) and(V) are changed, the following methods are used.

When an alkylene group only composed of carbon atoms and hydrogen atoms is extended, for example, a long chain halogenated alcohol such as a halogenated propanol, halogenated butanol and halogenated hexanol may advantageously be used instead of a halogenated ethanol of formula (P). When an alkylene group containing a hetero atom is extended, for example, there are listed a method in which a dithiol of formula (R) is reacted with the above-described halogenated alkyl alcohol again, a method in which the compound containing selenium atom and electron attractive groups are reacted with hydroxyalkylselenol, halogenated alkylselenol, hydroxyalkylthiol, halogenated alkylthiol and the like, as well as other methods. When an alkylene group is to be shortened, for example, there are listed a method in which an alkaline metal selenol, alkaline metal selenol or the like is reacted directly with a intended raw material having functional group such as an epihalohydrin, as well as other methods.

Bis[(meth)acryloylthioethyl]selenides of formulae (S) and (T) belonging to the (meth)acryloyl compound of the present invention are obtained from the above-described dithiol compound of formula (R).

For example, there are listed a two-stage method in which a dithiol of formula (R) is reacted with halogenated acid halide such as chloropropionic acid chloride, 3-chloro-2-methylpropionic acid chloride and the like to synthesize halogenated esters, then, de-hydrogen halide is conducted using a base such as triethylamine, pyridine, sodium hydroxide, potassium hydroxide, sodium methylate and the like, a method in which acid chlorides such as (meth)acrylic acid chloride and the like are reacted, and the like. The former two-stage method is often excellent from the viewpoints of purity and yield.

In the two-stage method, the amount used of halogenated acid halide when halogenated-esters are synthesized, is preferably from 1 to 2 equivalents, further preferably from 1 to 1.2 equivalents based on the mercapto group in the dithiol of formula (R).

The reaction temperature is preferably from 20 to 100° C., further preferably from 30 to 70° C. The reaction solvent may be used or not be used, and reaction speed is faster when it is not used.

A base such as triethylamine, pyridine, sodium hydroxide, potassium hydroxide and sodium methylate may be used or not be used as a hydrogen halide catching agent.

When an inert gas such as nitrogen is bubbled through the reaction system for the purpose of removing hydrogen halide, preferable results are often obtained.

The amount used of the base when dehydrohalogenation reaction is conducted using the same base as described above to obtain (meth)acryloyl compounds of formulae (S) and (T) is preferably from 1 to 10 equivalents, further preferably from 1 to 3 equivalents based on the halogen atom in the halogenated esters synthesized above.

The reaction temperature is preferably from −10 to 100° C., further preferably from 0 to 50° C.

The reaction solvent may be used or not be used, and when used, it is efficient to use a solvent which separates from water such as benzene, toluene, xylene, chlorobenzene, hexane, cyclohexane and the like when the product is recovered by extraction.

When polymethacrylic compound is synthesized, 3-halogeno-2-methylpropionic acid halide or methacrylic acid halide may be advantageously used.

As other (meth)acryloyl compound of the present invention, various compounds can be synthesized. For example, a diol of formula (Q) is reacted with the above-described halogenated acid halides or (meth)acrylic acid halides to obtain (meth)acryloyloxy compounds, further, the above-described selenium-containing halogen compound are reacted with an alkaline metal selenol such as sodium selenol and sodium selenide and an alkaline metal selenide to synthesize selenol compounds, then, according to the same manner, they are reacted with halogenated acid halides or (meth)acrylic acid halides to obtain (meth)acryloylseleno compounds.

The (meth)acryloyl compound of the present invention essentially contains one or more selenium atoms in its molecule, and two or more of either one or both of an acryloyl group and a methacryloyl group. Therefore, it is not affected by the connecting form of a (meth)acryloyl group and connecting atom, at all.

Bis(5,6-epithio-3-thiahexyl)selenide of formula (V) belonging to the thioepoxy compound of the present invention can be synthesized from epoxy compounds of formula (U) or corresponding allyl compounds.

The method using epoxy compounds of formula (U) is a method in which the epoxy compounds are reacted with a sulfur-introducing agent represented by thiourea, or metal thiocyanates such as sodium thiocyanate and potassium thiocyanate.

The amount used of these sulfur-introducing agents is preferably from 1 to 10 equivalents, further preferably from 1 to 4 equivalents based on the epoxy group in formula (U).

The reaction temperature is preferably from 0 to 120° C., further preferably from 10 to 70° C.

When thiourea is used as the sulfur-introducing agent, addition of an acid such as acetic anhydride is effective as a stabilizing agent, and preferable results are often obtained.

The reaction solvent may be used or not be used, and when used, alcohols such as methanol, ethanol, isopropanol, glycerin and the like, hydrocarbons such as benzene, toluene, xylene and the like, halogenated hydrocarbons such as chloroform, dichloromethane, chlorobenzene and the like, water, as well as other solvents are preferably used. These solvents may be used alone or in combination of two or more to form a mixed solvent.

In the case of the mixed solvent, when surfactants such as alcohols, tertiary alkylammonium salts, alkyl or arylcarboxylic acid metal salts, alkyl or arylsulfonic acid metal salts, acidic alkyl or arylphosphate and metal salts thereof are added as phase transfer catalysts, the reaction results are excellent and recovery is efficient in many cases.

The amount added of these surfactants is preferably from 0.001 to 20 wt %, further preferably from 0.01 to 10 wt % based on the total amount of the reaction mass.

Bis(glycidylthioethyl)selenide of formula (U) belonging to the epoxy compounds of the present invention can be synthesized from a dithiol of formula (R) or corresponding allyl compounds and the like.

As the method using the thiol, for example, there are listed a two-stage method in which the dithiol of formula (R) is reacted with halohydrins such as epichlorohydrin and epibromohydrin to synthesize halogenated alcohol, then, dehydrohalogenation is conducted using a base such as triethylamine, pyridine, sodium hydroxide, potassium hydroxide and sodium methylate, a method in the above-described halohydrins are reacted in one stage using the above-described base, and the like.

The former two-stage method is often excellent from the viewpoints of purity and yield.

The allyl compounds used for synthesizing the compounds of formula (U) and formula (V) are bis(allylthioethyl)selenides, and are usually obtained by reacting a dithiol of formula (R) with allylhalides such as allyl chloride, allyl bromide and the like in the presence of sodium hydroxide, potassium hydroxide, sodium methylate, triethylamine and the like.

As the method for synthesizing epoxy compounds from the allyl compounds, there are listed, like the method used for synthesis of propylene oxide, for example, a method in which an allyl group is reacted with water and a halogen such as chlorine and bromine to synthesize halogenated alcohol, then, dehydrohalogenation reaction is conducted a method in which an allyl group is reacted with a peroxide such as peroxybenzoic acid to conduct direct oxidation and synthesis, and the like.

The direct oxidation method using a peroxide is not so preferable method since it is accompanied by crisis such as explosion and the like.

As the method for synthesizing thioepoxy compounds from allyl compounds, there are listed, a method in which an allyl group is reacted with a halogenated sulfur such as sulfur chloride, sulfur bromide and the like, then, reducing de-hydrohalogenation reaction is conducted using sodium sulfide and the like, as well as other methods.

An intended thioepoxy compound can be obtained in some cases only by reaction with a halogenated sulfur, even if a reducing de-hydrohalogenation agent such as sodium sulfide is not used.

Other thioepoxy compounds of the present invention can be synthesized. For example, bis(5,6-epithio-3-oxahexyl)selenide is obtained by using a diol of formula (Q) instead of dithiols of formula (R), and further, bis(5,6-epithio-3-selenahexyl)selenide is synthesized using 3-selenalieptane-1,5-diselenol obtained by reacting an alkaline metal selenol and alkaline metal selenide such as sodium selenol, sodium selenide and the like with the above-described selenium halides instead of dithiols of formula (R).

The thioepoxy compound of the present invention essentially contains one or more selenium atoms and two or more epithio groups in its molecule. Therefore, it is not affected by the connecting form of an epithio group and connecting atom, at all.

When acids such as sulfuric acid, phosphoric acid, hydrochloric acid, acetic anhydride and phthalic anhydride are added for the purpose of improving stability in synthesis and storage of the thus obtained thioepoxy compound of formula (V), preferable results are often obtained.

The reaction solvent may be used or not be used, in synthesizing the compound of formula 4) of the present invention containing compounds represented by formulae (S), (T) and (V).

When the solvent is used, any solvent can be used selected from conventional solvents described in "Solvent Handbook" (Shozo Asahara and others, published by Kodansha Ltd.) providing it does not exert influence on the reaction, taking out, product, and the like.

Preferable solvents can not be particularly restricted since the reaction and conditions differ significantly. If restricting them, alcohol such as methanol, ethanol, isoprenanol, ethylene glycol and ethylcellosolve; hydrocarbons such as benzene, toluene, xylene, hexane and cyclohexane; halogenated hydrocarbons such as dichloromethane, chloroform, dichloroethane, chlorobenzene, dichlorobenzene and trichlorobenzene; polar solvents such as acetonitrile, N,N-dimethylformamide, N,N-dimethylimidazolidinone, acetone and methyl isobutyl ketone; esters such as ethyl acetate, butyl acetate and amyl acetate; and water are listed.

Examples of the compounds of the present invention other than those represented by formulae (S), (T) and (V) of which synthesis methods are exemplified above include, but are not limited to, bis(1f2-epithioethyl)selenide, bis(2,3-epithiopropyl)selenide, bis(2,3-epithiopropyl)diselenide, bis (3,4-epithio-1-selenabutyl)methane, bis[(meth)acryloylseleno]-ethane, 1,2-bis(3,4-epithio-1-selenabutyl)ethane, bis[(meth)acryloyloxyethyl]selenide, bis(5,6-epithio-3-oxahexyl)selenide, 2,3-bis[(meth)acryloylthioethylseleno)-1-[(meth)acryloylthio)propane, 2,3-bis(6,7-thioepoxy-1-selena-4-thiaheptyl)-1-(3,4-thioepoxy-1-thiabutyl)propane, 1,1,3,3-tetrakis[(meth) acryloylthiomethyl]-2-selenapropane, 1,1,3,3-tetrakis(4,5-thioepoxy-2-thiapentyl)-2-selenapropane, bis(4,5-thioepoxy-2-thiapentyl)-3,6,9-triselenaundecane-1,11-bis(3, 4-thioepoxy-1-thiabutyl), 1,4-bis(3,4-thioepoxy-1-thiabutyl)-2,3-bis(6,7-thioepoxy-1-selena-4-thiaheptyl) butane and tris(4,5-thioepoxy-2-thiapentyl)-3-selena-6-thiaoctane-1,8-bis (3,4-thioepoxy-1-thiabutyl).

The composition of the present invention essentially contains at least a di- or more-functional polymerizable compound represented by formula (4).

In addition to the di- or more-functional compound represented by formula (4) of the present invention, other organic compounds and inorganic compounds including oligomers such as a dimer, trimer and tetramer thereof and a prepolymer thereof, polymerization inhibitor, resin modifier, additives, solvent used for synthesis, raw materials, and by-products and impurities may also be contained.

The above-described resin modifier is used for the purpose of improving physical properties of the resin obtained by polymerization, and for example, (meth)acrylate compounds other than those represented by formula (4), (thio) epoxy compounds other than those represented by formula (4), mercapto compounds, iso(thio)cyanate compounds, allyl(vinyl, isopropenyl) compounds, epoxy compounds, carboxylic acids and carboxylic anhydrides, mercaptocarboxylic acids, hydroxy compounds, amino acids and mercaptoamines, amines and the like are listed, and they can be added in the range which is not problematical until necessary physical properties are obtained.

Specific examples of the resin modifier include, but are not limited to, ethanedithiol, mercapto compounds such as bis(2-mercapto)sulfide, 2,3-dimercapto-1-propanol, 1,2,3-trimercaptopropane, pentaerythritoltetrakis(2-mercapto thioglycolate), pentaerythritoltetrakis(3-mercapto propionate), trimethylolpropanetris(2-mercapto thioglycolate), trimethylolpropanetris(3-mercapto propionate), 2,5-bis(mercaptomethyl)thiophane, 2,5-dimercaptomethyl-1,4-dithiane, 2,3-bis(2-mercaptoethylthio)-1-propanethiol, bis(mercaptomethyl)-3, 6,9-trithia-1,11-undecanedithiol and the like, iso(thio) cyanates such as cyclohexylisocyanate, cyclohexylisothiocyanate, xylylene diisocyanate, α,α',α", α'"-tetramethylxylylene di-isocyanate, 3-isopropenyl-α,α'-dimethylbenzylisocyanate, hexamethylene di-isocyanate, trimethylhexamethylene di-isocyanate, isophorone di-isocyanate, dicyclohexylmethane di-isocyanate, 1,3-bis(isocyanatomethyl)cyclohexane, bis(isocyanatomethyl)norbornane and the like, (meth)acrylates such as methyl methacrylate, ethylene glycol dimethacrylate, neopentyl glycol diacrylate, bis(methacryloylmethyl)norbornane, bis(acryloylethoxyethyl)bisphenol F, bis(methacryloyloethoxyethyl)bisphenol F, bis(acryloylethoxyethyl)bisphenol A, bis(methacryloylethoxyethyl)bisphenol A, glycerine dimethacrylate, trimethylolpropanetris(acrylate), trimethylolpropanetris(methacrylate), pentaerythritoltris(acrylate), pentaerythritoltetrakis(acrylate), 2,5-bis(methacryloylthiomethyl)-1,4-dithiane and the like, allyl (vinyl, isopropenyl) compounds such as acrylonitrile, butadiene, styrene, divinylbenzene, diisopropenylbenzene, diethylene glycol bis(allyl carbonate) and the like, (thio) epoxy compounds such as bis(3-epithiopropyl)sulfide, 1,2-bis(3-epithiopropylthio)ethane, 1,2-bis(3-epithiopropylthioethylthio)-3-(3-epithiopropylthio)propane, vinylcyclohexane diepoxide, bisphenol A diglycidyl ether, 3,4-epoxycyclohexylmethyl-3',4'-epoxycyclohexane carboxylate, 1,2-hexahydrophthalic acid diglycidyl ester and the like, carboxylic acids and carboxylic anhydrides such as phthalic acid, phthalic anhydride, hexahydrophthalic anhydride, methylhexahydrophthalic anhydride, maleic anhydride, trimellitic anhydride, pyromellitic anhydride and the like, mercaptocarboxylic acids such as thioglycolic acid, 3-mercaptopropionic acid, thiobutyric acid, thiomalic acid, thiosalicylic acid and the like, mercaptocarboxylic acids such as thiodiglycolic acid, thiodipropionic acid, dthiodipropionic acid and the like, hydroxy compounds such a glycerine, polyethylene glycol, polypropylene glycol, butane diol, butyric acid, polybutyric acid and the like, amino acids and mercaptoamines such as aspartic acid, alanine, β-alanine, glycine, taurine, cysteine, cysteamine, aminobenzoic acid; and amines such as hexamethylenediamine, isophoronediamine, bis(4-aminocyclohexyl)methane, 1,3-bis(aminomethyl)cyclohexane, bis(aminomethyl)norbornane, m-xylylenediamine and m-phenylenediamine.

These resin modifiers may be previously added in the reaction system or added in the recovery process providing there is no problem.

Further, these resin modifiers may be added after the di- or more-functional aliphatic selenium-containing compound or the composition containing the same of the present invention is recovered as a product, as represented by compounding and the like in polymerization work. These resin modifiers may be used alone or in combination of two or more.

The resin and plastic lens obtained by polymerizing a composition composed of the di- or more-functional aliphatic selenium-containing compound or the composition of the present invention are usually obtained by a casting polymerization method in which the di- or more-functional aliphatic selenium-containing compound represented by formula (4) and the composition containing the same are optionally defoamed by a suitable method such as stirring under reduced pressure, then, the defoamed solution is poured into a mold composed of a metal or glass and resin, then, polymerization is conducted by heat and/or a radiation such as a light.

The molding can be possible by a reactive injection molding method used for molding of a usual epoxy resin and large scale urethane resin, however, this method is not so often used as a method for producing a plastic lens which is required to have strict optical uniformity since the resulting molded article tends to have optical strain.

In conducting casting polymerization, a curing catalyst is preferably used for the purpose of shortening polymerization time, and the like.

Though the kind of the curing catalyst is not restricted since the nature thereof significantly differs depending on the kind of a reaction group to be polymerized, for example, amines, phosphines, Lewis acids, radical polymerization catalysts, cation polymerization catalysts and the like are listed.

Examples thereof include, but are not limited to, amines such as ethylamine, 2-aminoethanol, 4,4'-diaminodiphenylmethane, dibutylamine, triethylamine, tributylamine, triethyldiamine, N,N-diethylaminoethanol, N,N-dimethylcyclohexylamine, N-methylmorpholine, piperidinem pyridine, b-picoline, 2-methylimidazole, dicyandiamide, hydrazide succinate, diaminomaleonitrile, diallylmelanine, aniline.phenylphosphonic acid salt, ethylenediamine.phenylphosphoric acid salt, boron tetrafluoride-.monoethylamine salt, boron trifluoride.monoethylamine salt, phosphorus pentafluoride.isopropylamine complex, arsenic pentafluoride.laurylamine complex, antimony pentafluoride.benzylamine complex and the like, phosphines such as trimethylphosphine, triethylphosphine, tripropylphosphine, tributylphosphine, tricyclohexylphosphine, tribenzylphosphine, triphenylphosphine, 1,2-bis(dimethylphosphino)ethane, 1,2-bis(diephnylphosphinno)ethane and the like, Lewis acids such as dimethyltin dichloride, dimethyltin oxide, tetrachlorotin, monobutyltin trichloride, dibutyltin dichloride, tributyltin monochloride, tetrabutyltin, dibutyltin oxide, dibutyltin dilaurate, dibutyltin octanoate, tin stearate, zinc chloride, acetylacetone zinc, aluminum fluoride, aluminum chloride, triphenylaluminum, tetraisopropoxytitanium, tetrabutoxytitanium, tetrachlorotitanium, calcium acetate and the like, radical polymerization catalysts such as benzylmethyl ketal, diisopropyl peroxydicarbonate, di-sec-butyl peroxydicarbonate, acetylacetone peroxide, cumene peroxide, t-butyl hydroperoxide, isobutyl peroxide, t-butylcumyl peroxide, 1,1-di-t-butyl peroxycyclohexane, 1,1,3,3-tetramethylbutyl peroxyneodecanoate, t-butyl peroxybenzoate, 2,2'-azobis(4-methoxy-2,4-dimethylvaleronitrile), 2,2'-azobis(2-cyclopropylpropionitrile), 2,2'-azobis(2,4-dimethylvaleronitrile), t-butyl peroxy-2-ethyl hexanoate, n-butyl-4,4'-bis(t-butyl peroxy)valerate, t-butyl peroxybenzoate and the like, cation polymerization catalysts such as diphenyliodoniumhexafluorophorphoric acid, diphenyliodonium hexafluoroarsenic acid, diphenyliodonium hexafluoroantimony, triphenylsulfonium tetrafluoroboric acid, triphenylsulfonium hexafluorophosphoric acid, triphenylsulfonium hexafluoroarsenic acid and the like, as well as other compounds. These may be used alone or in combonation of two or more.

When the curing catalyst is used, the amount used thereof is in the range from 0.001 to 10 wt %, preferably from 0.01 to 5 wt % based on the total amount of the di- or more-functional aliphatic selenium-containing compound or the composition containing the same of the present invention. When the amount used is less than 0.01 wt %, the effect is low, and when over 10 wt %, the use of the catalyst is not impossible, however, disadvantages may sometimes occur such as shortening of pot life, or reduction in transparency, optical properties and weatherability.

In addition to the curing catalyst, known various additives such as an internal releasing agent, optical stabilizer, ultraviolet ray absorber, antioxidant, oil-soluble dye and filler may be added according to the object in the range which is not problematical.

The polymerization conditions in the case of heat polymerization are not restricted since they differ depending on the kinds of the di- or more-functional polymerizable compound and the composition thereof of the present invention, resin modifier and curing catalyst, the form of a mold, and the like, and the heat polymerization is conducted at a temperature of about −50 to 200° C. for 1 to 100 hours.

Depending on the occasion, preferable results may be imparted when polymerization is conducted for 4 to 70 hours while gradually increasing the temperature in the range from 10° C. to 150° C.

The polymerization conditions in the case of radiation polymerization are as described below.

As the radiation, an ultraviolet ray or a visual light is preferably used, among them, there is preferably used an ultraviolet ray having a wavelength of 400 nm or less with which a sensitizer having high coloring ability represented by camphorquinone and the like is often dispensable.

The quantity of the ultraviolet ray is not restricted like the case of heat polymerization since it differs depending on the kinds of the di- or more-functional polymerizable compound and the composition thereof of the present invention, resin modifier and curing catalyst, the form of a mold, and the like, and the ultraviolet ray is often irradiated at a strength of about 1 to 1000 mJ/sec for 1 to 7200 seconds, and in some cases, irradiated in several times or irradiated after cooling for the purposed of gradual heating.

Regarding the polymerization, heat polymerization may be combined with radiation polymerization without any problem. However, the present invention is not limited to these polymerization embodiments and polymerization conditions.

Further, the polymerized molded article and plastic lens may optionally be subjected to annealing treatment.

The resulted molded article and plastic lens of the present invention can be subjected, if necessary, to physical or chemical treatments such as surface abrasior, antistatic treatment, hard coating treatment, anti-reflection coating treatment, dyeing treatment and light control treatment, for effecting prevention of reflection, imparting of high hardness, improvement in chemical resistance, imparting of antifogging property, imparting of fashionable appearance or the like.

Next, the present invention will be described in more detail in accordance with examples and comparative examples. Incidentally, refractive indexes and Abbe numbers of obtained lenses were measured at 20° C. by the use of a Pulfrich refractometer.

EXAMPLE 1

25.9 parts (0.10 mole) of 4-thia-1-selenane-2,6-dimercaptomethyl, 18.8 parts (0.10 mole) of m-xylylene diisocyanate (hereinafter abbreviated to "XDII"), 0.01 wt % of dibutyltin dichloride (hereinafter abbreviated to "DBC") and 0.1 wt % of dioctyl phosphate were mixed with one another to form a uniform solution, followed by defoaming at 20° C. under reduced pressure.

After 1 hour, the solution was poured into a concave lens mold comprising a glass mold and a gasket and having a central thickness of 1.5 mm, and this mold was then slowly heated from room temperature up to 120° C. to cure the solution. After cooling, the resultant lens was taken out of the mold, and then heated at 120° C. again to obtain a transparent plastic lens.

The results of the obtained lens are shown in Table 1.

EXAMPLE 2

50 parts of 2,5-diacryloylthiomethylselenophane and 300 ppm of benzylmethylketal were mixed with each other to form a uniform solution, followed by defoaming at 20° C. under reduced pressure.

After ten minutes, the solution was poured into a concave lens mold comprising a glass mold and a gasket and having a central thickness of 1.5 mm, and this mold was then irradiated with ultraviolet light. After cooling, the resultant lens was taken out of the mold, and then heated at 140° C. again to obtain a transparent plastic lens. The results of the obtained lens are shown in Table 1.

EXAMPLES 3 TO 32, COMPARATIVE EXAMPLES 1 TO 3

Plastic lenses were obtained by the same procedure as in Example 1 or Example 2. The results of the obtained lenses are shown in Tables 1 and 2.

TABLE 1

| | Composition | Nd | νd |
|---|---|---|---|
| Ex. 1 | 4-thia-1-selenane-2,6-bis(mercaptomethyl) (HS-CH₂-[S,Se-containing 6-membered ring]-CH₂-SH) + XDI | 1.674 | 32 |
| Comp. Ex. 1 | HS-CH₂-[dithiane ring]-CH₂-SH + XDI | 1.662 | 32 |
| Comp. Ex. 2 | Tetrabromobisphenol (HO-[C₆H₂Br₂]-C(CH₃)₂-[C₆H₂Br₂]-OH) + XDI | 1.612 | 31 |

TABLE 1-continued

| | Composition | Nd | νd |
|---|---|---|---|
| Ex. 3 | CH₂CH—CO—S—CH₂—[tetrahydroselenophene ring]—CH₂—S—CO—CH=CH₂ | 1.648 | 33 |
| Comp. Ex. 3 | CH₂CH—CO—S—CH₂—[tetrahydrothiophene ring]—CH₂—S—CO—CH=CH₂ | 1.634 | 35 |

TABLE 2

| | Composition | Nd | νd |
|---|---|---|---|
| Ex. 3 | HS—[1,4-diselenane with CH₂SH groups]—SH + XDI | 1.69 | 30 |
| Ex. 4 | HS—[selenolane with CH₂SH groups]—SH + XDI | 1.66 | 32 |
| Ex. 5 | HS—[selenolane]—SH + XDI | 1.68 | 30 |
| Ex. 6 | HS—[1,4-thiaselenane]—SH + XDI | 1.70 | 29 |
| Ex. 7 | HS—[1,4-diselenane]—SH + XDI | 1.72 | 28 |
| Ex. 8 | HS—[diselenolane]—SH + XDI | 1.73 | 26 |
| Ex. 9 | HS—[selena-norbornane]—SH + XDI | 1.67 | 32 |
| Ex. 10 | HS—[selena-bicyclic]—SH + XDI | 1.67 | 32 |
| Ex. 11 | FSH + OCN—[thia-selenane]—NCO | 1.68 | 33 |
| Ex. 12 | FSH + OCN—[selenolane]—NCO | 1.66 | 35 |

TABLE 2-continued

| | Composition | Nd | vd |
|---|---|---|---|
| Ex. 13 | FSH + [structure: selenolane with OCN and NCO substituents] | 1.69 | 33 |
| Ex. 14 | FSH + [structure: selenane with OCN and NCO substituents] | 1.70 | 32 |
| Ex. 15 | FSH + [structure: 1,4-diselenane with OCN and NCO substituents] | 1.72 | 30 |
| Ex. 16 | FSH + [structure: 1,3-diselenolane with OCN and NCO substituents] | 1.72 | 30 |
| Ex. 17 | FSH + [structure: selena-norbornane with OCN and NCO substituents] | 1.68 | 35 |
| Ex. 18 | HS–[C–Se–C]–SH (tetrathiol selenide) + [selenane diisocyanate] | 1.70 | 33 |
| Ex. 19 | [diselenane dithiol] + [diselenane diisocyanate] | 1.77 | 27 |
| Ex. 20 | [selenane dithiol] (0.10 mole) + GST (0.03 mole) + OCN–CH$_2$–Se–CH$_2$–NCO (0.145 mole) | 1.72 | 31 |
| Ex. 21 | CH$_2$–SH<br>\|<br>CH–Se–CH$_2$CH$_2$–SH<br>\|<br>CH$_2$–Se–CH$_2$CH$_2$–SH + [thia-selenane diisocyanate] | 1.74 | 29 |
| Ex. 22 | CH$_2$=CH–CO–S–[CH$_2$–(thia-selenane)–CH$_2$]–S–CO–CH=CH$_2$ | 1.67 | 34 |
| Ex. 23 | CH$_2$=C(CH$_3$)–CO–S–[CH$_2$–(thia-selenane)–CH$_2$]–S–CO–C(CH$_3$)=CH$_2$ | 1.65 | 36 |
| Ex. 24 | CH$_2$=CH–CO–S–[(diselenane)]–S–CO–CH=CH$_2$ | 1.69 | 32 |

TABLE 2-continued

| | Composition | Nd | vd |
|---|---|---|---|
| Ex. 25 | 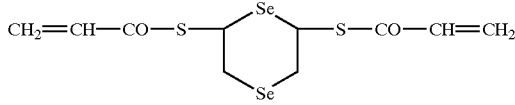 | 1.71 | 30 |
| Ex. 26 | 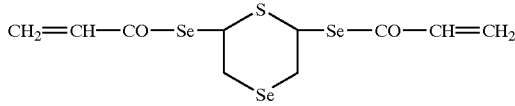 | 1.73 | 28 |
| Ex. 27 | 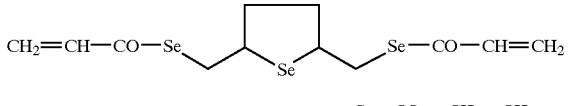 | 1.69 | 30 |
| Ex. 28 | 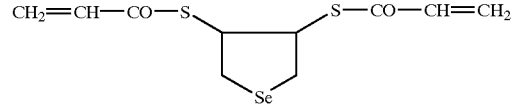 | 1.67 | 32 |
| Ex. 29 | 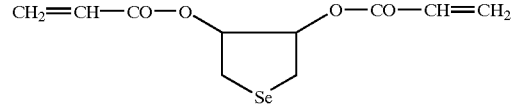 | 1.60 | 40 |
| Ex. 30 | 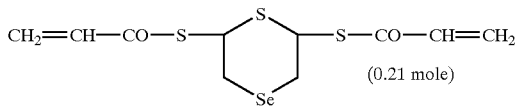 (0.21 mole)<br>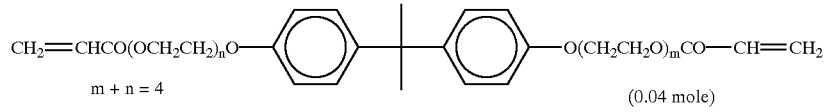 (0.04 mole)<br>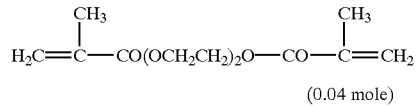 (0.04 mole) | 1.65 | 36 |
| EX. 31 | CH$_2$=CHCO—S—CH$_2$CH$_2$—Se—CH$_2$CH$_2$—S—COCH=CH$_2$ | 1.66 | 31 |
| EX. 32 | 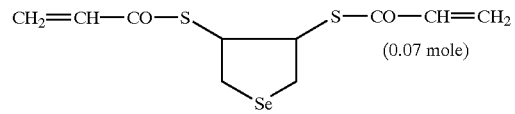 (0.07 mole)<br>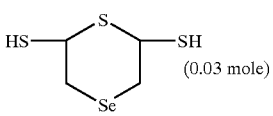 (0.03 mole) | 1.69 | 32 |

EXAMPLE 33

A mixed solution of 50 parts of 3,4-diglycidylthioselenophane, 10 parts of hexahydrophthalic anhydride, 5 parts of 3,5-dimercaptomethylselenophane, 1 part of dioctylphosphoric acid, 1000 ppm of dibutyltin dilaurate and 1000 ppm of triethylenediamine was defoamed under reduced pressure, and immediately, the solution was poured into a concave lens mold comprising a glass mold and a gasket and having a central thickness of 1.5 mm.

Next, this mold was then slowly heated from 50° C. to 130° C. to cure the solution. After cooling, the resultant lens was taken out of the mold, and then heated at 140° C. again to obtain a transparent plastic lens. The results of the obtained lens are shown in Table 3.

EXAMPLE 34

50 parts of 3,4-selenophanedithiolbis(allyl thiocarbonate), 1.5 parts of t-butylperoxy(2-ethyl hexanoate), 1.5 parts of benzylmethylketal and 0.5 part of diphenyliodonium hexafluoroantimonate were mixed with one another to form a uniform solution, followed by defoaming at room temperature under reduced pressure.

After 1 hour, the solution was poured into a concave lens mold comprising a glass mold and a gasket and having a central thickness of 1.5 mm, and this mold was then slowly heated from 70° C. to 120° C. to cure the solution. Furthermore, this mold was then irradiated with ultraviolet light, and the resultant lens was taken out of the mold.

Lastly, it was heated at 140° C. again to obtain a transparent plastic lens. The results of the obtained lens are shown in Table 3.

EXAMPLES 35 TO 38

Plastic lenses were obtained by the same procedure as in Example 33 or Example 34. The results of the obtained lenses are shown in Table 3.

TABLE 3

| | Composition | Nd | νd |
|---|---|---|---|
| Ex. 33 | 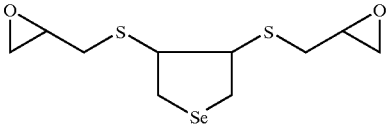 | 1.65 | 38 |
| Ex. 34 | 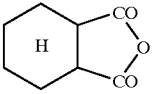 | 1.65 | 38 |
| Ex. 35 | 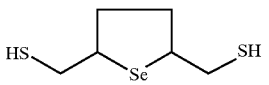 (0.20 mole) 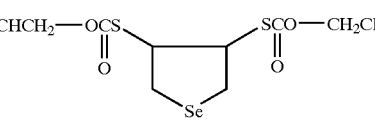 (0.02 mole) | 1.64 | 33 |
| Ex. 36 | 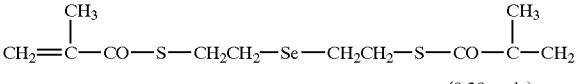 | 1.68 | 35 |
| Ex. 37 | 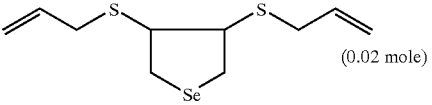 | 1.56 | 46 |
| Ex. 38 | 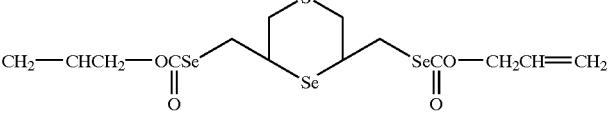 (0.01 mole) 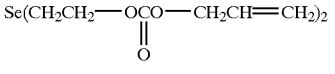 (0.04 mole) 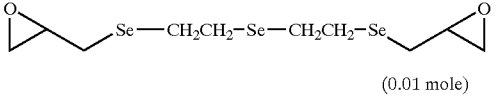 (0.01 mole) | 1.66 | 35 |

EXAMPLE 39

40 parts (0.15 mole) of 4-thia-1-selenane-2,6-dimercaptomethyl, 10 parts (0.05 mole) of norbornane diisocyanatomethyl, 0.1 part (1000 ppm) of dimethyltin dichloride and 0.05 part (500 ppm) of diphenyliodonium hexafluoroarsenic acid were stirred on a warm bath to carry out a urethane producing reaction. After 4 hours, the resultant reaction solution was cooled to room temperature.

Next, to the resultant highly viscous liquid (the addition-polymerized oligomer), 50 parts (0.25 mole) of ethyleneglycol dimethacrylate were added, and the mixture was then made uniform. This uniform solution was defoamed with stirring at room temperature under reduced pressure. After 0.5 hour, the solution was poured into a concave lens mold comprising a glass mold and a gasket and having a central thickness of 1.5 mm, and this mold was then irradiated with ultraviolet light to cure the solution. After cooling, the resultant lens was taken out of the mold.

Lastly, the lens was heated at 130° C. again to obtain a transparent plastic lens. The results of the obtained lens are shown in Table 4.

The lower organic layer was washed with 100 ml of 98% sulfuric acid and then separated, and anhydrous calcium chloride was added thereto, followed by stirring and filtration. 1110 parts (gross yield=81%) of a blackish brown filtrate which was selenium chloride ($Se_2Cl_2$) were obtained.

Synthesis of an Unsaturated Compound 74.1 parts (0.938 mole) of selenium, 270 parts (1.75 moles) of Rongalit, 210 parts (5.25 moles) of sodium hydroxide were dissolved in 1200 ml of water, and to the solution, a solution obtained by dissolving 227.1 parts (1.89 moles) of allyl bromide in 1200 ml of ethanol was then slowly added dropwise. The resultant reaction solution was extracted with chloroform, and the extract was then dried over calcium chloride. Afterward, the solvent was distilled off, and the residue was distilled under reduced pressure to obtain 90.9 parts of a fraction of 26 to 29° C./7 Torr (purity=97% according to the measured results of GC, purity conversion yield=58%).

It was confirmed by the results of elemental analysis, MS, NMR and IR analysis that the obtained fraction was diallyl selenide.

TABLE 4

| | Composition | Nd | νd |
|---|---|---|---|
| Ex. 39 | 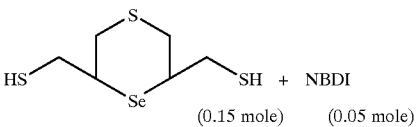 | 1.59 | 44 |

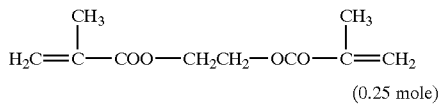

EXAMPLE 40

Synthesis of Selenium Chloride 1300 parts (13 mols) of 98% sulfuric acid were added dropwise to a mixed solution of 710.6 parts (9.0 moles) of metallic selenium, 332.7 parts (3.0 moles) of selenium dioxide and 1500 ml of 36% hydrochloric acid while an internal temperature was maintained at 20 to 30° C. After completion of the addition by the dropping, the solution was heated up to 70° C., followed by aging for 1 hour. After the solution had been cooled to room temperature, the resultant upper aqueous layer was discarded.

Synthesis (1) of a Halogen Compound 72.7 parts (0.438 mole) of diallyl selenide having a purity of 97% were dissolved in 300 ml of dichloroethane, and while the solution was stirred, 100 parts (0.438 mole) of selenium chloride was slowly added dropwise at −50° C. or less. After completion of the addition by the dropping, the solution was held at the same temperature for 2 hours as it was, while the stirring was continued. Furthermore, after the solution had been aged at −25 to −20° C. for 4 hours, cooling was stopped, and the solution was allowed to stand a whole day and night with stirring.

Next, calcium chloride was added to the resultant reaction mass, followed by stirring. Afterward, produced selenium and calcium chloride were removed by filtration, and the solvent was distilled off from the filtrate to obtain 118 parts of crystals including a viscous material. The crystals were recrystallized from a hexane-toluene mixed solution down to −25° C., thereby obtaining 58 parts of crystals (purity=97% according to the measured results of HPLC).

It was confirmed by the results of elemental analysis, MS, NMR and IR analysis that the obtained crystals were 2,6-bis(chloromethyl)-1,4-diselenane.

Synthesis (1) of a Polythiol

Next, 54 parts (0.16 mole) of the above crystals, 38 parts (0.50 mole) of thiourea, 5 parts of 36% hydrochloric acid and 200 ml of anhydrous methanol were mixed with one another, and reaction was carried out at 50° C. for 8 hours with stirring. After cooling, 100 ml of water, 110 parts (1.6 moles) of 25% aqueous ammonia and 800 ml of toluene were added to the reaction system, and the solution was then hydrolyzed at 50° C. for 2 hours. After still standing, the resultant lower aqueous layer was discarded. The resultant organic layer was washed at room temperature with 36% hydrochloric acid and pure water in turn, and the solvent was then distilled off. The remaining residue was purified through silica gel column chromatography to obtain 3 parts of 2,6-dimercaptomethyl-1,4-diselenane having a purity of 94% and represented by the following formula (1-1. The results of identification analysis are as follows:

TABLE 5

(1-1)

HS—CH₂—[ring with Se, Se]—CH₂—SH (Elemental analysis)

|  | C | H | S | Se |
|---|---|---|---|---|
| Calcd. (%) | 23.5 | 3.9 | 20.9 | 51.6 |
| Found (%) | 23.4 | 3.9 | 20.8 | 51.3 |

(MS): m/z = 308 (M⁺)
(IR): SH = 2540–2550 cm⁻¹

EXAMPLE 41

Synthesis (2) of a Halogen Compound

The same reaction as in Example 40 was carried out except that diallyl selenide was replaced with diallyl sulfide.

That is to say, 101 parts (0.876 mole) of diallyl sulfide having a purity of 99% was dissolved in 800 ml of chloroform, and while the solution was stirred, 200 parts (0.876 mole) of selenium chloride was slowly added dropwise thereto at −50° C. or lower. After completion of the addition by the dropping, the solution was held at the same temperature for 2 hours as it was, while the stirring was continued. Furthermore, after aging at −25 to −20° C. for 4 hours, cooling was stopped, and the solution was allowed to stand a whole day and night with stirring.

Next, calcium chloride was added to the resultant reaction mass, followed by stirring. Afterward, produced selenium and calcium chloride were removed by filtration, and the solvent was then distilled off from the filtrate to obtain 200 parts of crystals having a purity of 71% (according to the measured results of HPLC) and including a viscous material.

A part of the obtained crystals was recovered, and a main product was then collected by a silica gel column (hexane/chloroform), so that crystals having a purity of 99% were obtained. The thus obtained crystals were subjected to elemental analysis, MS, NMR and IR analysis, and as a result, it was apparent that the product was 2,6-bis(chloromethyl)-4-thia-1-selenane.

Synthesis (2) of a Polythiol

Next, 150 parts (0.40 mole) of the above crystals having a purity of 71%, 114 parts (1.5 moles) of thiourea and 7500 ml of anhydrous methanol were mixed with one another, and reaction was carried out for 3 hours with stirring under reflux (79° C.). Afterward, the resultant crystals were collected by hot filtration at 70° C.

To the crystals, 113 parts (1.66 moles) of 25% aqueous ammonia, 400 ml of toluene and 150 ml of water were added, and the mixture was hydrolyzed at 60° C. for 2 hours. After still standing, the resultant lower aqueous layer was discarded. The resultant organic layer was washed at room temperature with 36% hydrochloric acid and pure water in turn, and the solvent was then distilled off. 95 parts of the remaining residue were distilled under reduced pressure, i.e., under a vacuum degree of 0.5 Torr to obtain a fraction of 158 to 165° C. In consequence, 41 parts of 3,5-dimercaptomethyl-1-thia-4-selenane having a purity of 99% and the following formula (1-2) were obtained. The results of identification analysis are as follows:

(1-2)

HS—CH₂—[ring with S, Se]—CH₂—SH (Elemental analysis)

|  | C | H | S | Se |
|---|---|---|---|---|
| Calcd. (%) | 27.8 | 4.7 | 37.1 | 30.5 |
| Found (%) | 27.8 | 4.7 | 37.0 | 30.3 |

(MS): m/z = 260 (M⁺)
(IR): SH = 2540 to 2550 cm⁻¹

(1-2)

HS—CH₂—[ring with S (2), Se (1), position (3)]—CH₂—SH (¹³C-NMR)
δ (ppm)

30.3 to 30.4 (1)
33.9 to 34.0 (2)
39.9 to 40.0 (3)

EXAMPLE 42

Synthesis (1) of a Polyisocyanate 100 parts (0.60 mole) of 3,5-diaminoselenophane synthesized by a procedure described in a literature "Journal of Organic Chemistry", Vol. 40, p. 523 (1975) were dissolved in 300 ml of o-dichlorobenzene (hereinafter abbreviated to "ODCB").

In succession, the resultant mixture solution was added dropwise with vigorous stirring over 2 hours to 700 ml of ODCB whose internal temperature was maintained at 130 to 140° C. Simultaneously with the dropping, a hydrogen chloride gas was blown into the solution at 22 g/hr for 2.5 hours.

The thus obtained reaction solution of 3,5-diaminoselenophane hydrochloride was heated up to 165° C., and phosgene and nitrogen were continuously blown into the solution at 95 g/hr and 10 l/hr, respectively, under heating, stirring and reflux (internal temperature=162 to 170° C.) for 4 hours, and consequently, reaction was completed.

Next, while the solution was bubbled by blowing nitrogen thereto at 40 l/hr to remove the gases of phosgene and the hydrogen chloride gas, the solution was cooled to room temperature. Crystals in the cooled reaction solution were removed by filtration, and the resultant filtrate was then heated under reduced pressure to remove the solvent.

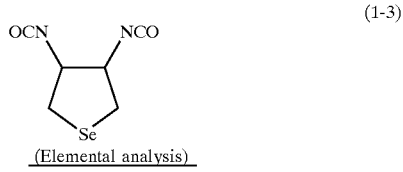

(1-3)

(Elemental analysis)

|  | C | H | N | Se |
|---|---|---|---|---|
| Calcd. (%) | 33.2 | 2.8 | 12.9 | 36.3 |
| Found (%) | 33.1 | 2.9 | 12.7 | 36.2 |

(MS): m/z = 218 (M$^+$)
(IR): NCO = 2240 to 2250 cm$^{-1}$

EXAMPLE 43

Synthesis (1) of a Polythioisocyanate

A solution obtained by dissolving 110 parts (0.60 mole) of 3,5-diaminoselenophane used in Example 42 in 300 ml of toluene was added dropwise to a mixture solution of 76.1 parts (1.0 mole) of carbon disulfide, 81.6 parts (1.0 mole) of an aqueous 49% NaOH solution and 51.7 parts of water at 30 to 40° C., followed by aging at 70 to 80° C. for 3 hours.

After 100 ml of water and 200 ml of toluene had been added to this reaction solution, 100 parts (1.05 moles) of methyl chloroformate were added thereto at 40 to 55° C. After the addition, the solution was gradually heated, and decomposition reaction was carried out for 5 hours under heating and reflux (85° C.).

After completion of the reaction, the lower aqueous layer was discarded.

The upper organic layer was washed with water several times, dried over anhydrous magnesium sulfate, and then filtered. The resultant filtrate was desolvated to obtain 115 parts of a residue. Lastly, this residue was distilled under reduced pressure, i.e. under 4 Torr to obtain a fraction of 210 to 220° C. In consequence, 40 parts (purity conversion yield=31%) of 3,4-diisothiocyanatoselenophane having a purity of 96% and the following formula (1-4) were obtained. The results of identification analysis are as follows:

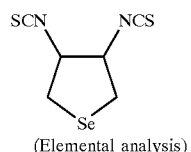

(1-4)

(Elemental analysis)

|  | C | H | N | S | Se |
|---|---|---|---|---|---|
| Calcd. (%) | 28.9 | 2.4 | 11.2 | 25.7 | 31.7 |
| Found (%) | 29.1 | 2.5 | 11.4 | 25.0 | 31.9 |

(MS): m/z = 250 (M$^+$)
(IR): NCS = 2100 to 2200 cm$^{-1}$

EXAMPLE 44

Synthesis (3) of a Halogen Compound 846 parts (3.70 moles) of sulfur chloride were added. dropwise to a mixture solution of 200 parts (1.85 moles) of cyclooctadiene and 200D ml of dichloromethane at −50° C., followed by aging at −50 to −40° C. for 2 hours. After the temperature of the reaction solution had been slowly returned to room temperature, insolubles were removed by filtration, and the filtrate was then desolvated.

According to the results of elemental analysis, GC-MS NMR and IR analysis, the obtained residue was presumed to be 2,6-dichloro-9-selenabicyclononane.

The yield of this residue was 297 parts and its purity was 89% (according to the measured results of GC) (purity conversion yield=55%).

Synthesis (1) of a Polyamine 200 parts (0.690 mole) of the above 2,6-dichloro-9-selenabicyclononane having a purity of 89% and 500 ml of acetonitrile were placed in a 1200 ml stainless steel autoclave. In succession, this autoclave was cooled until its internal temperature had been −30° C. or lower, and 150 g (8.8 moles) of an ammonia gas were then fed thereto.

Next, this autoclave was slowly heated, and reaction was carried out at an internal temperature of 0 to 5° C. under pressure for 2 hours with stirring.

After completion of the reaction, the pressure in the system was returned to atmospheric pressure, and the reaction solution was then filtered to remove insolubles therefrom. The mass removed by the filtration was sludged with chloroform, and then filtered again. Both of these filtrates were joined, and the solvent was removed therefrom, thereby obtaining 80 parts of the residue.

Lastly, this residue was distilled under reduced pressure, i.e., under the pressure of 1 to 2 Torr to obtain a fraction of 160 to 170° C. In consequence, there were obtained 52 parts.(purity conversion yield=33%) of 2,6-diamino-9-selenabicyclononane having a purity of 97% and formula (1-5). The results of identification analysis are as follows:

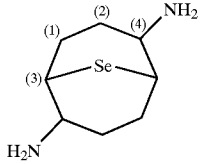

(1-5)

(Elemental analysis)

|  | C | H | N | Se |
|---|---|---|---|---|
| Calcd. (%) | 43.8 | 7.4 | 12.8 | 36.0 |
| Found (%) | 43.6 | 7.4 | 12.7 | 35.8 |

(MS): m/z = 220 (M$^+$)
(IR): NH$_2$ = 3100–3300 cm$^{-1}$
($^{13}$C-NMR)
δ (ppm)

27.1–27.6 (1)
32.2–32.3 (2)
32.4–33.0 (3)
53.8–54.2 (4)

Synthesis (2) of a Polyisocyanate 50 parts (0.221 mole) of 2,6-diamino-9-selenabicyclononane having a purity of 97% were dissolved in 200 ml of aluminum acetate.

In succession, the above mixture solution was added dropwise with stirring over 2 hours to 300 ml of aluminum acetate whose internal temperature was maintained at 20 to 30° C. Simultaneously with the dropping, a hydrogen chloride gas was blown into the solution at 8 to 9 g/hr for 2.5 hours.

The thus obtained reaction solution of 2,6-diamino-9-selenabicyclononane hydrochloride was heated up to 130° C., and phosgene was then continuously blown into the solution at 22 g/hr for 10 hours under heating, stirring and reflux (internal temperature=130 to 140° C.), and consequently, reaction was completed.

After completion of the reaction, the solution was cooled to room temperature while the solution was bubbled by blowing nitrogen thereinto at 20 l/hr. The cooled reaction solution was filtered, and the resultant filtrate was then heated under reduced pressure to remove the solvent.

Lastly, this residue was distilled under reduced pressure, i.e., under the pressure of 1 to 2 Torr to obtain a fraction of 180 to 190° C. In consequence, there were obtained 51 parts (purity conversion yield=84%) of 2,6-diisocyanato-9-selenabicyclononane having a purity of 99% and formula (1-6). The results of identification analysis are as follows:

(1-6)

(Elemental analysis)

|  | C | H | N | Se |
|---|---|---|---|---|
| Calcd. (%) | 44.3 | 4.5 | 10.3 | 29.1 |
| Found (%) | 44.2 | 4.5 | 10.1 | 29.0 |

(MS): m/z = 272 (M$^+$)
(IR): NCO = 2240–2250 cm$^{-1}$

EXAMPLE 45

Synthesis (4) of a Halogen Compound

Reaction was carried out by the same procedure as in Example 41 except that diallyl sulfide was replaced with 1,5-hexadiene as a starting material.

For the collection of a chlorine-containing product, the reaction solution was distilled under reduced pressure, i.e., under a vacuum degree of 1.5 to 2 Torr to obtain 160 parts of a fraction of 96 to 100° C. (purity=97% according to the measured results of GC; purity conversion yield=76%).

It was confirmed by the results of GC-MS and NMR analysis that the obtained liquid was a mixture of 3 kinds of isomers. The results of elemental analysis and the GC-MS are as follows:

(Elemental analysis)

|  | C | H | Cl | Se |
|---|---|---|---|---|
| Calcd. (%) | 31.1 | 4.3 | 30.6 | 34.0 |
| Found (%) | 31.0 | 4.3 | 30.7 | 33.8 |

GC-MS: m/z = 232 (M$^+$)

Next, a part of this fraction was hydrolyzed with water, and some portions were taken by reversed phase chromatography and then subjected to $^1$H-NMR, $^{13}$C-NMR and MS analysis.

The results are as follows:

(Results of Fraction 1)

(a)

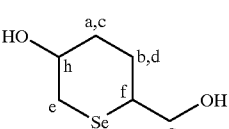

(H-NMR)
δ (ppm)                        Integral ratio

| 3.05 | e | 2 |
| 1.76 | b | 1 |
| 2.37 | d | 1 |
| 1.37 | a | 1 |
| 1.99 | c | 1 |
| 3.05 | f | 1 |

-continued

| | | |
|---|---|---|
| 3.66 | g | 2 |
| 3.86 | h | 1 |

(a)

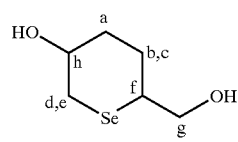

($^{13}$C-NMR)
δ (ppm)

| | |
|---|---|
| 24.86 | (1) |
| 30.25 | (2) |
| 33.72 | (3) |
| 37.62 | (4) |
| 64.83 | (5) |
| 68.10 | (6) |

(MS): m/z = 196 (M$^+$)

(Results of Fraction 2)

(b)

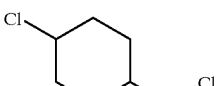

(H-NMR)
δ (ppm)                                    Integral ratio

| | | |
|---|---|---|
| 2.65 | d | 1 |
| 2.77 | e | 1 |
| 2.00 | b | 1 |
| 2.17 | c | 1 |
| 1.65 | a | 2 |
| 2.95 | f | 1 |
| 3.67 | g | 2 |
| 3.86 | h | 1 |

(b)

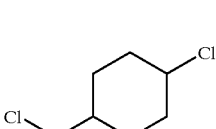

($^{13}$C-NMR)
δ (ppm)

| | |
|---|---|
| 23.94 | (1) |
| 26.41 | (2) |
| 30.32 | (3) |
| 35.30 | (4) |
| 63.66 | (5) |
| 64.96 | (6) |

(MS): m/z = 196 (M$^+$)

That is to say, Fraction 2 is a stereoisomer of Fraction 1.

(Results of Fraction 3)

(c)

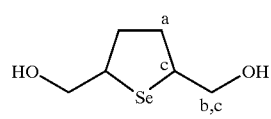

(H-NMR)
δ (ppm)

| | |
|---|---|
| 1.88–2.15 | a |
| 3.66 | c |
| 3.54 | b |

(c)

($^{13}$C-NMR)
δ (ppm)

| | |
|---|---|
| 32.59 | (1) |
| 46.32 | (2) |
| 65.42 | (3) |

(MS): m/z = 196 (M$^+$)

The weight ratio of the above separated compounds was Fraction 1/Fraction 2/Fraction 3=36/33/31.

It was apparent from the above results that the thus distilled fraction was the mixture of the following isomers.

(a')

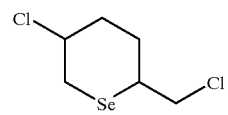

36%

(b')

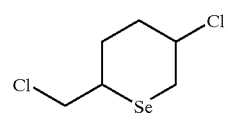

33%

(c')

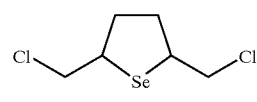

31%

100 parts (0.418 mole) of the above chlorine-containing product having a purity of 97%, 114 parts (1.5 moles) of thiourea and 300 ml of water were mixed with one another, and reaction was carried out for 3 hours with stirring under reflux (100 to 110° C.). Afterward, the reaction solution was cooled to 40° C. or lower.

To the resultant reaction solution, 200 ml of toluene and 113 parts (1.66 moles) of 25% aqueous ammonia were added, and the solution was then hydrolyzed at 60° C. for 2 hours. After still standing, the resultant lower aqueous layer was discarded. The resultant organic layer was washed at room temperature with 36% hydrochloric acid and pure water in turn, and the solvent was then distilled off.

The remaining residue was distilled under reduced pressure, i.e., under a vacuum degree of 0.5 to 2 Torr to obtain a fraction of 127 to 160° C. In consequence, 90 parts of 2,5-bis(mercaptomethyl)selenophane of purity=99% represented by the following formula (C) were obtained (purity conversion yield=83%). The results of identification analysis are as follows:

(C)

HS–[ring with Se]–SH (Elemental analysis)

|  | C | H | N | Se |
|---|---|---|---|---|
| Calcd. (%) | 31.7 | 5.3 | 28.2 | 34.7 |
| Found (%) | 31.8 | 5.3 | 28.0 | 34.6 |

(C)

HS–(3)[ring with Se(1)](2)–SH (MS): m/z = 228 (M$^+$)
(IR): SH = 2540–2550 cm$^{-1}$
($^{13}$C-NMR)
δ (ppm)

31.4 (1)
36.5 (2)
48.7 (3)

EXAMPLE 46

Synthesis of an Azide Compound 175 parts (0.74 mole) of the chlorine-containing product having a purity of 98% synthesized in the same manner as in Example 45, 250 parts (3.5 mols) of sodium azide, 600 ml of toluene, 500 ml of water and 40 g of tetrabutylammonium bromide were mixed with one another, and reaction was carried out under stirring, heating and reflux for 10 hours.

After cooling, the reaction solution was filtered to remove insolubles therefrom.

The resultant filtrate was separated, and the lower aqueous layer was discarded and the upper organic layer was then desolvated.

The yield and the purity of the residue were 180 parts and 87%, respectively, and the molecular weight of its peak was 246 (according to the measured results of GC-MS; purity conversion yield=87%).

It was presumed from the above results that the obtained main product was a desired 2,5-bis(azidomethyl) selenophane.

Synthesis (2) of a Polyamine 90 parts (0.542 mole) of triethylphosphine were added dropwise to a mixture solution of 157 parts (0.537 mole) of 2,5-bis(azidomethyl)selenophane having a purity of 87% and 300 ml of toluene at an internal temperature of 30 to 35° C., and the solution was then allowed to stand at room temperature for 10 hours.

Toluene was removed from the solution, and to the resultant residue, 400 g (2.2 moles) of 20% hydrochloric acid were added dropwise and reaction was carried out for 2 hours under heating and reflux (90 to 100° C.).

After cooling, 270 parts (3.3 moles) of a 49% aqueous NaOH solution were added dropwise thereto under cooling, and extraction was then conducted 4 times with 300 ml of chloroform (room temperature).

Lastly, the chloroform extract was desolvated, and the remaining residue was then distilled under reduced pressure, i.e., under a vacuum degree of 1 to 2 Torr to obtain a fraction of 120 to 130° C. In consequence, 77 parts of 2,5-bis (aminomethyl)selenophane having a purity of 98% and the following formula (E) were obtained (purity conversion yield=73%). The results of identification analysis are as follows:

(E)

H$_2$N–[ring with Se]–NH$_2$ (MS): m/z = 194 (M$^+$)
(IR): NH$_2$ = 3280–3350 cm$^{-1}$ (E)

H$_2$N–(3)[ring with Se(1)](2)–NH$_2$ ($^{13}$C-NMR)
δ (ppm)

48.3 (1)
34.6 (2)
49.6 (3)

Synthesis (3) of a Polyisocyanate

Synthesis was carried out by the same procedure as in Example 44 except that 70 parts (0.341 mole) of bis (aminomethyl)selenophane of purity=98% were used.

In consequence, 68 parts of bis(isocyanatomethyl) selenophane having a purity of 96% and the following formula (F) were obtained (purity conversion yield=78%). The results of identification analysis are as follows:

(F)

OCN–[ring with Se]–NCO

MS): m/z = 246 (M$^+$)
(IR): NCO = 2240–2250 cm$^{-1}$ (Elemental analysis)

|  | C | H | N | Se |
|---|---|---|---|---|
| Calcd. (%) | 39.2 | 4.1 | 11.4 | 32.1 |
| Found (%) | 39.0 | 4.1 | 11.3 | 32.3 |

EXAMPLE 47

Synthesis of a Acrylate Compound

Under bubbling with nitrogen, 42 parts (0.66 mole) of 3-chloropropionic acid chloride were added dropwise to 50 parts (0.218 mole) of 2,5-bis(mercaptomethyl)selenophane having a purity of 99% and heated up to 50° C., followed by aging at the same temperature.

After 300 ml of toluene had been added to the resultant reaction solution-, water washing was repeated several times.

To the resultant organic layer, 0.1 part of 2,6-di-tert-butyl-4-methylphenol was added, and while an internal temperature was maintained at 10 to 15° C., 44.5 parts (0.44 mole) of triethylamine were added dropwise thereto, followed by aging at the same temperature for 2 hours.

Next, the solution was subjected to acid washing with 200 ml of 3% hydrochloric acid, and then water washing several times. Afterward, the solvent was removed, followed by filtration, thereby obtaining 68 parts of a residue having a purity of 90% (according to the measured results of HPLC).

This residue was purified through silica gel column chromatography to obtain 56 parts of 2,5-bis(acryloylthiomethyl)selenophane having a purity of 97% and the following formula (23) (purity conversion yield= 74%). The results of identification analysis are as follows:

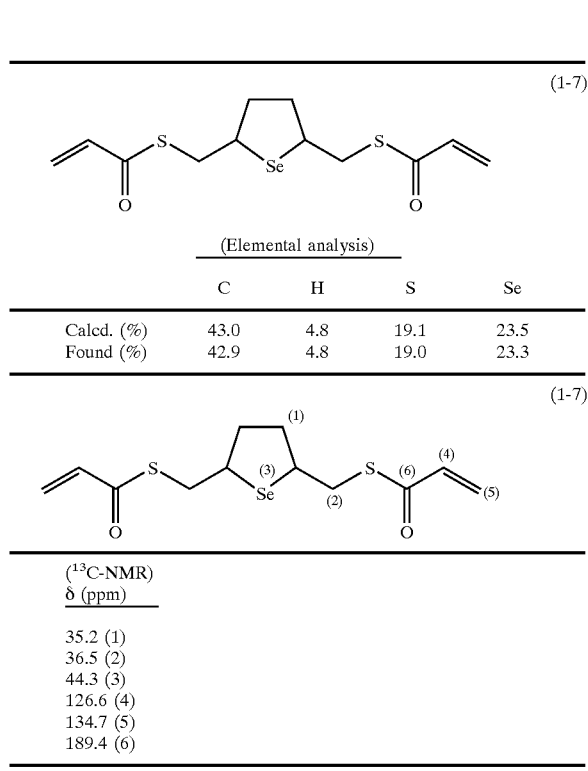

(1-7)

(Elemental analysis)

| | C | H | S | Se |
|---|---|---|---|---|
| Calcd. (%) | 43.0 | 4.8 | 19.1 | 23.5 |
| Found (%) | 42.9 | 4.8 | 19.0 | 23.3 |

(1-7)

($^{13}$C-NMR)
δ (ppm)

35.2 (1)
36.5 (2)
44.3 (3)
126.6 (4)
134.7 (5)
189.4 (6)

EXAMPLE 48

Synthesis of a Epoxy Compound 50 parts (0.218 mole) of 2,5-bis(mercaptomethyl)selenophane having a purity of 99%, 60 ml of water and 0.6 part of a 49% aqueous NaOH solution were mixed with one another, and 40.4 parts (0.436 mole) of epichlorohydrin were slowly added dropwise to the mixture while an internal temperature was maintained at 10 to 20° C., followed by aging at the same temperature for 1 hour.

To this reaction solution, 70 parts (0.86 mole) of the 49% aqueous NaOH solution were added dropwise while an internal temperature was maintained at 5 to 10° C., followed by aging at 10° C. for 2 hours.

Next, 300 ml of dichloroethane was added to the resultant reaction solution to perform extraction. The resultant extract was washed with water several times, and the solvent was then distilled off to obtain 73 parts of 2,5-bis(glycidylthiomethyl)selenophane having a purity of 94% (according to the measured results of HPLC) and the following formula (J) (purity conversion yield 93%).

The results of identification analysis are as follows:

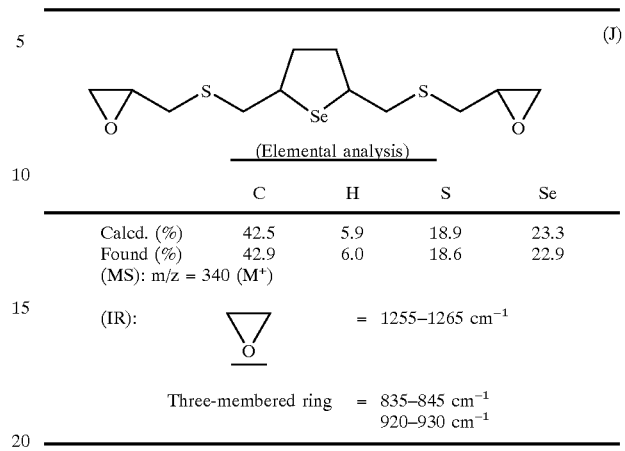

(J)

(Elemental analysis)

| | C | H | S | Se |
|---|---|---|---|---|
| Calcd. (%) | 42.5 | 5.9 | 18.9 | 23.3 |
| Found (%) | 42.9 | 6.0 | 18.6 | 22.9 |
| (MS): m/z = 340 (M$^+$) | | | | |

(IR):  ▽O  = 1255–1265 cm$^{-1}$

Three-membered ring = 835–845 cm$^{-1}$
920–930 cm$^{-1}$

EXAMPLE 49

Synthesis of a Episulfide Compound 50 parts (0.138 mole) of 2,5-bis(glycidylthiomethyl)selenophane (J) having a purity of 94% synthesized in Example 48, 67 parts (0.69 mole) of potassium thiocyanate and 50 ml of water were mixed with one another, and reaction was carried out at an internal temperature of 50° C. for 9 hours.

To the resultant reaction solution, 300 ml of toluene and 300 ml of water were added, followed by stirring. After still standing, the lower aqueous layer was discarded.

The upper organic layer was washed with 1% sulfuric acid, and then washed with water several times. The solvent was distilled off to obtain 52.5 parts of a residue having a purity of 87% (according to the measured results of HPLC).

This residue was purified through silica gel column chromatography to obtain 40 parts of 2,5-bis(4,5-epithio-2-thiapentyl)selenophane having a purity of 98% and the following formula (K) (purity conversion yield=76%).

The results of identification analysis are as follows:

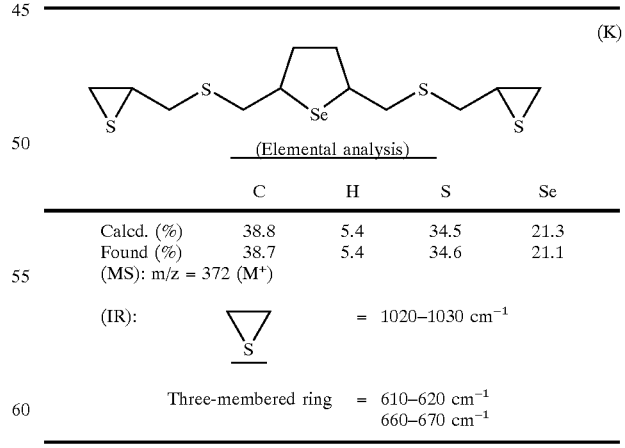

(K)

(Elemental analysis)

| | C | H | S | Se |
|---|---|---|---|---|
| Calcd. (%) | 38.8 | 5.4 | 34.5 | 21.3 |
| Found (%) | 38.7 | 5.4 | 34.6 | 21.1 |
| (MS): m/z = 372 (M$^+$) | | | | |

(IR):  ▽S  = 1020–1030 cm$^{-1}$

Three-membered ring = 610–620 cm$^{-1}$
660–670 cm$^{-1}$

EXAMPLE 50

Synthesis of a Ester Compound 60 parts (0.76 mole) of metallic seleniun were dispersed in 100 ml of anhydrous methanol, and a solution obtained by dissolving 35 parts of sodium borohydride in 500 ml of anhydrous methanol was slowly added dropwise to the suspension under cooling on a water bath, followed by aging for 1 hour.

To this reaction solution, 126 parts (0.38 mole) of ethyl meso-dibromosuccinate obtained by brominating ethyl fumarate were dividedly added over 1 hour and reaction was then carried out at room temperature for 96 hours. After completion of the reaction, insolubles were removed by filtration, and the resultant filtrate was then desolvated.

To the remaining residue, 400 ml of dichloroethane were added, and 10 ml of concentrated sulfuric acid was added dropwise to the solution to make the reaction solution strongly acidic. Afterward, 11.4 parts (0.38 mole) of paraformaldehyde was dividedly slowly added to the solution, followed by aging for 24 hours.

After completion of the aging, the solution was washed with water several times, and the lower organic layer was then desolvated to obtain 88 parts of a residue including ethyl 1,3-diselenoran-2,5-dicarboxylate.

Synthesis (4) of a Polyisocyanate 38 parts (0.76 mole) of hydrazine monohydrate were added to a mixture solution of 88 parts of the residue containing ethyl 1,3-diselenoran-2,5-dicarboxylate and 200 ml of isopropanol while the solution was maintained at 5 to 10° C., followed by aging for 3 hours.

The resultant insoluble substance was collected by filtration, washed with isopropanol, and then dried under reduced pressure.

79 parts (0.78 mole) of 35% hydrochloric acid were added dropwise to a mixture solution of the resultant crystals and 200 ml of water while the solution was maintained at 5° C. In succession, an aqueous solution obtained by dissolving 54 parts (0.78 mole) of sodium nitrite in 220 ml of water was added dropwise thereto at the same temperature, followed by aging for 1 hour.

Next, 500 ml of toluene was-similarly added to the solution at 5° C. to perform extraction, and the lower aqueous layer was discarded. To the upper organic layer, anhydrous magnesium sulfate was added for dehydration, followed by filtration. The resultant filtrate was kept at 5° C.

While kept at 5° C., this filtrate was slowly added dropwise to toluene heated up to 90° C., and aging was continued until the generation of nitrogen had stopped.

After the solution had been cooled to room temperature, insolubles were removed by filtration, and the resultant filtrate w as desolvated.

Lastly, this residue was distilled under reduced pressure to obtain 6 parts of 3,4-diisocyanato-2,5-diselenoran having a purity of 92% (according to the measured results of GC) and the following formula (1-8) (purity conversion yield=5%). The results of identification analysis are as follows:

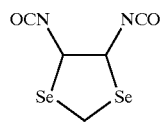

(1-8)

(Elemental analysis)

|  | C | H | N | Se |
|---|---|---|---|---|
| Calcd. (%) | 21.3 | 1.4 | 9.9 | 56.0 |
| Found (%) | 21.1 | 1.4 | 9.8 | 55.7 |

(MS): m/z = 284 (M$^+$)
(IR): NCO = 2240–2250 cm$^{-1}$

EXAMPLE 51

60 parts (0.76 mole) of metallic selenium were suspended in 1000 ml of anhydrous methanol, and to the suspension, a mixture solution of 35 parts (0.925 mole) of sodium borohydride and 500 ml of anhydrous methanol was slowly added dropwise while the solution was cooled, followed by aging for 1 hour.

Next, the reaction solution was desolvated and then concentrated to about 500 ml, and to the thus concentrated solution, 95 parts (0.76 mole) of 2-bromoethanol were added dropwise while an internal temperature was maintained at 20 to 30° C., followed by aging at room temperature for 20 hours.

After the aging, 31 parts (0.38 mole) of 49% caustic soda (an aqueous sodium hydroxide solution) were added dropwise to the solution at room temperature while the solution was cooled, to form a salt.

To this salt mass, 90 parts (0.38 mole) of the chlorine-containing product having a purity of 98% synthesized in the same manner as in Example 45 were added dropwise at an internal temperature of 30 to 40° C., followed by aging at 70° C. for 2 hours.

After cooling, 100 parts (1.3 moles) of thiourea and 200 parts (2.0 moles) of 36% hydrochloric acid were added to the aged solution, and reaction was carried out for 2 hours under heating and reflux.

After cooling to room temperature, 400 ml of toluene and 160 parts (2.4 moles) of 25% aqueous ammonia were added to the cooled solution, and the solution was hydrolyzed at 60° C. for 2 hours. After still standing, the lower aqueous layer was discarded.

After cooling, the resultant organic layer was washed with 36% hydrochloric acid and pure water in turn, and the solvent was then distilled off. The remaining residue was purified through silica gel column chromatography to obtain 80 parts of 2,5-bis(4-mercapto-2-selenabutyl)selenophane having a purity of 97% and the following formula (1-9) (purity conversion yield=46%). The results of identification analysis are as follows:

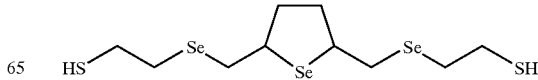

(1-9)

(Elemental analysis)

|  | C | H | S | Se |
|---|---|---|---|---|
| Calcd. (%) | 27.2 | 4.6 | 14.5 | 53.7 |
| Found (%) | 27.1 | 4.6 | 14.4 | 53.5 |

(MS): m/z = 444 (M$^+$)
(IR): NCO = 2540–2250 cm$^{-1}$

EXAMPLE 52

Preparation of a Plastic Lens 30.6 parts (0.10 mole) of 2,6-bis(mercaptomethyl)-1,4-diselenane, 18.8 parts (0.10 mole) of m-xylylene diisocyanate (hereinafter abbreviated to "IXDI"), 0.05 part (1000 ppm) of dibutyltin dichloride an 0.05 part (1000 ppm) of dioctylphosphoric acid were uniformly mixed with one another to prepare a uniform solution, followed by defoaming at room temperature under reduced pressure.

After 1 hour, the solution was poured into a concave lens mold comprising a glass mold and a gasket and having a central thickness of 1.5 mm, and this mold was then slowly heated from room temperature to 120° C. to cure the solution in 20 hours. Furthermore, this mold was heated at 120° C. again to obtain a transparent plastic lens.

The results of the obtained lens are shown in Table 5.

EXAMPLES 53 AND 54, COMPARATIVE EXAMPLES 4 AND 5

Plastic lenses were obtained by the same procedure as in Example 40. The results of the obtained lenses are shown in Table 5.

EXAMPLE 55

Preparation (2) of a Plastic Lens 30 parts of 2,5-bis(4,5-epithio-2-thiapentyl)selenophane and 0.06 part (2000 ppm) of tributylamine were mixed and dissolved at 70° C. while defoaming was conducted under reduced pressure. After 30 minutes, the solution was poured into the lens mold of Example 49, and this mold was slowly heated from 70 to 80° C. to cure the solution in 16 hours, thereby obtaining a transparent plastic lens. The results of the obtained lens are shown in Table 5.

TABLE 5

| | Composition | Nd | vd | Gravity | Tg |
|---|---|---|---|---|---|
| Ex. 52 | 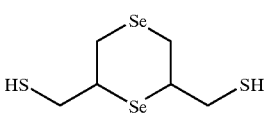 + XDI | 1.690 | 32 | 1.59 | 120° C. |
| Ex. 53 | 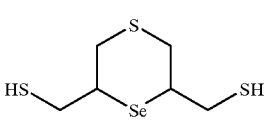 + XDI | 1.674 | 32 | 1.50 | 110° C. |
| Ex. 54 | 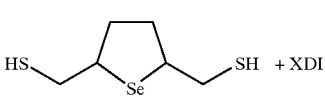 + XDI | 1.658 | 32 | 1.48 | 96° C. |
| Comp. Ex. 4 | 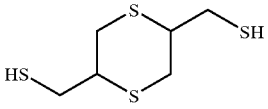 + XDI | 1.662 | 32 | 1.37 | 103° C. |
| Comp. Ex. 5 | 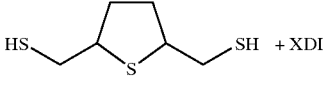 + XDI | 1.643 | 33 | 1.38 | 85° C. |
| Ex. 55 | 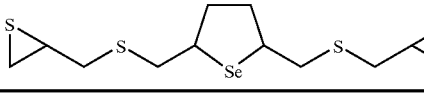 | 1.701 | 37 | 1.51 | 88° C. |

EXAMPLE 56

Synthesis (1) of a Polyol 24.7 parts (0.313 mole) of metallic selenium, 90 parts (0.584 mole) of Rongalit (HOCH$_2$SO$_2$Na.2H$_2$O) and 70 parts (1.75 moles) of sodium hydroxide were dissolved in 400 ml of water, and to the solution, 95.5 parts (0.616 mole) of 1-bromo-2,3-propanediol were then slowly added dropwise at room temperature, followed by aging at 50° C. for 6 hours.

After completion of reaction, water was distilled off under reduced pressure, and 500 ml of isopropanol were added to and mixed with the solution. Next, insolubles were removed therefrom by filtration. The resultant filtrate was desolvated to obtain 69 parts (gross yield=96%) of a residue including-bis(2,3-dihydroxy-1-propyl)selenide.

Synthesis of a Halogen Compound

To this residue, 140 parts (0.517 mole) of phosphorus tribromide were added dropwise while an internal temperature was maintained at 50° C., followed by aging at 80° C. for 10 hours.

After the solution had been cooled to room temperature, 300 ml of chloroform was added thereto, and 100 ml of water was slowly added to the mixture solution to wash it with water. Furthermore, this water washing was repeated several times.

The lower organic layer was desolvated to obtain 141 parts of a residue including bis(2,3-dibromo-1-propyl) selenide (gross yield=94%).

Synthesis (1) of a Polythiol

This residue was mixed with 190 parts (2.50 moles) of thiourea and 1000 ml of anhydrous ethanol, and reaction was carried out for 20 hours with stirring under heating and reflux (78 to 79° C.). After cooling, the resultant insolubles were collected by filtration.

This filtered mass was mixed with 300 ml of toluene, and to the mixture solution, 170 parts (2.50 moles) of 25% aqueous ammonia were slowly added, followed by hydrolysis at an internal temperature of 50 to 60° C. for 3 hours. After still standing, the lower aqueous layer was discarded.

The resultant organic layer was washed at room temperature with 36% hydrochloric acid and pure water in turn, and the solvent was then distilled off. The remaining residue was purified through silica gel column chromatography to obtain 40 parts of a polythiol having a purity of 95% (by HPLC) and the following formula (3-1) (purity conversion yield= 41%). The results of identification analysis are as follows:

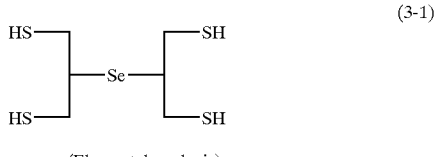

(3-1)

(Elemental analysis)

| | C | H | S | Se |
|---|---|---|---|---|
| Calcd. (%) | 24.6 | 4.8 | 43.7 | 26.9 |
| Found (%) | 24.5 | 4.9 | 43.4 | 26.8 |

(MS): m/z = 294 (M$^+$)
(IR): SH = 2540–2550 cm$^{-1}$

EXAMPLE 57

Synthesis (2) of a Polyol 60 parts (0.76 mole) of metallic selenium were suspended in 1000 ml of anhydrous methanol, and a solution obtained by dissolving 35 parts (0.925 mole) of sodium borohydride in 500 ml of anhydrous methanol was slowly added dropwise to the suspension under cooling, followed by aging for 1 hour at room temperature.

The resultant reaction solution was desolvated until a solution volume had been about 500 ml, and to the thus concentrated solution, 95 parts (0.76 mole) of bromoethanol were added dropwise while an internal temperature was maintained at 20 to 30° C., followed by aging at room temperature for 20 hours.

31.0 parts (0.38 mole) of 49% caustic-soda were added dropwise to this reaction solution while an internal temperature was maintained at 20 to 30° C., followed by aging at room temperature for 1 hour. Furthermore, 35.2 parts (0.38 mole) of epichlorohydrin were added dropwise thereto at an internal temperature of 30 to 40° C., followed by aging at the same temperature for 2 hours. Lastly, the solution was desolvated to obtain a residue including 1,3-bis (hydroxyethylseleno)-2-propanol.

Synthesis (2) of a Polythiol 100 parts (1.31 moles) of thiourea and 200 parts (1.98 moles) of 36% hydrochloric acid were added to the above residue, and reaction was carried out for 2 hours under heating and reflux (108 to 110° C.).

After the solution had been cooled to room temperature, 400 ml of toluene and 160 parts (2.35 moles) of 25% aqueous ammonia were added thereto, followed by hydrolysis at 60° C. for 2 hours. After still standing, the lower aqueous layer was discarded.

The resultant organic layer was washed at room temperature with 36% hydrochloric acid and pure water in turn, and the solvent was then distilled off. The remaining residue was purified through silica gel column chromatography to obtain 90 parts of 2,3-bis(mercaptoethylseleno)-1-propanethiol having a purity of 96% (by HPLC) and the following formula (3-2) (purity conversion yield=64%).

The results of identification analysis are as follows:

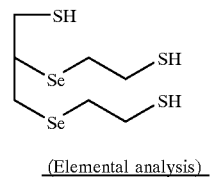

(3-2)

(Elemental analysis)

| | C | H | S | Se |
|---|---|---|---|---|
| Calcd. (%) | 23.7 | 4.6 | 27.1 | 44.6 |
| Found (%) | 23.5 | 4.5 | 27.2 | 44.4 |

(MS): m/z = 356 (M$^+$)
(IR): SH = 2540–2550 cm$^{-1}$

EXAMPLE 58

Preparation of a Plastic Lens 30 parts of 2,3-bis(mercaptoethylseleno)-1-propanethiol (3-2) obtained in Example 57, 24 parts of m-xylylene diisocyanate (hereinafter abbreviated to "XDI"), 0.008 part (150 ppm) of dibutyltin dichloride and 0.06 part (1100 ppm) of dioctylphosphoric acid were mixed and dissolved, while defoaming was conducted under reduced pressure.

After 1 hour, the solution was poured into a concave lens mold comprising a glass mold and a resinous gasket and having a central thickness of 1.5 mm, and this mold was then slowly heated from room temperature to 120° C. to cure the solution in 20 hours. After cooling, the resultant plastic lens was taken out of the mold. Furthermore, this plastic lens was heated at 120° C. again. The results of the obtained lens are shown in Table 6.

COMPARATIVE EXAMPLE 6

The same test as in Example 58 was conducted except that 2,3-bis(mercaptoethylseleno)-1-propanethiol was replaced with 2,3-bis(mercaptoethylthio)-1-propanethiol. The results are shown in Table 6.

TABLE 6

| Composition | | Nd | vd | Tg |
|---|---|---|---|---|
| Ex. 58 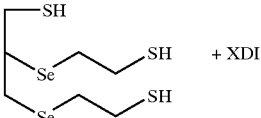 | + XDI | 1.674 | 30 | 92° C. |
| Comp. Ex. 6 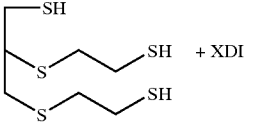 | + XDI | 1.660 | 32 | 85° C. |

EXAMPLE 59

Synthesis of a Polythiol 24.7 parts (0.313 mole) of metallic selenium, 90 parts (0.584 mole) of Rongalit ($HOCH_2SO_2Na.2H_2O$) and 70 parts (1.75 moles) of sodium hydroxide were dissolved in 400 ml of water, and to the resultant solution, 77 parts (0.616 mole) of bromoethanol were then slowly added dropwise at room temperature, followed by aging at 50° C. for 6 hours.

After completion of reaction, water was distilled off under reduced pressure, and 500 ml of isopropanol were added to and mixed with the solution. Next, insolubles were removed therefrom-by filtration. The resultant filtrate was desolvated to obtain a residue including bis(2-hydroxyethyl)selenide.

To this residue, 60 parts (0.788 mole) of thiourea and 100 parts (0.988 mole) of 36% hydrochloric acid were added, and reaction was carried out for 1 hour under heating and reflux (108–110° C.).

After cooling, 300 ml of toluene was added to the solution, and to the resultant mixture solution, 90 parts (1.32 moles) of 25% aqueous ammonia were slowly added, followed by hydrolysis at 50 to 60° C. for 3 hours. After still standing, the lower aqueous layer was discarded.

After cooled to room temperature, the resultant organic layer was washed with 36% hydrochloric acid and pure water several times, and the solvent was then distilled off. The resultant residue was distilled under reduced pressure to obtain 47 parts of bis(2-mercaptoethyl)selenide having a purity of 98% (according to the measured results of GC) (purity conversion yield=73%).

Synthesis of a Acrylate 70 parts (0.55 mole) of 3-chloropropionic acid chloride was added to 40 parts (0.20 mole) of bis(2-mercaptoethyl) selenide having a purity of 98% which was heated and stirred at 50C, while the solution was bubbled with nitrogen, and the solution was then aged at the same temperature for 5 hours.

Next, an excessive amount of 3-chloropropionic acid chloride was distilled off as much as possible under reduced pressure, and 400 ml of toluene was added and water washing was then repeated.

To the resultant organic layer, 0.1 part of 2,6-di-tert-butyl-4-methylphenol was added, and 42 parts (0.42 mole) of triethylamine were added dropwise while an internal temperature was maintained at 10 to 15° C., followed by aging at the same temperature for 2 hours.

After the aging, the solution was washed twice with 200 ml of 3% hydrochloric acid, and water washing was repeated several times. Afterward, the solution was desolvated at 40° C. or lower, followed by filtration, thereby obtaining a residue containing bis(acryloylthioethyl)selenide. This residue was purified through silica gel column chromatography to obtain 50 parts of bis(acryloylthioethyl)selenide having a purity of 98% (according to the measured results of HPLC) and the following formula (5-1) (purity conversion yield= 79%). The results of identification analysis are as follows:

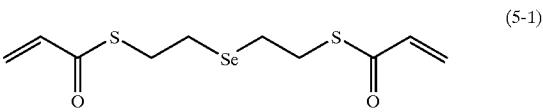
(5-1)

| (Elemental analysis) | | | | |
|---|---|---|---|---|
| | C | H | S | Se |
| Calcd. (%) | 38.8 | 4.6 | 20.7 | 25.5 |
| Found (%) | 38.6 | 4.6 | 20.6 | 25.4 |

(MS): m/z = 310 ($M^+$)
(IR): C=C = 1610–1620 $cm^{-1}$
3090–3100 $cm^{-1}$
SC(O) = 1670–1680 $cm^{-1}$

EXAMPLE 60

Synthesis of a Epoxy Compound 19.7 parts (0.25 mole) of metallic selenium were suspended in 350 ml of anhydrous methanol, and a solution comprising 11.5 parts (0.30 mole) of sodium borohydride and 150 ml of anhydrous methanol was added dropwise to the suspension on a water bath, followed by aging for 1 hour.

While an internal temperature was maintained at 10 to 15° C., the resultant reaction solution was added dropwise to 107 parts (1.16 moles) of epichlorohydrin, followed by aging for 1 hour.

Next, 143 parts (1.0 mole) of a 28% aqueous NaOH solution were added dropwise to the aged solution, while the internal temperature was maintained at 10 to 15° C., followed by aging for 1 hour.

Dichloroethane was added to the resultant reaction solution to conduct extraction, and after water washing had been repeated several times, the solvent and an excessive amount of epichlorohydrin were distilled off. Lastly, the remaining residue was distilled under reduced pressure to obtain 21 parts of diglycidyl selenide having a purity of 97% (according to-the measured results of GC) (purity conversion yield=42%).

Synthesis of a Thioepoxy Compound 39 parts (0.51 mole) of thiourea, 1 part of acetic anhydride, 100 ml of toluene and 100 ml of methanol were added to 20 parts (0.10 mole) of diglycidyl selenide having a purity of 97% (by GC), followed by reaction at 30° C. for 3 hours.

After completion of the reaction, 200 ml of toluene and 200 ml of water were added to the solution, and insolubles were then removed by filtration. The lower layer (the aqueous layer) of the resultant filtrate was discarded.

The upper organic layer was washed with 1% sulfuric acid, and after water washing had been repeated several times, the solvent was distilled off to obtain 15 parts of a residue (gross yield=67%).

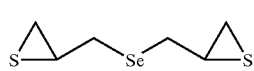

(5-2)

(Elemental analysis)

| | C | H | S | Se |
|---|---|---|---|---|
| Calcd. (%) | 32.0 | 4.5 | 28.5 | 35.1 |
| Found (%) | 31.8 | 4.5 | 28.6 | 35.0 |

(MS): m/z = 226 (M$^+$)
(IR): $\bigtriangledown$ = 1020–1030 cm$^{-1}$
S
Three-membered ring = 610–620 cm$^{-1}$
660–670 cm$^{-1}$

EXAMPLE 61

Preparation of a Plastic Lens 40 parts of bis(acryloylthioethyl)selenide (5-1) were mixed with 0.012 part (300 ppm) of benzylmethylketal to form a uniform solution, and this solution was then defoamed under reduced pressure and under light shielding.

After 0.5 hour, the solution was poured into a concave lens mold comprising a glass mold and a gasket and having a central thickness of 1.5 mm, and this mold was then irradiated with ultraviolet light. After cooling, the resultant lens was taken out of the mold. Furthermore, this lens was heated at 120° C. again to obtain a transparent plastic lens. The results of the obtained lens are shown in Table 7.

EXAMPLE 62

10 parts of bis(2,3-epithio-1-propyl)selenide (5-2) were mixed with 0.02 part (2000 ppm) of triethylamine to prepare a uniform solution, and this solution was then defoamed under reduced pressure.

After 0.5 hour, the solution was poured into a concave lens mold comprising a glass mold and a gasket and having a central thickness of 1.5 mm, and this mold was then slowly heated from room temperature to 80° C. to cure the solution in 20 hours.

After cooling, the resultant transparent plastic lens was taken out of the mold. The results of the obtained lens are shown in Table 7.

COMPARATIVE EXAMPLE 7

A plastic lens was obtained by the same procedure as in Example 61 except that bis(2,3-epithio-1-propyl)selenide (5-1) was replaced with bis(2,3-epithio-1-propyl)sulfide. The results of the obtained lens are shown in Table 7.

TABLE 7

| | Composition | Nd | vd |
|---|---|---|---|
| Ex. 61 | (acryloyl-S-CH₂CH₂-Se-CH₂CH₂-S-acryloyl structure) | 1.65 | 35 |
| Ex. 62 | (epithio-CH₂-Se-CH₂-epithio structure) | 1.73 | 34 |
| Comp. Ex. 7 | (epithio-CH₂-S-CH₂-epithio structure) | 1.70 | 37 |

What is claimed is:
1. A selenium-containing alicyclic compound represented by formula (1):

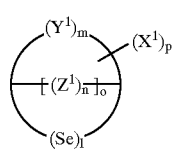

(1)

wherein, Y$^1$ and Z$^1$ each represent —CH$_2$—, =CH—, C atom, Se atom, S atom, SO$_2$, SO or O atom, and the hydrogen atom of methylene or methine may also be substituted by a C$_1$ to C$_3$ lower alkyl group, C$_1$ to C$_3$ lower alkoxy group, C$_1$ to C$_3$ lower alkylthio group, F atom, Cl atom or Br atom; X$^1$ represents a functional group selected from an SH group, NCO group, NCS group, acryloyl group, methacryloyl group, vinyloxy group, vinylthio group, vinylseleno group, vinyl carbonate group, vinyl thiocarbonate group, vinyl selenocarbonate group, allyloxy group, allylthio group, allylseleno group, allyl carbonate group, allyl thiocarbonate group, allyl selenocarbonate group, isopropenyloxy group, isopropenylthio group, isopropenylseleno group, isopropenyl carbonate group, isopropenyl thiocarbonate group, isopropenyl selenocarbonate group, epoxy group and thioepoxy group, or an alkyl residue composed of such functional group and an alkylene group having 10 or less carbon atoms; l, m, n, o and p represent an integer of 1 to 5, 2 to 10, 0 to 5, 0 to 3 and 2 to 6, respectively.

2. The selenium-containing alicyclic compound of claim 1, wherein the-alicyclic structure is 4 to 10-membered ring.

3. The selenium-containing alicyclic compound of claim 1, wherein the alicyclic structure is 5 to 9-membered ring and the alkylene group is composed of 0 to 4 carbon atoms.

4. A composition including at least one selenium-containing alicyclic compound of claim 1.

5. The composition including at least one selenium-containing alicyclic compound of claim 1.

6. The composition including at least one selenium-containing alicyclic compound of claim 1.

* * * * *